United States Patent
Hubbell et al.

(10) Patent No.: US 11,655,500 B2
(45) Date of Patent: May 23, 2023

(54) METHODS, SYSTEMS, AND COMPUTER READABLE MEDIA FOR REPEAT SEQUENCING

(71) Applicant: LIFE TECHNOLOGIES CORPORATION, Carlsbad, CA (US)

(72) Inventors: Earl Hubbell, Palo Alto, CA (US); Christian Koller, San Francisco, CA (US); Nils Homer, Arlington, MA (US)

(73) Assignee: Life Technologies Corporation, Carlsbad, CA (US)

( * ) Notice: Subject to any disclaimer, the term of this patent is extended or adjusted under 35 U.S.C. 154(b) by 935 days.

(21) Appl. No.: 16/429,266

(22) Filed: Jun. 3, 2019

(65) Prior Publication Data

US 2020/0024656 A1   Jan. 23, 2020

Related U.S. Application Data

(63) Continuation of application No. 14/048,843, filed on Oct. 8, 2013, now Pat. No. 10,329,608.

(60) Provisional application No. 61/712,686, filed on Oct. 11, 2012, provisional application No. 61/712,206, filed on Oct. 10, 2012.

(51) Int. Cl.
*C12Q 1/6869* (2018.01)
*G16B 30/00* (2019.01)

(52) U.S. Cl.
CPC ........... *C12Q 1/6869* (2013.01); *G16B 30/00* (2019.02); *C12Q 2535/122* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,210,015 A | 5/1993 | Gelfand et al. |
| 5,399,491 A | 3/1995 | Kacian et al. |
| 5,750,341 A | 5/1998 | Macevicz |
| 5,854,033 A | 12/1998 | Lizardi |
| 6,174,670 B1 | 1/2001 | Wittwer et al. |
| 6,210,891 B1 | 4/2001 | Nyren et al. |
| 6,258,568 B1 | 7/2001 | Nyren |
| 6,274,320 B1 | 8/2001 | Rothberg et al. |
| 6,404,907 B1 | 6/2002 | Gilchrist et al. |
| 6,780,591 B2 | 8/2004 | Williams et al. |
| 6,828,100 B1 | 12/2004 | Ronaghi |
| 6,833,246 B2 | 12/2004 | Balasubramanian |
| 6,911,327 B2 | 6/2005 | McMillan et al. |
| 7,037,687 B2 | 5/2006 | Williams et al. |
| 7,049,645 B2 | 5/2006 | Sawada et al. |
| 7,133,782 B2 | 11/2006 | Odedra |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,323,305 B2 | 1/2008 | Leamon et al. |
| 7,335,762 B2 | 2/2008 | Rothberg et al. |
| 7,348,181 B2 | 3/2008 | Walt et al. |
| 7,424,371 B2 | 9/2008 | Kamentsky |
| 7,535,232 B2 | 5/2009 | Barbaro et al. |
| 7,575,865 B2 | 8/2009 | Leamon et al. |
| 7,645,596 B2 | 1/2010 | Williams et al. |
| 7,782,237 B2 | 8/2010 | Ronaghi et al. |
| 7,785,862 B2 | 8/2010 | Kim et al. |
| 7,835,871 B2 | 11/2010 | Kain et al. |
| 7,875,440 B2 | 1/2011 | Williams et al. |
| 7,948,015 B2 | 5/2011 | Rothberg et al. |
| 10,329,608 B2 * | 6/2019 | Hubbell ................. G16B 30/00 |
| 2003/0219797 A1 | 11/2003 | Zhao et al. |
| 2004/0018506 A1 | 1/2004 | Koehler et al. |
| 2004/0142330 A1 | 7/2004 | Nyren et al. |
| 2004/0197793 A1 | 10/2004 | Hassibi et al. |
| 2004/0197845 A1 | 10/2004 | Hassibi et al. |
| 2005/0084851 A1 | 4/2005 | Ronaghi et al. |
| 2006/0040297 A1 | 2/2006 | Leamon et al. |
| 2006/0147935 A1 | 7/2006 | Linnarsson |
| 2006/0147983 A1 | 7/2006 | O'uchi |
| 2007/0059733 A1 | 3/2007 | Sundara et al. |
| 2007/0059741 A1 | 3/2007 | Kamahori et al. |
| 2007/0092872 A1 | 4/2007 | Rothberg et al. |
| 2007/0207471 A1 | 9/2007 | Osaka et al. |
| 2007/0219367 A1 | 9/2007 | Shchepinov et al. |
| 2007/0281300 A1 | 12/2007 | Russell et al. |
| 2008/0166727 A1 | 7/2008 | Esfandyarpour et al. |
| 2008/0182757 A1 | 7/2008 | Heiner et al. |

(Continued)

FOREIGN PATENT DOCUMENTS

| | | |
|---|---|---|
| GB | 2461127 A | 12/2009 |
| WO | WO-9957321 A1 | 11/1999 |
| WO | WO-0101015 A1 | 1/2001 |
| WO | WO-0220837 A2 | 3/2002 |
| WO | WO-03020895 A2 | 3/2003 |
| WO | WO-2005040425 A2 | 5/2005 |
| WO | WO-2007098049 A2 | 8/2007 |
| WO | WO-2008076406 A2 | 6/2008 |
| WO | WO-2008092150 A1 | 7/2008 |
| WO | WO-2008092155 A2 | 7/2008 |
| WO | WO-2009158006 A2 | 12/2009 |

(Continued)

OTHER PUBLICATIONS

Shendure et al. "Next-generation DNA sequencing." Nature Biotechnology. 2008. vol. 26(10), pp. 1135-1145. (Year: 2008).*

(Continued)

*Primary Examiner* — John S Brusca
*Assistant Examiner* — Steven W. Bailey

(57) ABSTRACT

A method for sequencing a nucleic acid template includes: (a) performing a first sequencing process including flowing nucleotides and/or reagents to the nucleic acid template according to a first predetermined ordering of nucleotides and/or reagents to obtain a first sequencing result; (b) after the first sequencing process, performing a second sequencing process including flowing nucleotides and/or reagents to the nucleic acid template according to a second predetermined ordering of nucleotides and/or reagents to obtain a second sequencing result, the second predetermined ordering of nucleotides and/or reagents being different from the first predetermined ordering of nucleotides and/or reagents and at least one of the first and second predetermined orderings of nucleotides and/or reagents being designed for repeat sequencing; and (c) determining a sequence of bases corresponding to at least a portion of the nucleic acid template using both the first sequencing result and the second sequencing result.

19 Claims, 25 Drawing Sheets

(56) References Cited

U.S. PATENT DOCUMENTS

| | | |
|---|---|---|
| 2008/0286762 A1 | 11/2008 | Miyahara et al. |
| 2008/0286767 A1 | 11/2008 | Miyahara et al. |
| 2009/0024331 A1 | 1/2009 | Tomaney et al. |
| 2009/0026082 A1 | 1/2009 | Rothberg et al. |
| 2009/0053724 A1 | 2/2009 | Roth et al. |
| 2009/0105959 A1 | 4/2009 | Braverman et al. |
| 2009/0127589 A1 | 5/2009 | Rothberg et al. |
| 2009/0137404 A1 | 5/2009 | Drmanac et al. |
| 2009/0176200 A1 | 7/2009 | Wakita et al. |
| 2009/0305909 A1 | 12/2009 | Nordman et al. |
| 2009/0312188 A1 | 12/2009 | Duer et al. |
| 2010/0035252 A1 | 2/2010 | Rothberg et al. |
| 2010/0035253 A1 | 2/2010 | Gordon et al. |
| 2010/0088255 A1 | 4/2010 | Mann |
| 2010/0105052 A1 | 4/2010 | Drmanac et al. |
| 2010/0137143 A1 | 6/2010 | Rothberg et al. |
| 2010/0160172 A1 | 6/2010 | Erlich et al. |
| 2010/0173303 A1 | 7/2010 | Ronaghi et al. |
| 2010/0188073 A1 | 7/2010 | Rothberg et al. |
| 2010/0192032 A1 | 7/2010 | Chen et al. |
| 2010/0197507 A1 | 8/2010 | Rothberg et al. |
| 2010/0199155 A1 | 8/2010 | Kermani et al. |
| 2010/0209922 A1 | 8/2010 | Williams et al. |
| 2010/0267043 A1 | 10/2010 | Braverman et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304447 A1 | 12/2010 | Harris |
| 2010/0323348 A1 | 12/2010 | Hamady et al. |
| 2010/0323350 A1 | 12/2010 | Gordon et al. |
| 2011/0213563 A1 | 9/2011 | Chen et al. |
| 2011/0230358 A1 | 9/2011 | Rava |
| 2011/0246084 A1 | 10/2011 | Ronaghi et al. |
| 2011/0257889 A1 | 10/2011 | Klammer et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0294115 A1 | 12/2011 | Williams et al. |
| 2012/0035062 A1 | 2/2012 | Schultz et al. |
| 2012/0037961 A1 | 2/2012 | Rothberg et al. |
| 2012/0040844 A1 | 2/2012 | Rothberg et al. |
| 2012/0109598 A1 | 5/2012 | Davey et al. |
| 2012/0172241 A1 | 7/2012 | Rearick et al. |
| 2012/0173158 A1 | 7/2012 | Hubbell |
| 2012/0173159 A1 | 7/2012 | Davey et al. |
| 2012/0264621 A1 | 10/2012 | Hubbell et al. |
| 2012/0329042 A1 | 12/2012 | Beechem et al. |
| 2013/0060482 A1 | 3/2013 | Sikora et al. |
| 2013/0090860 A1 | 4/2013 | Sikora et al. |
| 2013/0172201 A1 | 7/2013 | Schultz et al. |
| 2013/0280702 A1 | 10/2013 | Schultz et al. |
| 2013/0303381 A1 | 11/2013 | Bortner et al. |
| 2014/0031238 A1 | 1/2014 | Schultz et al. |

FOREIGN PATENT DOCUMENTS

| | | |
|---|---|---|
| WO | WO-2010047804 A1 | 4/2010 |
| WO | WO-2010075188 A2 | 7/2010 |
| WO | WO-2010077859 A2 | 7/2010 |
| WO | WO-2010117804 A2 | 10/2010 |
| WO | WO-2010138182 A2 | 12/2010 |
| WO | WO-2011064319 A1 | 6/2011 |
| WO | WO-2011120964 A1 | 10/2011 |
| WO | WO-2011156707 A2 | 12/2011 |
| WO | WO-2012058459 A2 | 5/2012 |
| WO | WO-2012138921 A1 | 10/2012 |

OTHER PUBLICATIONS

Ahmadian et al., "Single-nucleotide polymorphism analysis by pyrosequencing", Analytical and Biochemistry, vol. 280, 2000, pp. 103-110.

Ahmadian et al., "Pyrosequencing: History, biochemistry and future," Clinica Chimica Acta, 363:83-94 (2006).

Aksyonov et al., "Multiplexed DNA sequencing-by-synthesis," Anal. Biochem., 348:127-138 (2006).

Anderson et al., "A system for multiplexed direct electrical detection of DNA synthesis", Sensors and Actuators B: Chemical, vol. 129, No. 1, Jan. 2008, pp. 79-86.

Balzer et al., "Characteristics of 454 pyrosequencing data-enabling realistic simulation with flowsim," Bioinformatics, 26:i420-i425 (2010).

Berger et al., "Compact, universal DNA microarrays to comprehensively determine transcriptionfactor binding site specificities," Nat. Biotechnol., 24(11):1429-1435 (2006).

Berstel et al., "The origins of combinatorics on words," Eur. J. Combin., 28(3):996-1022 (2007).

Brockman et al., "Quality scores and SNP detection in sequencing-by-synthesis systems," Genome Research, 18:763-770 (2008).

Chapter 2, "Machine-Learning Foundations: The Probabilistic Framework", In: Baldi, P. and Brunak, S., "Bioinformatics: The Machine Learning Approach, 2"d Edition, The MIT Press, 47-65 (2001).

De Bruijn, N.G., "Ackowledgement of priority to C. Flye Sainte-Marie on the counting of circular arrangements of $2.\sup.n$ zeros and ones that show each n-letter word exactly once," T.H.-Report 75-WSK-06, Technological University Eindhoven (1975).

Droege et al., "The Genome Sequencer FLX ™ System-Longer reads, more applications, straight forward bioinformatics and more complete data sets," J. Biotechnol., 136:3-10 (2008).

Elahi et al., "Pyrosequencing: A Tool for DNA Sequencing Analysis," in Zhao, S. & Stodolsky, M., Eds., Methods in Molecular Biology, vol. 255, Humana Press Inc., pp. 211-219.

Fakhrai-Rad et al., "Pyrosequencing™: An Accurate Detection Platform for Single Nucleotide Polymorphisms," Hum. Mutat., 19:479-485 (2002).

Finotello et al., "Comparative analysis of algorithms for whole-genome assembly of pyrosequencing data," Briefings in Bioinformatics Advance Access, 1-12 (Oct. 21, 2011).

Fuller et al., "The challenges of sequencing by synthesis", Nature Biotechnology, vol. 27, No. 11, Nov. 2009, 1013-1023.

Garcia et al., "Mutation detection by pyrosequencing: sequencing of exons 5-8 of the p53 tumor suppressor gene," Gene, 253(2):249-257 (2000) (see whole document, including Fig. 4).

Guarizadeh, B., "Method Development and Applications of Pyrosequencing Technology," Doctoral Dissertation, Royal Institute of Technology, Stockholm, Sweden (2003).

Hert et al., "Advantages and limitations of next-generation sequencing technologies: a comparison of electrophoresis and non-electrophoresis methods," Electroghoresis, 29(23):4618-26 (2008).

Huse et al., "Accuracy and quality of massively parallel DNA pyrosequencing," Genome Biology, 8(7):R143.1-R143.9 (2007).

Ji et al., "BM-BC: A Bayesian method of base calling for Solexa sequence data," Department of Biostatistics, The University of Texas M. D. Anderson Cancer Center, Houston, Texas, U.S.A. (http://odin.mdacc.tmc.edu/-ylii/BMBC/bmbc-ie2.pdf), 1-27, 2010.

Langaee et al., "Genetic variation analyses by Pyrosequencing," Mutation Research, 573: 96-102 (2005).

Leamon et al., "Cramming More Sequencing Reactions onto Microreactor Chips", Chemical Reviews, vol. 107, No. 8, Aug. 2007, pp. 3367-3376.

Ledergerber et al., "Base-calling for next-generation sequencing platforms," Briefings in Bioinformatics Advance Access, 12(5):489-497 (Jan. 18, 2011).

Margulies et al., "Genome Sequencing in Microfabricated High-Density Picolitre Reactors", Nature, vol. 437, No. 15, 2005, pp. 376-380.

Margulies et al., "Supplemental Materials, Genome Sequencing in Microfabricated High-Density Picolitre Reactors", Nature, vol. 437, No. 15, 2005, pp. 1-34.

Massingham et al., "All Your Base: a fast and accurate probabilistic approach to base calling," Euroclean Bioinformatics Institute, Wellcome Trust Genome Cam12us, Hinxton, Cambridgeshire, UK (http://www.ebi.ac.uk/goldman-srv/AYB/references/ayb_revised.pdf), Oct. 26, 2011, 1-26.

(56) References Cited

OTHER PUBLICATIONS

Metzker, "Emerging technologies in DNA sequencing," Genome Research, 15:1767-1776 (2005).
Metzker, "Sequencing technologies—The next generation," Nature Reviews Genetics, vol. 11, No. 1, Jan. 2010, pp. 31-46.
Pourmand et al., "Direct electrical detection of DNA synthesis", Proceedings of the National Academy of Sciences, vol. 103, No. 17, Apr. 2006, pp. 6466-6470.
Pourmand et al., "Multiplex Pyrosequencing," Nucleic Acids Res., 30(7)(e31):1-5 (2002).
Ronaghi et al. (2002) Discovery of single nucleotide polymorphisms and mutations by pyrosequencing. Comparative and Functional Genomics, 3:51-56.
Ronaghi et al., "A Sequencing Method Based on Real-Time Pyrophosphate", Science, vol. 281, No. 5375, Jul. 1998, pp. 363-365.
Ronaghi, "Pyrosequencing Sheds Light on DNA Sequencing," Genome Research, 11:3-11 (2001).
Specification & Drawings of U.S. Appl. No. 61/198,222, filed Nov. 4, 2008.
Svantesson et al., "A mathematical model of the Pyrosequencing reaction system," Biophysical Chemistry, 100:129-145 (2004).
U.S. Appl. No. 61/198,222, filed Nov. 4, 2008, Appendix to the Specification of U.S. Appl. No. 61/198,222, filed Nov. 4, 2008, 50 pages.
Van Aardenne-Ehrenfest, T. et al., "Circuits and Trees in Oriented Linear Graphs", Simon Stevin 28:, 1951,203-217.

* cited by examiner

FIG. 9A
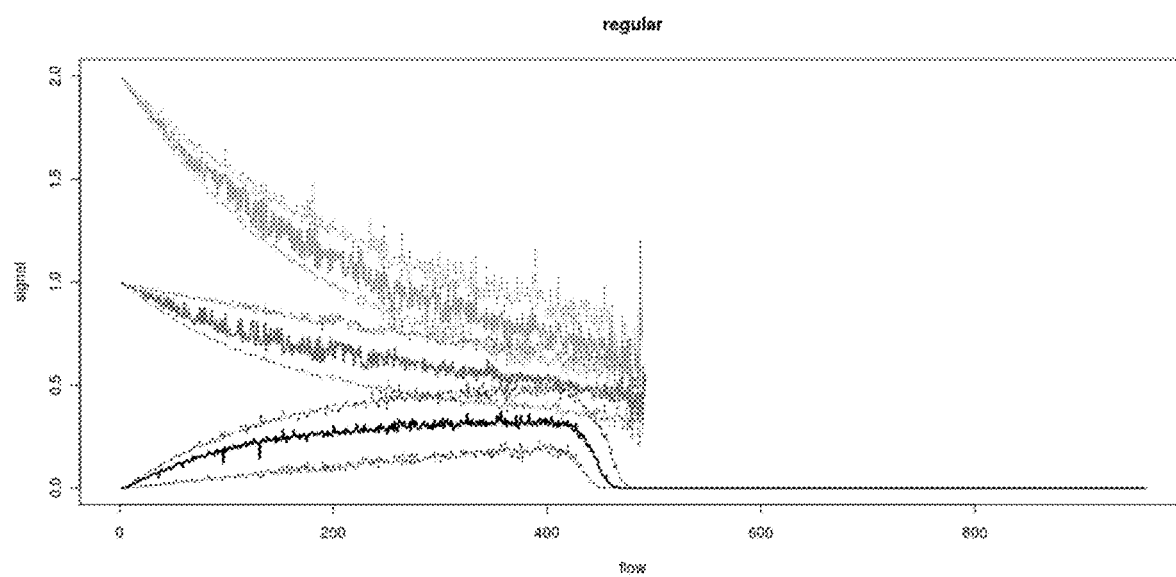
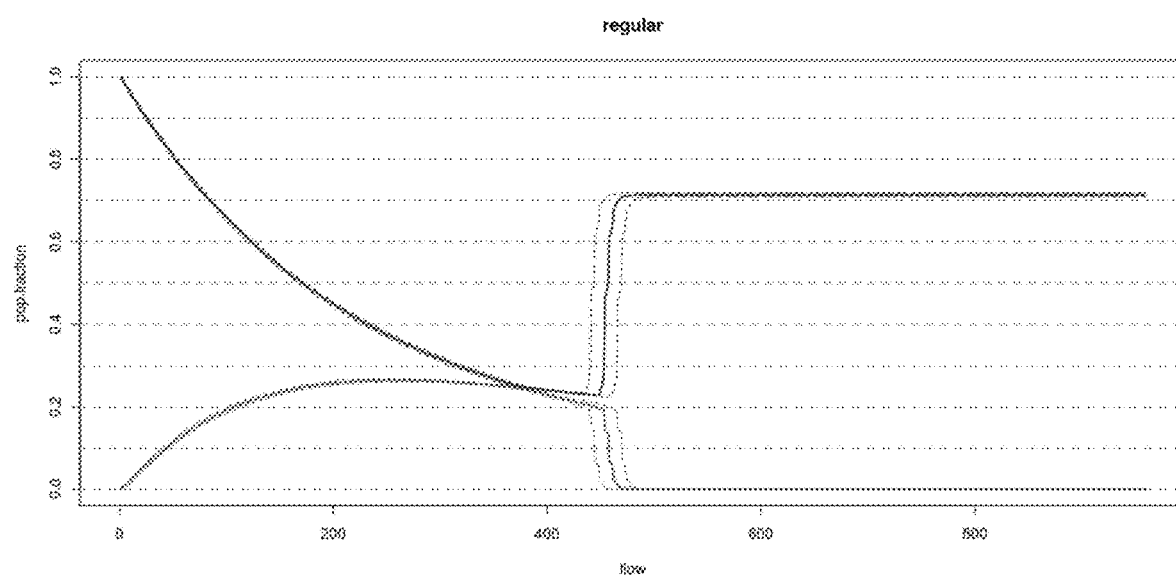
FIG. 9B

FIG. 10A
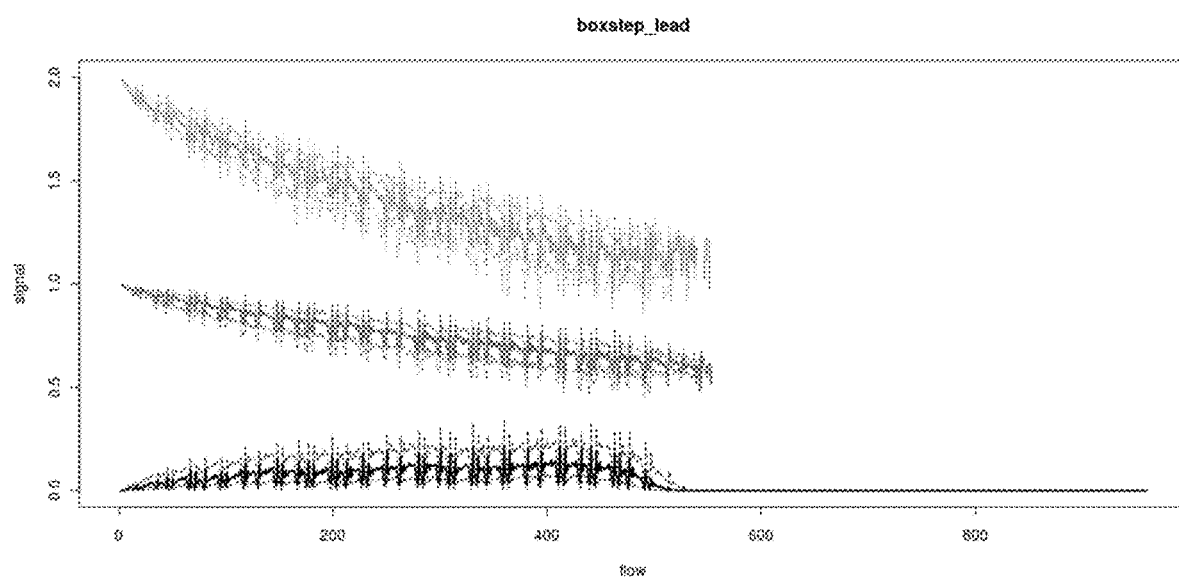
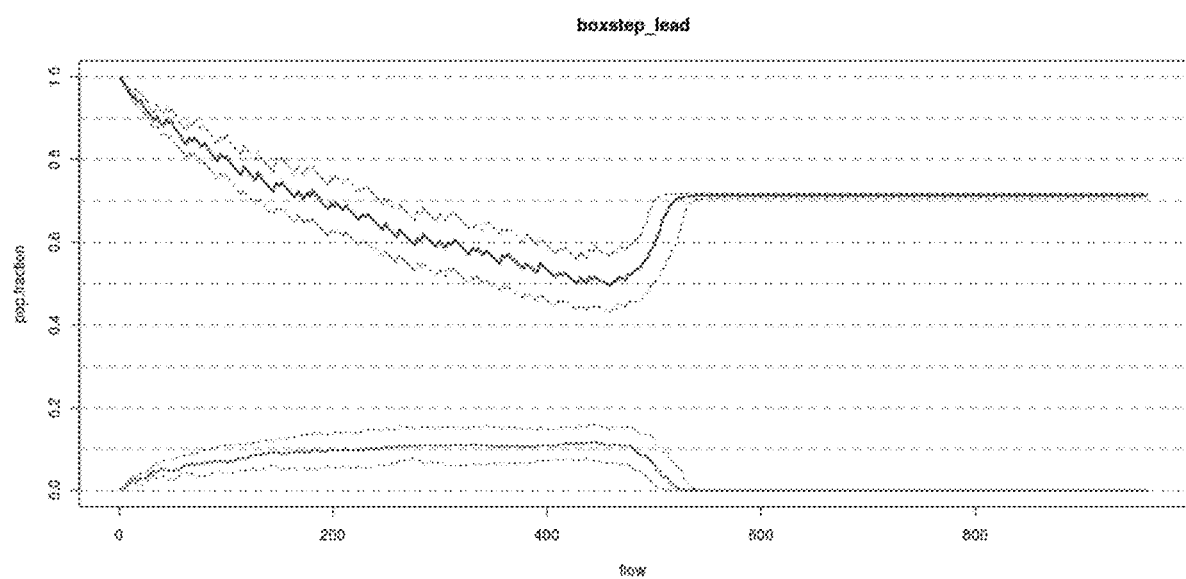
FIG. 10B

FIG. 11A
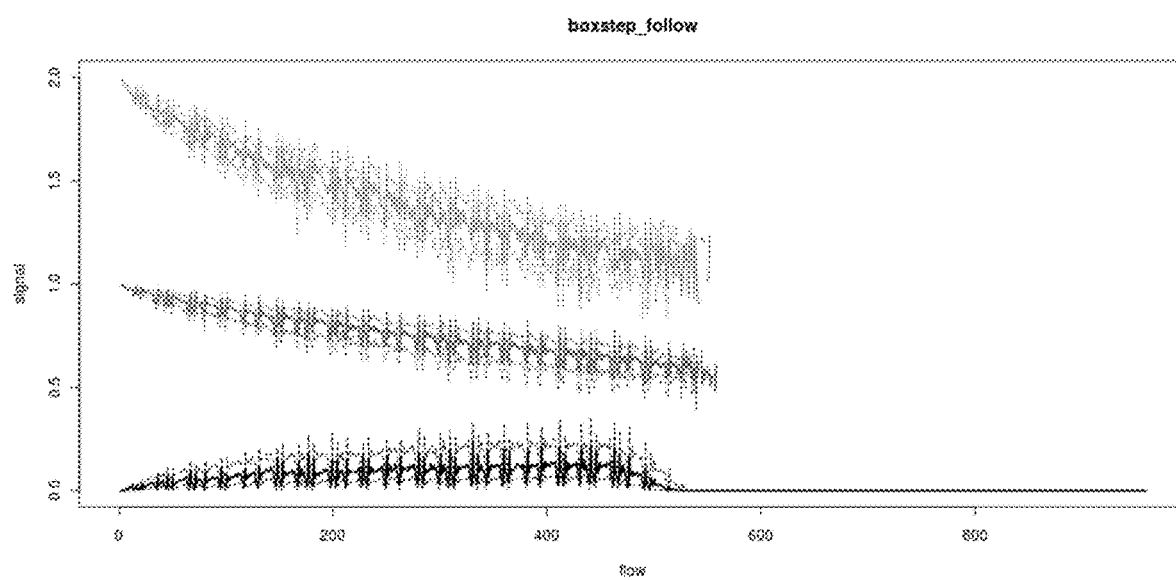
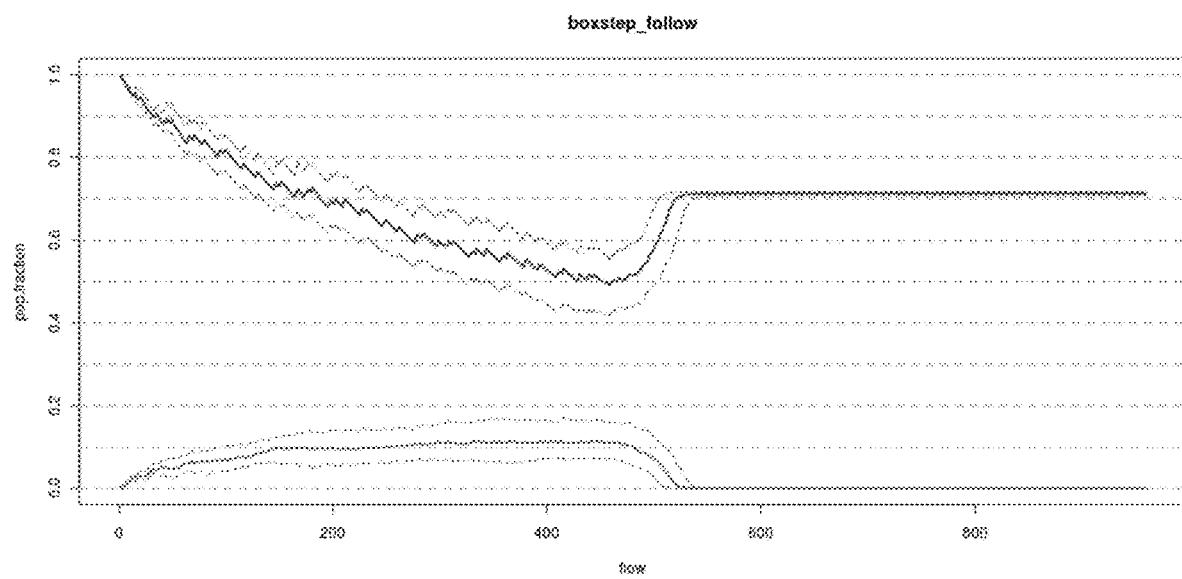
FIG. 11B

METHODS, SYSTEMS, AND COMPUTER READABLE MEDIA FOR REPEAT SEQUENCING

CROSS-REFERENCE TO RELATED APPLICATIONS

This application is a continuation of U.S. application Ser. No. 14/048,843 filed Oct. 8, 2013, and claims priority to U.S. application No. 61/712,686 filed Oct. 11, 2012, and U.S. application No. 61/712,206 filed Oct. 10, 2012, which disclosures are herein incorporated by reference in their entirety.

FIELD

This application generally relates to methods, systems, and computer readable media for nucleic acid sequencing, and, more specifically, to methods, systems, and computer readable media for performing repeat sequencing.

BACKGROUND

Various instruments, apparatuses, and/or systems perform sequencing of nucleic acids using sequencing-by-synthesis, including, for example, the Genome Analyzer/HiSeq/MiSeq platforms (Illumina, Inc.; see, e.g., U.S. Pat. Nos. 6,833,246 and 5,750,341); the GS FLX, GS FLX Titanium, and GS Junior platforms (Roche/454 Life Sciences; see, e.g., Ronaghi et al., SCIENCE, 281:363-365 (1998), and Margulies et al., NATURE, 437:376-380 (2005)); and the Ion Personal Genome Machine (PGM™) and Ion Proton™ (Life Technologies Corp./Ion Torrent; see, e.g., U.S. Pat. No. 7,948,015 and U.S. Pat. Appl. Publ. Nos. 2010/0137143, 2009/0026082, and 2010/0282617, which are all incorporated by reference herein in their entirety). There is a need for new methods, systems, and computer readable media that reduce sequencing errors in sequencing-by-synthesis or other sequencing approaches.

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

FIGS. 9A and 9B illustrate exemplary simulation data corresponding to signal response curves for a cyclical, repeating flow ordering of "TACG TACG . . . ."

FIGS. 10A and 10B illustrate exemplary simulation data corresponding to signal response curves for a BOXSTEP_LEAD flow ordering.

FIGS. 11A and 11B illustrate exemplary simulation data corresponding to signal response curves for a BOXSTEP_FOLLOW flow ordering.

SUMMARY

Figure 1:
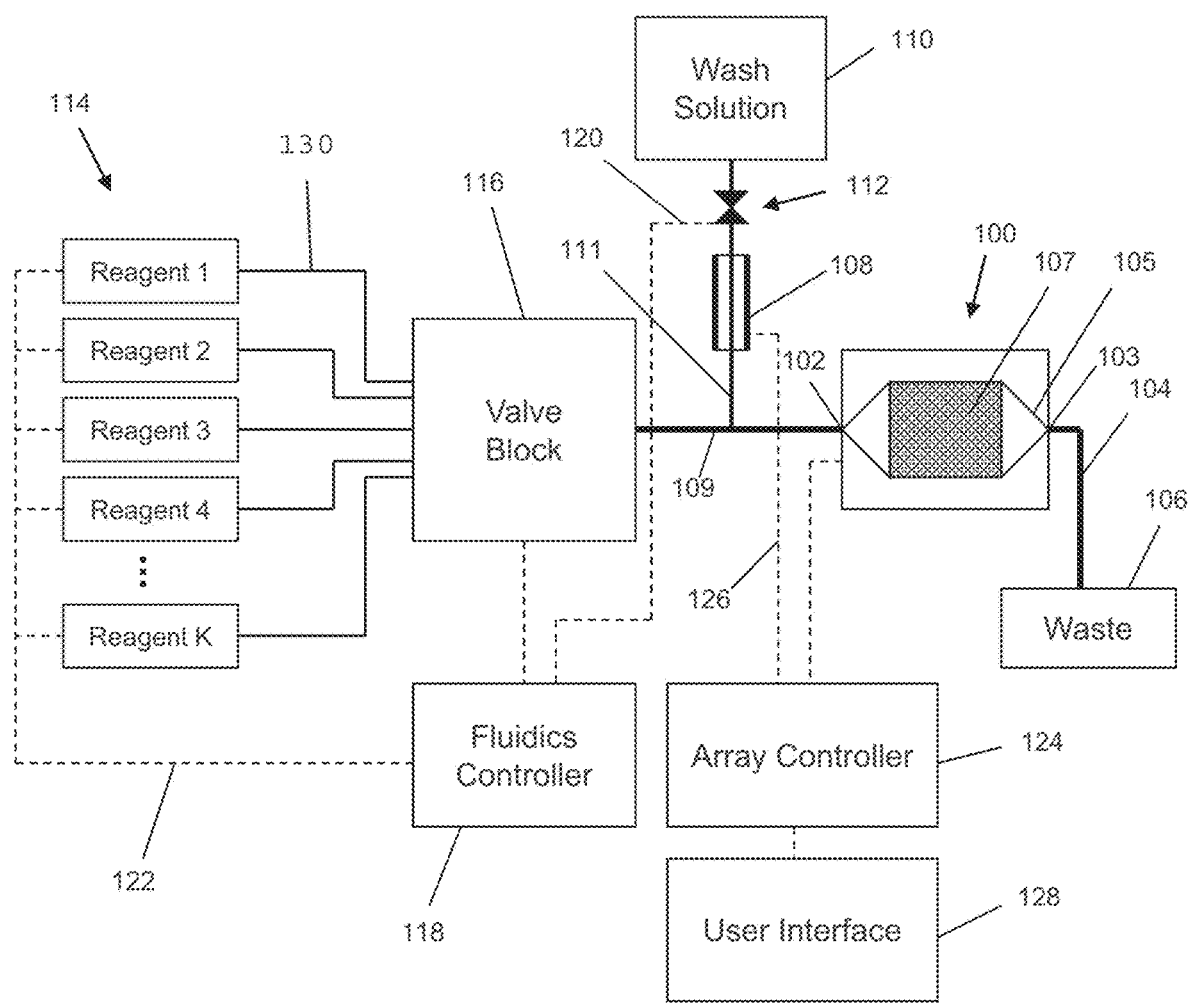
FIG. 1 illustrates components of an exemplary system for nucleic acid sequencing.

According to an exemplary embodiment, there is provided a method for sequencing a nucleic acid template, including: performing a first sequencing process on the nucleic acid template to obtain a first sequencing result, wherein the first sequencing process includes flowing nucleotides and/or reagents to the nucleic acid template according to a first predetermined ordering of nucleotides and/or reagents; after the first sequencing process, performing a second sequencing process on the nucleic acid template to obtain a second sequencing result, wherein the second sequencing process includes flowing nucleotides and/or reagents to the nucleic acid template according to a second predetermined ordering of nucleotides and/or reagents, wherein the second predetermined ordering of nucleotides and/or reagents is different from the first predetermined ordering of nucleotides and/or reagents and wherein at least one of the first and second predetermined orderings of nucleotides and/or reagents is designed for repeat sequencing; and determining a sequence of bases corresponding to at least a portion of the nucleic acid template using both the first sequencing result and the second sequencing result.

According to an exemplary embodiment, there is provided a system for sequencing a nucleic acid template, including: a machine-readable memory; and a processor configured to execute machine-readable instructions, which, when executed by the processor, cause the system to perform a method including: performing a first sequencing process on the nucleic acid template to obtain a first sequencing result, wherein the first sequencing process includes flowing nucleotides and/or reagents to the nucleic acid template according to a first predetermined ordering of nucleotides and/or reagents; after the first sequencing process, performing a second sequencing process on the nucleic acid template to obtain a second sequencing result, wherein the second sequencing process includes flowing nucleotides and/or reagents to the nucleic acid template according to a second predetermined ordering of nucleotides and/or reagents, wherein the second predetermined ordering of nucleotides and/or reagents is different from the first predetermined ordering of nucleotides and/or reagents and wherein at least one of the first and second predetermined orderings of nucleotides and/or reagents is designed for repeat sequencing; and determining a sequence of bases corresponding to at least a portion of the nucleic acid template using both the first sequencing result and the second sequencing result.

According to an exemplary embodiment, there is provided a non-transitory machine-readable storage medium comprising instructions which, when executed by a processor, cause the processor to perform a method for nucleic acid sequencing including: performing a first sequencing process on the nucleic acid template to obtain a first sequencing result, wherein the first sequencing process includes flowing nucleotides and/or reagents to the nucleic acid template according to a first predetermined ordering of nucleotides and/or reagents; after the first sequencing process, performing a second sequencing process on the nucleic acid template to obtain a second sequencing result, wherein the second sequencing process includes flowing nucleotides and/or reagents to the nucleic acid template according to a second predetermined ordering of nucleotides and/or reagents, wherein the second predetermined ordering of nucleotides and/or reagents is different from the first predetermined ordering of nucleotides and/or reagents and wherein at least one of the first and second predetermined orderings of nucleotides and/or reagents is designed for repeat sequencing; and determining a sequence of bases corresponding to at least a portion of the nucleic acid template using both the first sequencing result and the second sequencing result.

EXEMPLARY EMBODIMENTS

The following description and the various embodiments described herein are exemplary and explanatory only and are not to be construed as limiting or restrictive in any way. Other embodiments, features, objects, and advantages of the present teachings will be apparent from the description and accompanying drawings, and from the claims.

Unless otherwise specifically designated herein, terms, techniques, and symbols of biochemistry, cell biology, genetics, molecular biology, nucleic acid chemistry, nucleic acid sequencing, and organic chemistry used herein follow those of standard treatises and texts in the relevant field. See, e.g., Kornberg and Baker, DNA REPLICATION, 2nd ed. (W.H. Freeman, New York, 1992); Lehninger, BIOCHEMISTRY, 2nd ed. (Worth Publishers, New York, 1975); Strachan and Read, HUMAN MOLECULAR GENETICS, 2nd ed. (Wiley-Liss, New York, 1999); Birren et al. (eds.), GENOME ANALYSIS: A LABORATORY MANUAL SERIES (Vols. I-IV), Dieffenbach and Dveksler (eds.), PCR PRIMER: A LABORATORY MANUAL, and Green and Sambrook (eds.), MOLECULAR CLONING: A LABORATORY MANUAL (all from Cold Spring Harbor Laboratory Press); and Hermanson, BIOCONJUGATE TECHNIQUES, 2nd ed. (Academic Press, 2008).

In this application, "defined space" (or "reaction space," which may be used interchangeably with "defined space") generally refers to any space (which may be in one, two, or three dimensions) in which at least some of a molecule, fluid, and/or solid can be confined, retained and/or localized. The space may be a predetermined area (which may be a flat area) or volume, and may be defined, for example, by a depression or a micro-machined well in or associated with a microwell plate, microtiter plate, microplate, or a chip, or by isolated hydrophobic areas on a generally hydrophobic surface. In an embodiment, a defined space may be a reaction chamber, such as a well or a microwell, which may be in a chip. In an embodiment, a defined space may be a substantially flat area on a substrate without wells.

In this application, "reaction confinement region" generally refers to any region in which a reaction may be confined and includes, for example, a "reaction chamber," a "well," and a "microwell" (each of which may be used interchangeably). A reaction confinement region may include a region in which a physical or chemical attribute of a solid substrate can permit the localization of a reaction of interest, and a discrete region of a surface of a substrate that can specifically bind an analyte of interest, for example. Reaction confinement regions may be hollow or have well-defined shapes and volumes, and may be manufactured into a substrate using any suitable microfabrication techniques and have any suitable volume, shape, aspect ratio, and other dimensional characteristics. Reaction confinement regions may also be substantially flat areas on a substrate without wells. Various exemplary configurations of microwells or reaction chambers are disclosed in Rothberg et al., U.S. Pat. Publ. Nos. 2009/0127589 and 2009/0026082; and Rothberg et al., U.K. Pat. Appl. Publ. No. GB 2461127, which are all incorporated by reference herein in their entirety.

Defined spaces or reaction confinement regions may be arranged as an array, which may be a substantially planar one-dimensional or two-dimensional arrangement of elements such as sensors or wells. The number of columns (or rows) of a two-dimensional array may or may not be the same. Preferably, the array comprises at least 100,000 chambers. Preferably, each reaction chamber has a horizontal width and a vertical depth that has an aspect ratio of about 1:1 or less. Preferably, the pitch between the reaction chambers is no more than about 10 microns, or no more than about 5 microns, or no more than about 1 micron, or no more than about 0.5 microns. Preferably, a volume of each reaction chamber is no greater than 10 $\mu m^3$ (i.e., 1 pL), or no greater than 0.34 pL, and more preferably no greater than 0.096 pL or even 0.012 pL. A reaction chamber may be $2^2$, $3^2$, $4^2$, $5^2$, $6^2$, $7^2$, $8^2$, $9^2$, or $10^2$ square microns in cross-sectional area at the top, for example. Preferably, the array may have at least $10^2$, $10^3$, $10^4$, $10^5$, $10^6$, $10^7$, $10^8$, $10^9$, or more reaction chambers, for example. Microwells may have any polygonal cross sections, including square, rectangular, or octagonal cross sections, for example, and may be arranged as a rectilinear or hexagonal array on a surface.

Defined spaces or reaction confinement regions, whether arranged as an array or in some other configuration, may be in electrical communication with at least one sensor to allow detection or measurement of one or more detectable or measurable parameter or characteristics. The sensors may convert changes in the presence, concentration, or amounts of reaction by-products (or changes in ionic character of reactants) into an output signal, which may be registered electronically, for example, as a change in a voltage level or a current level which, in turn, may be processed to extract information about a chemical reaction or desired association event, for example, a nucleotide incorporation event. The sensors may include at least one ion sensitive field effect transistor ("ISFET") or chemically sensitive field effect transistor ("chemFET") that can be configured to generate at least one output signal related to a property of a chemical reaction or target analyte of interest in proximity thereof. Such properties can include a concentration (or a change in concentration) of a reactant, product or by-product, or a value of a physical property (or a change in such value), such as an ion concentration. An initial measurement or interrogation of a pH for a defined space or reaction confinement region, for example, may be represented as an electrical signal or a voltage, which may be digitalized (e.g., converted to a digital representation of the electrical signal or the voltage).

In various embodiments, the methods, systems, and computer readable media described herein may advantageously be used to determine the sequence and/or identity of one or more nucleic acid samples using sequencing-by-synthesis. In sequencing-by-synthesis, the sequence of a target nucleic acid may be determined by the stepwise synthesis of complementary nucleic acid strands on a target nucleic acid serving as a template for the sequencing-by-synthesis reactions. During sequencing-by-synthesis, nucleotides may be sequentially added to growing polynucleotide molecules or strands at positions complementary to template polynucleotide molecules or strands. The addition of the nucleotides to the growing complementary strands, which may be detected using a variety of methods (e.g., pyrosequencing, fluorescence detection, and label-free electronic detection), may be used to identify the sequence composition of the template nucleic acid. This process may be iterated until a complete or selected sequence length complementary to the template has been synthesized.

In various embodiments, the methods, systems, and computer readable media described herein may advantageously be used to generate, process, and/or analyze data and signals obtained using electronic or charged-based nucleic acid sequencing. In electronic or charged-based sequencing (such as, e.g., pH-based sequencing), a nucleotide incorporation event may be determined by detecting ions (e.g., hydrogen ions) generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc.

FIG. 1 illustrates components of an exemplary system for nucleic acid sequencing. The components include a flow cell and sensor array 100, a reference electrode 108, a plurality of reagents 114, a valve block 116, a wash solution 110, a valve 112, a fluidics controller 118, lines 120/122/126, passages 104/109/111, a waste container 106, an array controller 124, and a user interface 128. The flow cell and sensor array 100 includes an inlet 102, an outlet 103, a microwell array 107, and a flow chamber 105 defining a flow path of reagents over the microwell array 107. The reference electrode 108 may be of any suitable type or shape, including a concentric cylinder with a fluid passage or a wire inserted into a lumen of passage 111. The reagents 114 may be driven through the fluid pathways, valves, and flow cell by pumps, gas pressure, or other suitable methods, and may be discarded into the waste container 106 after exiting the flow cell and sensor array 100. The reagents 114 may, for example, contain dNTPs to be flowed through passages 130 and through the valve block 116, which may control the flow of the reagents 114 to flow chamber 105 (also referred to herein as a reaction chamber) via passage 109. The system may include a reservoir 110 for containing a wash solution that may be used to wash away dNTPs, for example, that may have previously been flowed. The microwell array 107 may include an array of defined spaces or reaction confinement regions, such as microwells, for example, that is operationally associated with a sensor array so that, for example, each microwell has a sensor suitable for detecting an analyte or reaction property of interest. The microwell array 107 may preferably be integrated with the sensor array as a single device or chip. The flow cell may have a variety of designs for controlling the path and flow rate of reagents over the microwell array 107, and may be a microfluidics device. The array controller 124 may provide bias voltages and timing and control signals to the sensor, and collect and/or process output signals. The user interface 128 may display information from the flow cell and sensor array 100 as well as instrument settings and controls, and allow a user to enter or set instrument settings and controls. The system may be configured to let a single fluid or reagent contact the reference electrode 108 throughout an entire multi-step reaction. The valve 112 may be shut to prevent any wash solution 110 from flowing into passage 109 as the reagents are flowing. Although the flow of wash solution may be stopped, there may still be uninterrupted fluid and electrical communication between the reference electrode 108, passage 109, and the sensor array 107. The distance between the reference electrode 108 and the junction between passages 109 and 111 may be selected so that little or no amount of the reagents flowing in passage 109 and possibly diffusing into passage 111 reach the reference electrode 108. In an embodiment, the wash solution 110 may be selected as being in continuous contact with the reference electrode 108, which may be especially useful for multi-step reactions using frequent wash steps.

In various embodiments, the fluidics controller 118 may be programmed to control driving forces for flowing reagents 114 and the operation of valve 112 and valve block 116 with any suitable instrument control software, such as LabView (National Instruments, Austin, Tex.), to deliver reagents to the flow cell and sensor array 100 according to a predetermined reagent flow ordering. The reagents may be delivered for predetermined durations, at predetermined flow rates, and may measure physical and/or chemical parameters providing information about the status of one or more reactions taking place in defined spaces or reaction confinement regions. The predetermined ordering may be based on a cyclical, repeating pattern consisting of consecutive repeats of a short pre-determined reagent flow ordering (e.g., consecutive repeats of pre-determined sequence of four nucleotide reagents such as, for example, "ACTG ACTG . . . "), may be based in whole or in part on some other pattern of reagent flows (such as, e.g., any of the various reagent flow orderings discussed herein and/or in Hubbell et al., U.S. Pat. Appl. Publ. No. 2012/0264621, published Oct. 18, 2012, which is incorporated by reference herein in its entirety), and may also be based on some combination thereof.

Figure 2A:
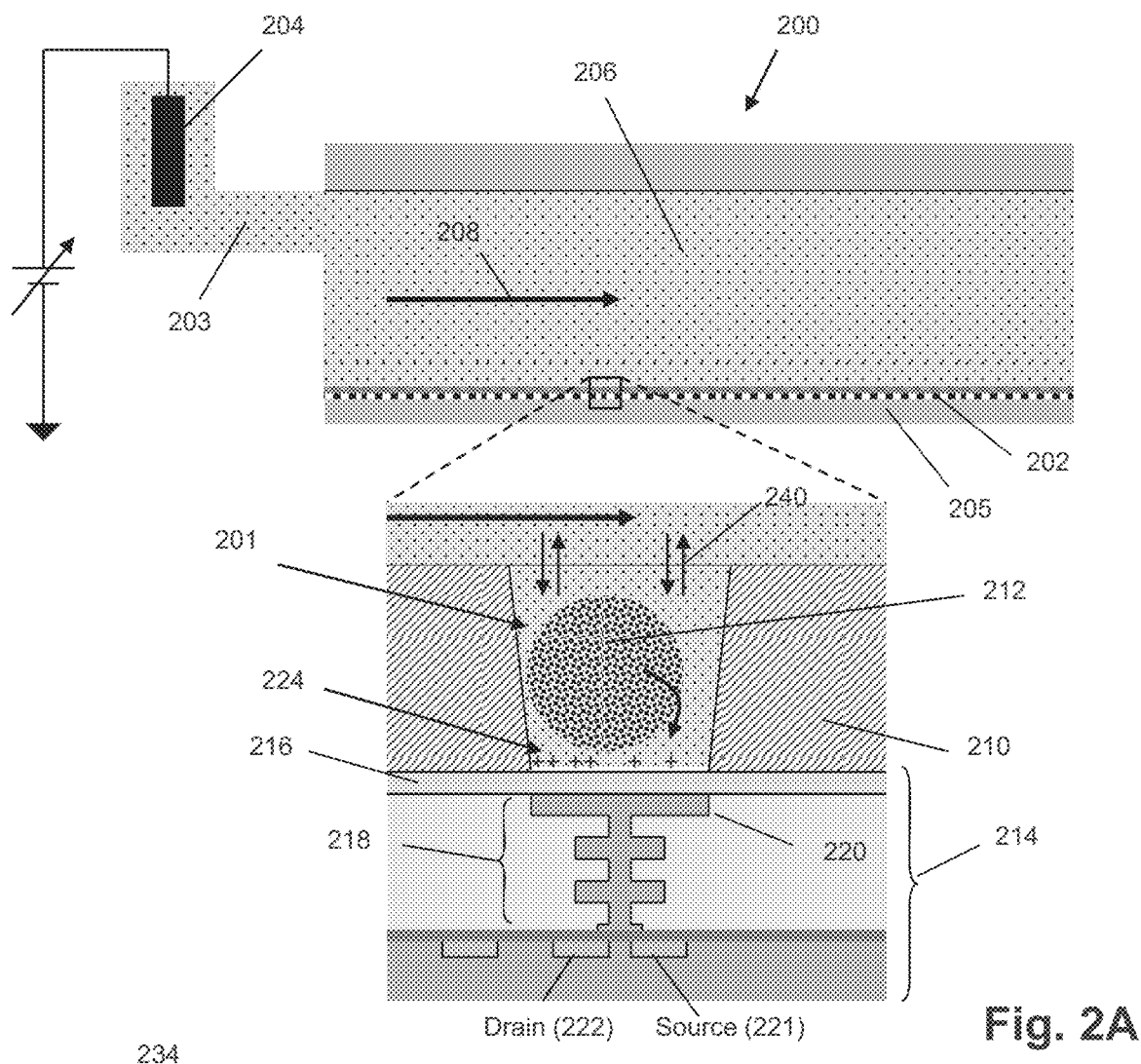
FIG. 2A illustrates views of an exemplary flow cell for nucleic acid sequencing.

FIG. 2A illustrates cross-sectional and expanded views of an exemplary flow cell 200 for nucleic acid sequencing. The flow cell 200 includes a microwell array 202, a sensor array 205, and a flow chamber 206 in which a reagent flow 208 may move across a surface of the microwell array 202, over open ends of microwells in the microwell array 202. The flow of reagents (e.g., nucleotide species) can be provided in any suitable manner, including delivery by pipettes, or through tubes or passages connected to a flow chamber. The duration, concentration, and/or other flow parameters may be the same or different for each reagent flow. Likewise, the duration, composition, and/or concentration for each wash flow may be the same or different. A microwell 201 in the microwell array 202 may have any suitable volume, shape, and aspect ratio, which may be selected depending on one or more of any reagents, by-products, and labeling techniques used, and the microwell 201 may be formed in layer 210, for example, using any suitable microfabrication technique. A sensor 214 in the sensor array 205 may be an ISFET or a chemFET sensor with a floating gate 218 having a sensor plate 220 separated from the microwell interior by a passivation layer 216, and may be predominantly responsive to (and generate an output signal related to) an amount of charge 224 present on the passivation layer 216 opposite of the sensor plate 220. Changes in the amount of charge 224 cause changes in the current between a source 221 and a drain 222 of the sensor 214, which may be used directly to provide a current-based output signal or indirectly with additional circuitry to provide a voltage output signal. Reactants, wash solutions, and other reagents may move into microwells primarily by diffusion 240. One or more analytical reactions to identify or determine characteristics or properties of an analyte of interest may be carried out in one or more microwells of the microwell array 202. Such reactions may generate directly or indirectly by-products that affect the amount of charge 224 adjacent to the sensor plate 220. In an embodiment, a reference electrode 204 may be fluidly connected to the flow chamber 206 via a flow passage 203. In an embodiment, the microwell array 202 and the sensor array 205 may together form an integrated unit forming a bottom wall or floor of the flow cell 200. In an embodiment, one or more copies of an analyte may be attached to a solid phase support 212, which may include microparticles, nanoparticles, beads, gels, and may be solid and porous, for example. The analyte may include one or more copies of a nucleic acid analyte obtained using any suitable technique.

Figure 2B:
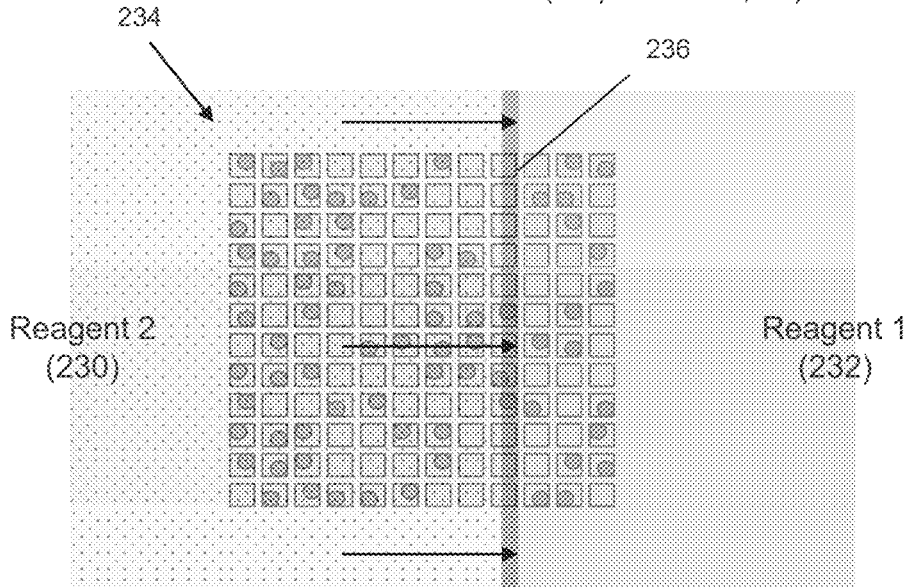
FIG. 2B illustrates an exemplary uniform flow front between reagents flows.

FIG. 2B illustrates an exemplary uniform flow front between reagents moving across a section 234 of an exemplary microwell array. A "uniform flow front" between first reagent 232 and second reagent 230 generally refers to the reagents undergoing little or no mixing as they move, thereby keeping a boundary 236 between them narrow. The boundary may be linear for flow cells having inlets and outlets at opposite ends of their flow chambers, or it may be curvilinear for flow cells having central inlets (or outlets) and peripheral outlets (or inlets).

Figure 3A:
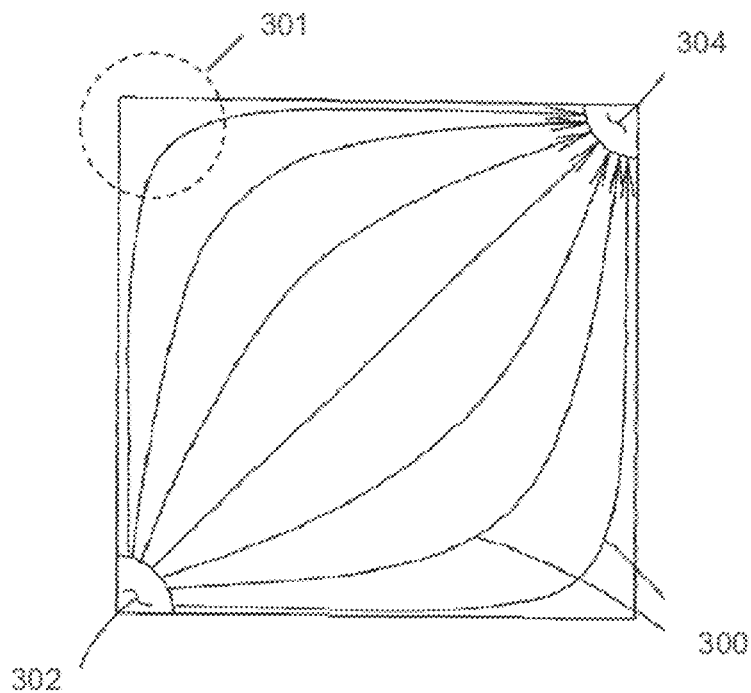
FIG. 3A illustrates exemplary flow paths through an exemplary flow chamber.

FIG. 3A illustrates exemplary flow paths through a flow chamber having diagonally opposed inlet and outlet. The reagents may follow flow paths 300 as they transit along a diagonal axis of the flow chamber between an inlet 302 and an outlet 304, which paths may not reach all the way to corner 301, for example.

Figure 3B:
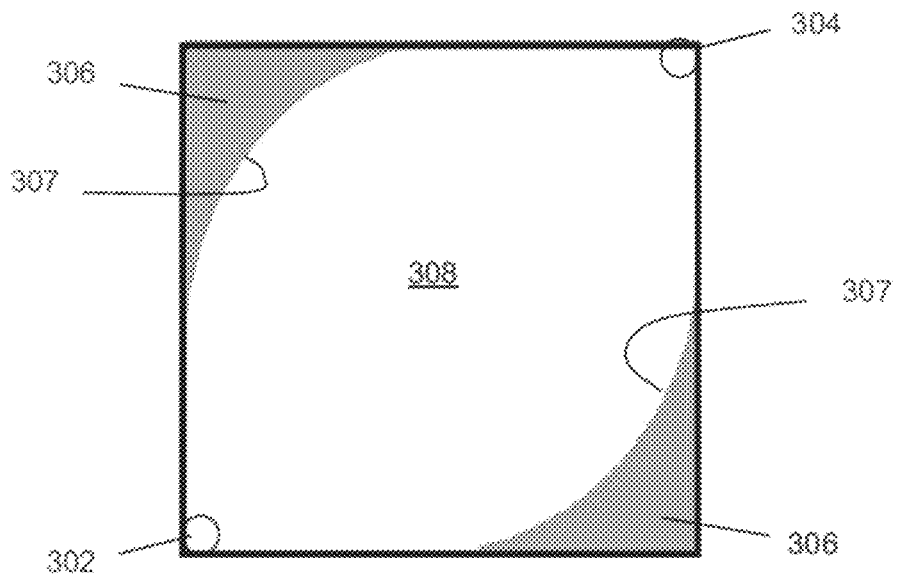
FIG. 3B illustrates an exemplary flow chamber with an exemplary sensor array area.

FIG. 3B illustrates an exemplary flow chamber 308 with an exemplary sensor array area defined by reference to a reach of reagent flow paths. The flow chamber may include an area covered by the reagents as they transit from inlet 302 to outlet 304 (excluding an area 306 outside the boundary 307 that delimits an extent of the reagent flow reach in the flow chamber), which area may be used to locate microwells.

Figure 4:
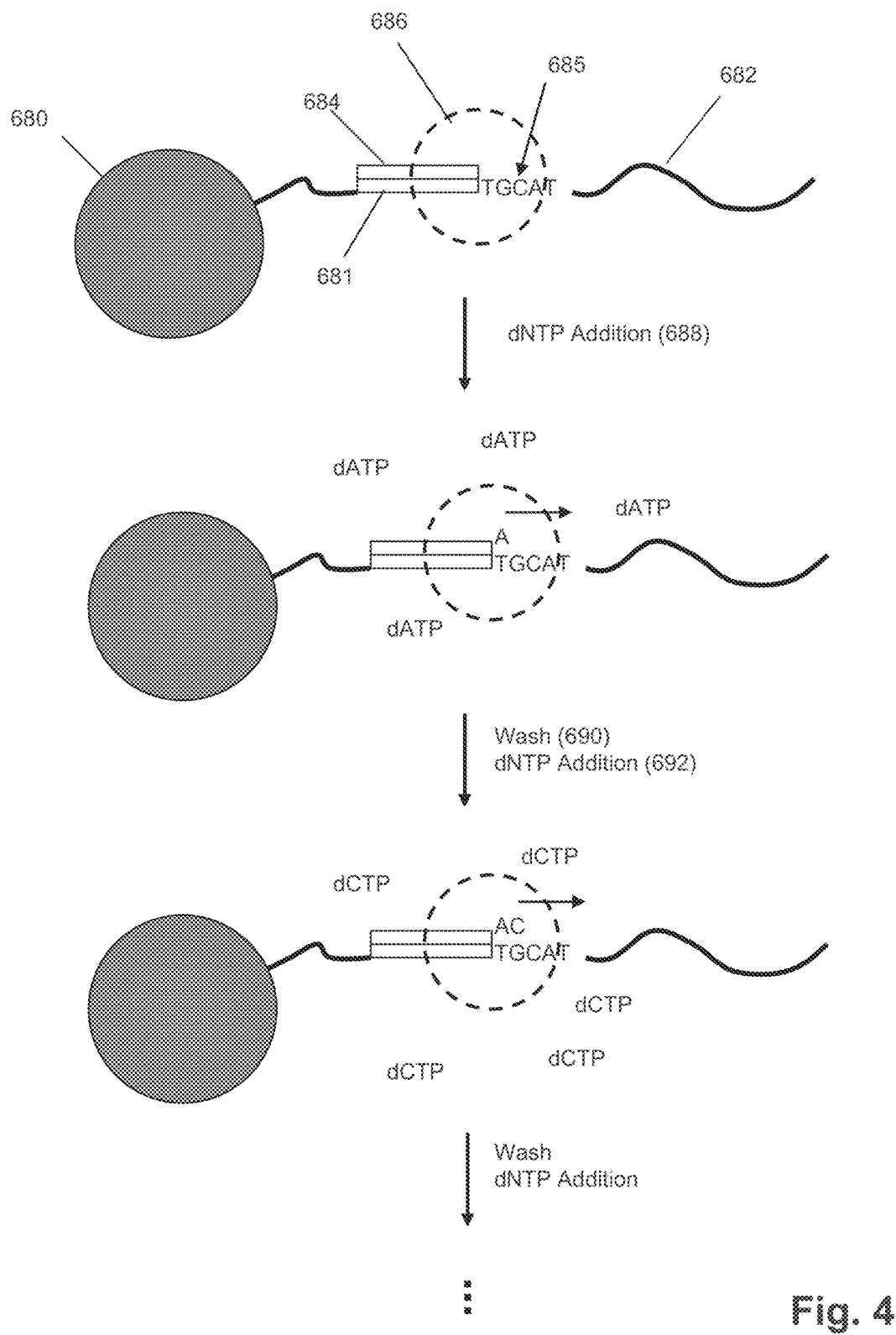
FIG. 4 illustrates an exemplary process for label-free, pH-based sequencing.

FIG. 4 illustrates an exemplary process for label-free, pH-based sequencing. A template 682 with sequence 685 and a primer binding site 681 are attached to a solid phase support 680. The template 682 may be attached as a clonal population to a solid support, such as a microparticle or bead, for example, and may be prepared as disclosed in Leamon et al., U.S. Pat. No. 7,323,305, which is incorporated by reference herein in its entirety. In an embodiment, the template may be associated with a substrate surface or present in a liquid phase with or without being coupled to a support. A primer 684 and DNA polymerase 686 are operably bound to the template 682. As used herein, "operably bound" generally refers to a primer being annealed to a template so that the primer's 3' end may be extended by a polymerase and that a polymerase is bound to such primer-template duplex (or in close proximity thereof) so that binding and/or extension may take place when dNTPs are added. In step 688, dNTP (shown as dATP) is added, and the DNA polymerase 686 incorporates a nucleotide "A" (since "T" is the next nucleotide in the template 682 and is complementary to the flowed dATP nucleotide). In step 690, a wash is performed. In step 692, the next dNTP (shown as dCTP) is added, and the DNA polymerase 686 incorporates a nucleotide "C" (since "G" is the next nucleotide in the template 682). The pH-based nucleic acid sequencing, in which base incorporations may be determined by measuring hydrogen ions that are generated as natural by-products of polymerase-catalyzed extension reactions, may be performed using at least in part one or more features of Anderson et al., A SYSTEM FOR MULTIPLEXED DIRECT ELECTRICAL DETECTION OF DNA SYNTHESIS, Sensors and Actuators B: Chem., 129:79-86 (2008); Rothberg et al., U.S. Pat. Appl. Publ. No. 2009/0026082; and Pourmand et al., DIRECT ELECTRICAL DETECTION OF DNA SYNTHESIS, Proc. Natl. Acad. Sci., 103:6466-6470 (2006), which are all incorporated by reference herein in their entirety. In an embodiment, after each addition of a dNTP, an additional step may be performed in which the reaction chambers are treated with a dNTP-destroying agent, such as apyrase, to eliminate any residual dNTPs remaining in the chamber that might result in spurious extensions in subsequent cycles.

In an embodiment, the primer-template-polymerase complex may be subjected to a series of exposures of different nucleotides in a pre-determined sequence or ordering. If one or more nucleotides are incorporated, then the signal resulting from the incorporation reaction may be detected, and after repeated cycles of nucleotide addition, primer extension, and signal acquisition, the nucleotide sequence of the template strand may be determined. The output signals measured throughout this process depend on the number of nucleotide incorporations. Specifically, in each addition step, the polymerase extends the primer by incorporating added dNTP only if the next base in the template is complementary to the added dNTP. With each incorporation, an hydrogen ion is released, and collectively a population released hydrogen ions change the local pH of the reaction chamber. The production of hydrogen ions may be monotonically related to the number of contiguous complementary bases in the template. Thus, when there is a number of contiguous identical complementary bases in the template (which may represent a homopolymer region), the number of hydrogen ions generated and thus the magnitude of the local pH change is proportional to the number of contiguous identical complementary bases (and the corresponding output signals are then sometimes referred to as "1-mer," "2-mer," "3-mer" output signals, etc.). If the next base in the template is not complementary to the added dNTP, then no incorporation occurs and no hydrogen ion is released (and the output signal is then sometimes referred to as a "0-mer" output signal). In each wash step of the cycle, an unbuffered wash solution at a predetermined pH may be used to remove the dNTP of the previous step in order to prevent misincorporations in later cycles. Deliveries of nucleotides to a reaction vessel or chamber may be referred to as "flows" of nucleotide triphosphates (or dNTPs). For convenience, a flow of dATP will sometimes be referred to as "a flow of A" or "an A flow," and a sequence of flows may be represented as a sequence of letters, such as "ATGT" indicating "a flow of dATP, followed by a flow of dTTP, followed by a flow of dGTP, followed by a flow of dTTP."

In various embodiments, output signals due to nucleotide incorporation may be processed, given knowledge of what nucleotide species were flowed and in what order to obtain such signals, to make base calls for the flows and compile consecutive base calls associated with a sample nucleic acid template into a read. A base call refers to a particular nucleotide identification (e.g., dATP ("A"), dCTP ("C"), dGTP ("G"), or dTTP ("T")). Base calling may include performing one or more signal normalizations, signal phase and signal droop (e.g, enzyme efficiency loss) estimations, and signal corrections, and may identify or estimate base calls for each flow for each defined space. Base calling may include performing or implementing one or more of the teachings disclosed in Davey et al., U.S. patent application Ser. No. 13/283,320, filed Oct. 27, 2011, published as U.S. Pat. Appl. Publ. No. 2012/0109598, which is incorporated by reference herein in their entirety. Other aspects of signal processing and base calling may include performing or implementing one or more of the teachings disclosed in Davey et al., U.S. patent application Ser. No. 13/340,490, filed on Dec. 29, 2011, published as U.S. Pat. Appl. Publ. No. 2012/0173159, and Sikora et al., U.S. patent application Ser. No. 13/588,408, filed on Aug. 17, 2012, published as U.S. Pat. Appl. Publ. No. 2013/0060482, which are all incorporated by reference herein in their entirety.

In accordance with the teachings and principles embodied in this application, new methods, systems, and computer readable media for repeat sequencing are provided. In some embodiments, the same template (e.g., nucleic acid template) or portion thereof may be observed or sequenced in whole or in part two or more times by repeating denaturing, priming, and sequencing steps. In some embodiments, sequencing reagents (e.g., polymerase, primer, nucleotides) used in a previous sequencing step may be replaced with new reagents in a subsequent sequencing step. New reagents may be of the same or different type as the reagents used in a previous sequencing step. In some cases, the reagents in the previous and subsequent sequencing steps may differ in certain properties, such as for example, nucleotide fidelity; rate of nucleotide incorporation; processivity; kinetics of nucleotide binding, catalysis, release of a nucleotide cleavage product, and/or polymerase translocation; exonuclease activity; and/or activity at certain temperatures.

Figure 5:
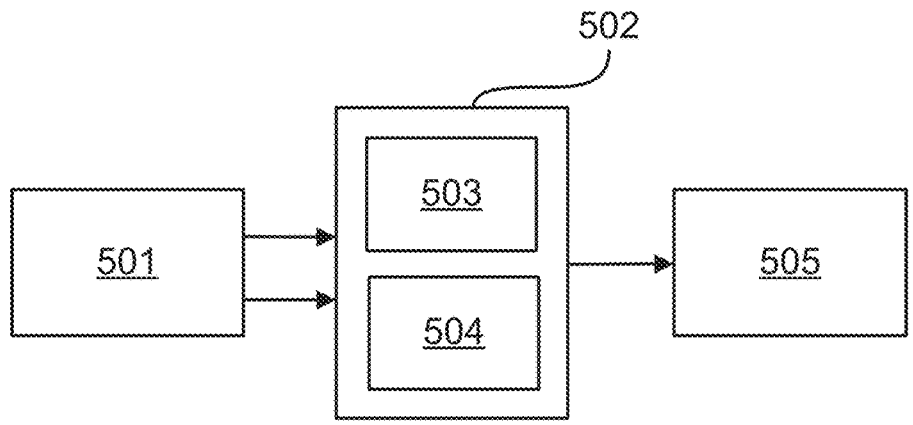
FIG. 5 illustrates an exemplary system for repeat sequencing.

FIG. 5 illustrates an exemplary system for repeat sequencing, which may include obtaining, processing, and/or analyzing nucleic acid sequencing data. The system includes a sequencing instrument 501, a server 502 or other computing means or resource, and one or more end user computers 505 or other computing means or resource. The sequencing instrument 501 may be configured to deliver reagents according to a plurality of predetermined reagent flow orderings. The sequencing instrument 501 may be configured to perform a first sequencing operation that includes delivering reagents according to a first predetermined reagent flow orderings, and to perform a second sequencing operation that includes delivering reagents according to a second predetermined reagent flow orderings, which may be different than the first predetermined reagent flow orderings. At least one of the first and second predetermined reagent flow orderings may be designed specifically for repeat sequencing. The server 502 may include a processor 503 and a memory and/or database 504. The sequencing instrument 501 and the server 502 may include one or more computer readable media for obtaining, processing, and/or analyzing nucleic acid sequencing data. In an embodiment, the instrument and the server or other computing means or resource may be configured as a single component.

Figure 6:
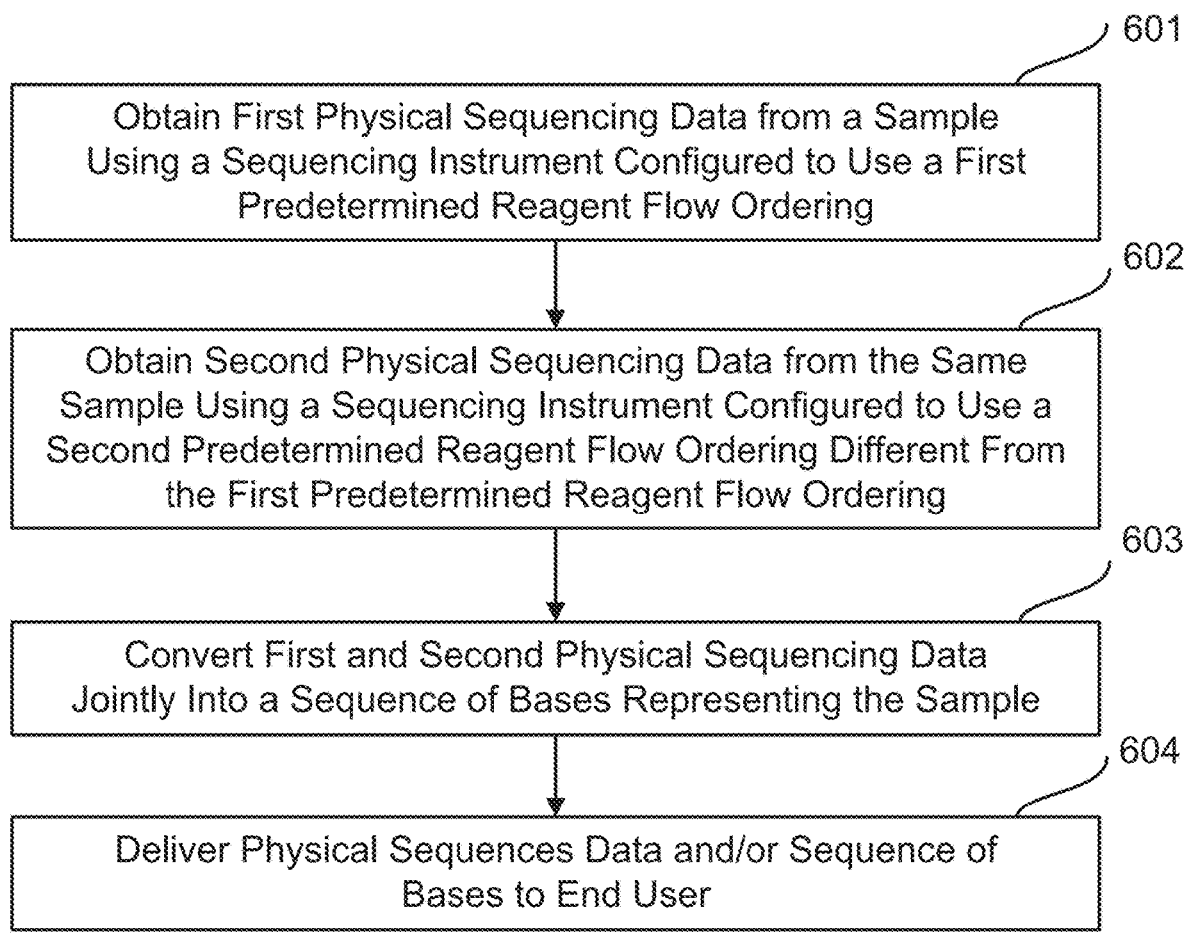
FIG. 6 illustrates an exemplary method for repeat sequencing.

FIG. 6 illustrates an exemplary method for repeat sequencing, which may include obtaining, processing, and/or analyzing nucleic acid sequencing data. In step 601, a user obtains first physical sequencing data from a sample template nucleic acid from an instrument configured to use a first predetermined reagent flow ordering. In step 602, a user obtains second physical sequencing data from the same sample template nucleic acid from an instrument configured to use a second predetermined reagent flow ordering different from the first predetermined reagent flow ordering. At least one of the first and second predetermined reagent flow orderings may be designed specifically for repeat sequencing. The physical sequencing data may include voltage data indicative of hydrogen ion concentrations. In step 603, a server or other computing means or resource converts the first and second physical sequencing data jointly into a sequence of bases. In step 604, the server or other computing means or resource delivers the physical sequencing data and/or sequence of bases to an end user.

According to an exemplary embodiment, there is provided a sequencing method, comprising: (a) sequencing a first portion of a target polynucleotide, thereby generating an extension product; (b) removing the extension product from the target polynucleotide; and (c) sequencing a second portion of the target polynucleotide. The first and second portions of the target polynucleotide may overlap at least partially, completely, or not at all. The sequencing in step (a) and/or (c) may comprise detecting nucleotide incorporation using an ISFET.

According to an exemplary embodiment, there is provided a sequencing method, comprising: (a) generating a first unlabeled extension product by sequencing a portion of a target polynucleotide using a first primer, a polymerase, and unlabeled nucleotides; (b) removing the first unlabeled extension product from the target polynucleotide; and (c) generating a second unlabeled extension product by sequencing a portion of the target polynucleotide with a second primer, a polymerase, and unlabeled nucleotides. The portions of the polynucleotide subjected to sequencing in step (a) and (c) may overlap at least partially, completely, or not at all. The sequencing in step (a) and/or (c) may comprise detecting nucleotide incorporation using an ISFET.

According to an exemplary embodiment, there is provided a sequencing method, comprising: (a) sequencing a first portion of a target polynucleotide strand using an ISFET, thereby generating a first extension product; (b) removing the first extension product from the target polynucleotide strand; and (c) sequencing a second portion of the target polynucleotide. The first and second portions of the target polynucleotide may overlap at least partially, completely, or not at all. The sequencing in step (a) and/or (c) may comprise detecting nucleotide incorporation using an ISFET. The sequencing of the first portion in step (a) may comprise generating unlabeled primer extension products using a polymerase and unlabeled nucleotides.

According to an exemplary embodiment, there is provided a sequencing method, comprising: (a) generating an unlabeled extension product by sequencing a first portion of a target polynucleotide which is proximal to an ISFET using a polymerase and unlabeled nucleotides; (b) removing the unlabeled extension product from the target polynucleotide using a chemical denaturant; and (c) sequencing a second portion of the target polynucleotide. The first and second portions of the target polynucleotide may overlap at least partially, completely, or not at all. The sequencing in step (a) and/or (c) may comprise detecting nucleotide incorporation using an ISFET.

According to an exemplary embodiment, there is provided a sequencing method, comprising: (a) forming a first primer extension product by extending a first primer hybridized to a strand of a target polynucleotide by incorporating one or more nucleotides into the first primer using a polymerase and determining the identity of at least one incorporated nucleotide; (b) removing the first primer extension product from the target polynucleotide strand; and (c) forming a second primer extension product by extending a second primer hybridized to a strand of the target polynucleotide by incorporating one or more nucleotides into the second primer using a polymerase and determining the identity of at least one incorporated nucleotide. The first and second primer extension products may overlap at least partially, completely, or not at all. Determining the identity of at least one incorporated nucleotide in step (a) and/or (c) may comprise detecting nucleotide incorporation using an ISFET. Forming the first and/or second primer extension product in step (a) and/or step (c) may comprise generating an unlabeled primer extension product using a polymerase and unlabeled nucleotides.

According to an exemplary embodiment, there is provided a sequencing method, comprising: (a) forming a first target/primer duplex by hybridizing a target polynucleotide and an oligonucleotide primer; (b) conducting a first primer extension reaction using at least one nucleotide and a first polymerase, thereby generating a first primer extension product; (c) identifying at least one incorporated nucleotide; (d) removing the first primer extension product from the target polynucleotide; (e) forming a second target/primer duplex by hybridizing the target polynucleotide and a second oligonucleotide primer; (f) conducting a second primer extension reaction using at least one nucleotide and a second polymerase, thereby generating a second primer extension product; and (g) identifying at least one incorporated nucleotide. Such a method may include step (h): removing the second primer extension product from the target polynucleotide. Steps (a)-(g) or steps (a)-(h) may be repeated at least once.

In the foregoing exemplary embodiments, the sequencing or generating or forming of step (a) may include flowing a plurality of nucleotides and/or reagents to the target polynucleotide according to a first predetermined ordering of nucleotides and/or reagents, and the sequencing or generating or forming of step (c) may include flowing a plurality of nucleotides and/or reagents to the target polynucleotide according to a second predetermined ordering of nucleotides and/or reagents. The second predetermined ordering of nucleotides and/or reagents may be the same as the first predetermined ordering of nucleotides and/or reagents. Preferably, however, the second predetermined ordering of nucleotides and/or reagents is different than the first predetermined ordering of nucleotides and/or reagents. Further preferably, at least one of the first and second predetermined orderings of nucleotides and/or reagents may be designed specifically for repeat sequencing.

According to an exemplary embodiment, there is provided a method for sequencing a nucleic acid template, comprising: (a) performing a first sequencing process on the nucleic acid template to obtain a first sequencing result, wherein the first sequencing process includes flowing nucleotides and/or reagents to the nucleic acid template according to a first predetermined ordering of nucleotides and/or reagents; (b) after the first sequencing process, performing a second sequencing process on the nucleic acid template to obtain a second sequencing result, wherein the second sequencing process includes flowing nucleotides and/or reagents to the nucleic acid template according to a second predetermined ordering of nucleotides and/or reagents that is different from the first predetermined ordering of nucleotides and/or reagents; and (c) determining a sequence of bases corresponding to at least a portion of the nucleic acid template using both the first sequencing result and the second sequencing result.

Exemplary Sequencing Conditions

In some embodiments, the sequencing may include obtaining sequence information from at least some or all nucleotide within a nucleic acid strand or region thereof. The sequencing may be performed using any suitable sequencing technique, including: chemical degradation sequencing, chain-termination sequencing, sequencing-by-synthesis, sequencing-by-ligation, pyrophosphate-based sequencing, massively parallel sequencing, single molecule sequencing, ion-sensitive sequencing as described herein, and any other suitable sequencing technique. In various embodiments, a target polynucleotide may be re-sequenced multiple times, or a target polynucleotide may be subjected to continuing sequencing reactions multiple times. For example, a target polynucleotide may be sequenced 1, 2, 3, 4, or 5 times, or up to 10 times, or up to 15 times, or up to 20 times, or up to 30 times, or up to 40 times, or up to 50 times, or more than 50 times.

In some embodiments, the target polynucleotide may include: at least one primer binding region having a sequence that is partially or fully complementary to at least a portion of an oligonucleotide primer; multiple primer binding regions having different sequences or having sequences that are essentially the same; and/or first, second, or more primer binding regions that overlap at least partially, completely, or not at all. In some embodiments, the target polynucleotide may comprise: a linear or circular molecule; a single-stranded polynucleotide; a double-stranded polynucleotide; DNA, RNA, chimeric DNA/RNA, or nucleic acid analogs; polymers of deoxyribonucleotides, ribonucleotides, and/or analogs thereof; and/or a plurality of different polynucleotides comprising naturally-occurring, synthetic, recombinant, cloned, amplified, unamplified or archived (e.g., preserved) forms.

In some embodiments, the target polynucleotide may comprise a polynucleotide library construct having one or both ends joined with a nucleic acid adaptor sequence. The polynucleotide library construct may comprise first and second ends, where the first end is joined to a first nucleic acid adaptor and the second end is joined to a second nucleic acid adaptor. Such first and second adaptors may have the same or a different sequence and may be such that at least a portion of the first or second adaptor comprises at least a portion of a primer binding region and may hybridize to at least a portion of an oligonucleotide primer. In some embodiments, an adaptor may comprise DNA, RNA, chimeric DNA/RNA, or nucleic acid analogs; one or more deoxyribonucleoside or ribonucleoside residues; single-stranded or double-stranded nucleic acids; and/or nucleic acid single-stranded and/or double-stranded portions. In some embodiments, an adaptor may have any suitable structure, including linear, hairpin, forked, or stem-loop, and may have any suitable length, including fewer than 10 bases in length, about 10-20 bases in length, about 20-50 bases in length, about 50-100 bases in length, or longer.

In various embodiments, the extension product may be generated by conducting a primer extension reaction with a primer, polymerase, and nucleotides, which may comprise contacting a target/primer duplex with a polymerase and at least one nucleotide under conditions suitable for catalyzing a template-dependent nucleotide polymerization reaction, thereby generating a primer extension product. The two different nucleic acids, or the two different regions of a nucleic acid, may be complementary (which may be standard A-T or C-G pairings or other forms of base pairings) or partially complementary. Conditions suitable for hybridization include suitable reagents/parameters such as salts (e.g., sodium salts, such as NaCl, sodium citrate, and/or sodium phosphate); suitable buffers (e.g., formamide, sodium dodecyl sulfate, mixture of NaCl and sodium citrate, sodium phosphate, sodium pyrophosphate, Denhardt's solution, SDS, dextran sulfate and/or bovine serum albumin) at suitable composition and concentration; pH (e.g., pH range of about 5-10, or about 6-9, or about 6.5-8, or about 6.5-7); temperature (e.g., temperature range of about 15-25° C., or about 25-35° C., or about 35-45° C., or about 45-55° C., or about 55-65° C., or about 65-75° C., or about 75-85° C., or about 85-95° C., or about 95-99° C., or higher); GC % content of the polynucleotide and primers; and/or time (e.g., time range of about 1-30 seconds, or about 30-60 seconds, or about 1-10 minutes, or about 10-20minutes, or about 20-30 minutes, or about 30-40 minutes, or about 40-50 minutes, or about 50-60 minutes, or longer).

In some embodiments, the removing may include removing an extension product using physical, chemical, and/or enzymatic reactions. For example, a primer extension product may be denatured/melted from a target polynucleotide using an elevated temperature (e.g., about 75-100° C. without formamide or about 45-90° C. with formamide) or a chemical denaturant (e.g., a compound known to dissociate double-stranded nucleic acid molecules, such as formamide, urea, DMSO, alkali conditions, low salt or very-low salt conditions, or water). A primer extension product may also be degraded using a nuclease enzyme. In some embodiments, an extension product may be degraded using a nucleic acid degrading enzyme, such as a 5'→3' or 3'→5' exonuclease (e.g., exonuclease I, exonuclease III, or T7 gene 6 exonuclease).

In some embodiments, at least a portion of an oligonucleotide primer is fully or partially complementary to a primer binding region on the target polynucleotide. An oligonucleotide primer may comprise: a single-stranded or double-stranded polynucleotide; DNA, RNA, chimeric DNA/RNA, or nucleic acid analogs; polymers of deoxyribonucleotides, ribonucleotides, and/or analogs thereof; and/or a plurality of different polynucleotides comprising naturally-occurring, synthetic, recombinant, cloned, amplified, unamplified or archived (e.g., preserved) forms. In some embodiments, at least a portion of an oligonucleotide primer comprises a sequence having no sequence identity or complementarity to a region on the target polynucleotide (e.g., tailed primers).

In some embodiments, a nucleotide may comprise any compound that can bind selectively to, or can be polymerized by, a polymerase, including a naturally occurring nucleotide (e.g., typically comprising base, sugar and phosphate moieties); a non-naturally occurring nucleotide (e.g., lacking some or all of base, sugar and phosphate moieties); a nucleotide analog, regardless of their structure, that can bind selectively to, or can be polymerized by, a polymerase; and/or nucleotide analogs such as ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds. In some embodiments, a nucleotide may include non-oxygen moieties such as, for example, thio- or borano- moieties, in place of an oxygen moiety. In some embodiments, nucleotides may include a chain of phosphorus atoms comprising three, four, five, six, seven, eight, nine, ten or more phosphorus atoms. In some embodiments, a nucleotide may include a purine or pyrimidine base, including adenine, guanine, cytosine, thymine, or uracil. In some embodiments, a nucleotide may include dATP, dGTP, dCTP, dTTP, and dUTP.

In some embodiments, one or more of the target polynucleotide, oligonucleotide primer, and/or nucleotide may be labeled with a label. The label may comprise a detectable moiety, which may include compounds that are luminescent, photoluminescent, electroluminescent, bioluminescent, chemiluminescent, fluorescent, phosphorescent, or otherwise electrochemically detectable, including fluorophores, chromophores, radioisotopes, haptens, affinity tags, and certain atoms or enzymes, for example. The detectable moiety may generate, or cause to generate, a detectable signal, which may be generated from a chemical or physical change (e.g., heat, light, electrical change, pH, salt concentration, enzymatic activity, or proximity events (which may include two reporter moieties approaching each other, or associating with each other, or binding with each other)), and may be detected thermally, optically, electrically, chemically, enzymatically, or via mass spectroscopy or Raman spectroscopy, for example. In other embodiments, one or more of the target polynucleotide, oligonucleotide primer, and/or nucleotide may be unlabeled. In some embodiments, non-labeled nucleotides may be employed for nucleic acid sequencing to generate non-labeled primer extension products. For example, incorporation of non-labeled nucleotides may be detected using an ion-sensitive sensor (e.g., an ISFET or an ion-sensitive pH detector).

In some embodiments, a polymerase may include any enzyme, or fragment or subunit of thereof, that can catalyze the polymerization of nucleotides and/or nucleotide analogs. The polymerase may be a DNA polymerase, which may include bacterial DNA polymerases, eukaryotic DNA polymerases, archaeal DNA polymerases, viral DNA polymerases, and phage DNA polymerases; a DNA-dependent polymerase; a replicase; a primase; an RNA-dependent polymerase (including RNA-dependent DNA polymerases such as, for example, reverse transcriptases); a T3, T5, T7, or SP6 RNA polymerase; a thermo-labile polymerase, or a thermo-stable polymerase. The polymerase may be selected from low or high fidelity polymerases, which may include naturally occurring polymerases and any subunits and truncations thereof; mutant polymerases; variant polymerases; recombinant, fusion or otherwise engineered polymerases; chemically modified polymerases; and synthetic molecules or assemblies, and any analogs, derivatives or fragments thereof that retain the ability to catalyze nucleotide polymerization. Typically, a polymerase comprises one or more active sites at which nucleotide binding and/or catalysis of nucleotide polymerization can occur. In some embodiments, a polymerase includes or lacks other enzymatic activities, such as, e.g., 3' to 5' exonuclease activity or 5' to 3' exonuclease activity. In some embodiments, sequencing reactions may be conducted with a single type of polymerase or a mixture of polymerases or ligases. In some embodiments, the polymerase may be an *E. coli* large fragment DNA polymerase I (e.g., Klenow).

In some embodiments, a target polynucleotide and/or an oligonucleotide primer may be attached or linked to a surface in a manner that withstands flowing, washing, aspirating, and changes in salt, temperature, chemical, enzymatic, and/or pH conditions. The surface may be an outer or top-most layer or boundary of an object, or may be interior to the boundary of an object; may be porous, semi-porous, or non-porous; may be mobile; may be a bead, particle, or microparticle; may be a bead or particle having an iron core or comprising a hydrogel or agarose; may be a filter, flowcell, well, microwell, groove, channel reservoir, gel, or inner wall of a capillary; may be planar, concave, convex, or any combination thereof; may include texture (e.g., etched, cavitated, pores, three-dimensional scaffolds, or bumps); and may be nonmagnetic, magnetic, or paramagnetic. In some embodiments, the surface may include particles having a shape that is spherical, hemispherical, cylindrical, barrel-shaped, toroidal, rod-like, disc-like, conical, triangular, cubical, polygonal, tubular, wire-like, or irregular. In some embodiments, the surface may be made from any suitable material, including glass, borosilicate glass, silica, quartz, fused quartz, mica, polyacrylamide, plastic polystyrene, polycarbonate, polymethacrylate (PMA), polymethyl methacrylate (PMMA), polydimethylsiloxane (PDMS), silicon, germanium, graphite, ceramics, semiconductor, high refractive index dielectrics, crystals, gels, polymers, or films (e.g., films of gold, silver, aluminum, or diamond). In some embodiments, the surface may be paramagnetic beads attached with streptavidin (e.g., Dynabeads™ M-270 from Invitrogen, Carlsbad, Calif.). In some embodiments, one or more oligonucleotide primers may be attached to the surface in any suitable manner.

Exemplary Flow Orderings for Repeat Sequencing

In some embodiments, the predetermined orderings of nucleotides and/or reagents may be based on a cyclical, repeating pattern consisting of consecutive repeats of a short pre-determined reagent flow ordering (e.g., consecutive repeats of pre-determined sequence of four nucleotide reagents such as, for example, "ACTG ACTG ... "), or may be based in whole or in part on some other pattern of reagent flows (such as, e.g., any of the various reagent flow orderings discussed herein and/or in Hubbell et al., U.S. Pat. Appl. Publ. No. 2012/0264621, published Oct. 18, 2012, which is incorporated by reference herein in its entirety), and may also be based on some combination thereof.

In an embodiment, the predetermined ordering(s) may be any of the various reagent flow orderings discussed in Hubbell et al., U.S. Pat. Appl. Publ. No. 2012/0264621, published Oct. 18, 2012, such as, e.g., the SAMBA, CONTRADANZON, and SAMBA.GAFIEIRA flow orderings. These orderings were designed specifically for phase protection and may therefore not be optimal for repeat sequencing, however they are still suitable for repeat sequencing when considering repeat sequencing criteria in combination with other relevant criteria (e.g., efficiency of extension and dephasing merit).

In an embodiment, the predetermined ordering(s) may be a combination of Kautz sequences generated using all possible dimers of A, C, G, and T (which are AG, AC, AT, CA, CG, CT, GA, GC, GT, TA, TC, and TG). For example, the flow ordering may be constructed by starting with a first 4-flow block of TACG (for example), then appending a second 4-flow block of TCAG (e.g., a 1324 transpose relative to TACG), and then appending a third 4-flow block of CTGA (e.g., a 2143 transpose relative to TCAG), which forms a first 12-flow Kautz sequence. A second 12-flow Kautz sequence may then be generated using the same transposition pattern but starting with TCGA (thus yielding TCGA, followed by TGCA, followed by GTAC). A third 12-flow Kautz sequence may then be generated using the same transposition pattern but starting with TGAC (thus yielding TGAC, followed by TACG, followed by ATCG). In an example, the concatenation of these first, second, and third 12-flow Kautz sequences yields a 36-flow ordering, which is referred to herein as VALSE. Such a 36-flow ordering may be repeated as necessary for the needs of any particular sequencing operation. Other similar combinations (e.g., starting with a different 4-flow block) are of course possible.

In an embodiment, the predetermined ordering(s) may be a pattern selected to delay and/or rotate flows. For example, the flow ordering may be constructed by starting with a first 4-flow block of TACG (for example), then adding a predetermined number n1 of repeats of a triplet TAC (e.g., lacking a G flow), then adding an isolated G flow, then adding a permutation (e.g., first rotation) of the first 4-flow block (e.g., ACGT), then adding a predetermined number n2 of repeats of a triplet ACG (e.g., lacking a T flow), then adding an isolated T flow, then adding a permutation (e.g., second rotation) of the first 4-flow block (e.g., CGTA), then adding a predetermined number n3 of repeats of a triplet CGT (e.g., lacking a A flow), then adding an isolated A flow, then adding a permutation (e.g., third rotation) of the first 4-flow block (e.g., GTAC), then adding a predetermined number n4 of repeats of a triplet GTA (e.g., lacking a C flow), then adding an isolated C flow. In an example, the above sequence of flows, with n1=n2=n3=n4=3, leads to a 56-flow ordering, which is referred to herein as CHACHACHA. Different lengths may be obtained by using other integer values for n1, n2, n3, and n4 (which may all be the same or may be different). Such an ordering may be repeated as necessary for the needs of any particular sequencing operation. Other similar combinations (e.g., starting with a different 4-flow block) are of course possible.

In an embodiment, the predetermined ordering(s) may be a combination of loops through a Kautz graph of possible dimers of A, C, G, and T, excluding a subset of dimers chosen to optimize a sequence property. In an example, the sequence property may be to exclude dimers that occur within a second flow order. In an example, two distinct orderings containing 6 dimers each may be generated from the 12 possible dimers containing a pair of bases. In an example, to perform sequencing with all four A, C, G, and T bases, the selected dimers may (i) include all four bases and (ii) form a graph that can be traced to form a continuous flow ordering (e.g., every base has at least one dimer leading from it and all four bases can be reached). Such continuous flow orderings may be decomposed into successive loops through the graph. For example, the flow ordering may be constructed using the following generating pattern: T→A→C→G→T; G→A; and A→G, representing a set of dimers defining the following graph:

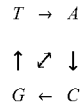

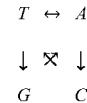

to obtain basic loops containing all 4 bases and together containing all dimers specified. (Defining a basic loop to contain all 4 bases ensures that the extension efficiency of the flow order is never worse than the efficiency of the worst basic loop which is guaranteed to extend at least one base in any sequence.) In an embodiment, the three loops (1) TACGTACG, (2) TACGACG, and (3) TAGTACG, which are present in the preceding graph, contain all 4 bases and together contain all dimers specified by the graph. These three distinct loops may be combined in various ways, such as repeating loops 1, 2, and 3 in sequence for a desired number of times, or repeating identical or different permutations of those three loops for a desired number of times (e.g., one could use loop 1, then loop 2, then loop 3, then loop 1, then loop 3, then loop 2, etc.). In an example, one could use loop 1, then loop 2, then loop 3, then loop 1, then loop 3, then loop 2, then loop 3, then loop 1, then loop 2, then loop 3, then loop 2, then loop 1, then loop 2, then loop 3, then loop 1, then loop 2, then loop 1, and then loop 3, which is referred to herein as BOXSTEP_LEAD. In other examples, the flow ordering may be constructed by combining the complements of such loops. In an example, the complement (the graph defined by the 6 dimers not used in BOXSTEP_LEAD, which is also the set of dimers defined by the complement of the dimers) of BOXSTEP_LEAD is referred to herein as BOXSTEP_FOLLOW. Such an ordering may be repeated as necessary for the needs of any particular sequencing operation. Other similar combinations (e.g., starting with different generating patterns) are of course possible.

In an embodiment, the predetermined ordering(s) may be more irregular combinations of groups of distinct dimers of A, C, G, and T. For example, a first group of 6 of the 12 distinct dimers may be used for one flow order and a second group of 6 of the 12 distinct dimers may be used for another flow order (without necessarily being complements). In another example, the predetermined ordering(s) may be obtained by combining the above loops, separated by intervening blocks such as, e.g., loop 1, followed by an intervening block (e.g., "ACG"), followed by loop 1, followed by another intervening block (e.g., "TAG"), followed by loop 3, which is referred to herein as BOXSTEP1. In other examples, the flow ordering may be constructed by combining the complements of such loops. In an example, the complement of BOXSTEP1 is referred to herein as BOXSTEP2.

In an embodiment, the predetermined ordering(s) may be a combination of building blocks designed for complementary sequencing in both directions. For example, one might compare a sequence and its reverse complement (e.g., "AC" turns into "GT" in the other direction, and "AT" turns into "AT" in the other direction) and choose dimer contexts that are anti-correlated between forward and reverse directions (e.g., "TG" eliminates "CA" from the other direction, and "GA" eliminates "TC" from the other direction). In an example, the flow ordering may be constructed using generating pattern: T→G→A→C→T; T→A; and A→T, representing a set of dimers defining the following graph:

to obtain, for example, forward loops (1) TGACTGAC, (2) TGACTAC, and (3) TGATGAC and combine them in various ways, such as repeating loops 1, 2, and 3 in sequence for a desired number of times, or repeating identical or different permutations of those three loops for a desired number of times (e.g., one could use loop 1, then loop 2, then loop 3, then loop 1, then loop 3, then loop 2, etc.). In an example, one could use loop 1, then loop 2, then loop 3, then loop 1, then loop 3, then loop 2, then loop 3, then loop 1, then loop 2, then loop 3, then loop 2, then loop 1, then loop 2, then loop 3, then loop 1, then loop 2, then loop 1, and then loop 3, which is referred to herein as CEROC_FORWARD or CEROC_LEAD. In another example, the flow ordering may be constructed using generating pattern G→A→C→T→G; G→C; and C→G, representing a set of dimers defining the following graph:

$$\begin{array}{ccc} T & & A \\ \downarrow & \times & \downarrow \\ G & \leftrightarrow & C \end{array}$$

to obtain, for example, reverse loops (1) GACTGACT, (2) GACTGCT, and (3) GACGACT and combine them in various ways, such as repeating loops 1, 2, and 3 in sequence for a desired number of times, or repeating identical or different permutations of those three loops for a desired number of times (e.g., one could use loop 1, then loop 2, then loop 3, then loop 1, then loop 3, then loop 2, etc.). In an example, one could use loop 1, then loop 2, then loop 3, then loop 1, then loop 3, then loop 2, then loop 3, then loop 1, then loop 2, then loop 3, then loop 2, then loop 1, then loop 2, then loop 3, then loop 1, then loop 2, then loop 1, and then loop 3, which is referred to herein as CEROC_REVERSE or CEROC_FOLLOW. Such an ordering may be repeated as necessary for the needs of any particular sequencing operation. Other similar combinations (e.g., starting with different generating patterns) are of course possible.

In an embodiment, the predetermined ordering(s) may be generated based on low autocorrelation orderings derived using Costas arrays. For example, one may look at possible sequences corresponding to Costas arrays of a suitable size, reduce the sequences to sequences of 4 possible symbols that can be mapped to bases A, C, G, and T via a modulo 4 operation, trim any repeats, and finally select a set of candidate sequences having desired relative proportions of A, C, G, and T (e.g., preferably each within the range of about 20% to 30%). Then, the candidate sequences may be evaluated for suitability for re-sequencing (and/or other criteria).

Evaluation of Candidate Flow Orderings

According to exemplary embodiments, there are provided methods for designing, evaluating and/or ranking flow orderings to identify which ones are more suitable for repeat sequencing. In an embodiment, candidate flow orderings may be evaluated and/or ranked based on trade-offs between various characteristics, including extension efficiency (that is, some assessment of how rapidly a sequence can be extended by a homopolymer), dephasing merit (that is, some estimate of the ability of a particular flow ordering to minimize the effects of phasing issues on sequencing), and re-sequencing accuracy merit (that is, some estimate or indication of the ability of a group of candidate flow orderings to improve sequencing accuracy in the presence of redundant data obtained from repeat sequencing runs performed using the candidate flow orderings).

A candidate flow ordering may be first evaluated based on efficiency of extension and dephasing merit, as discussed in Hubbell et al., U.S. Pat. Appl. Publ. No. 2012/0264621, published Oct. 18, 2012, and then further evaluated based on re-sequencing accuracy merit.

Figure 7:
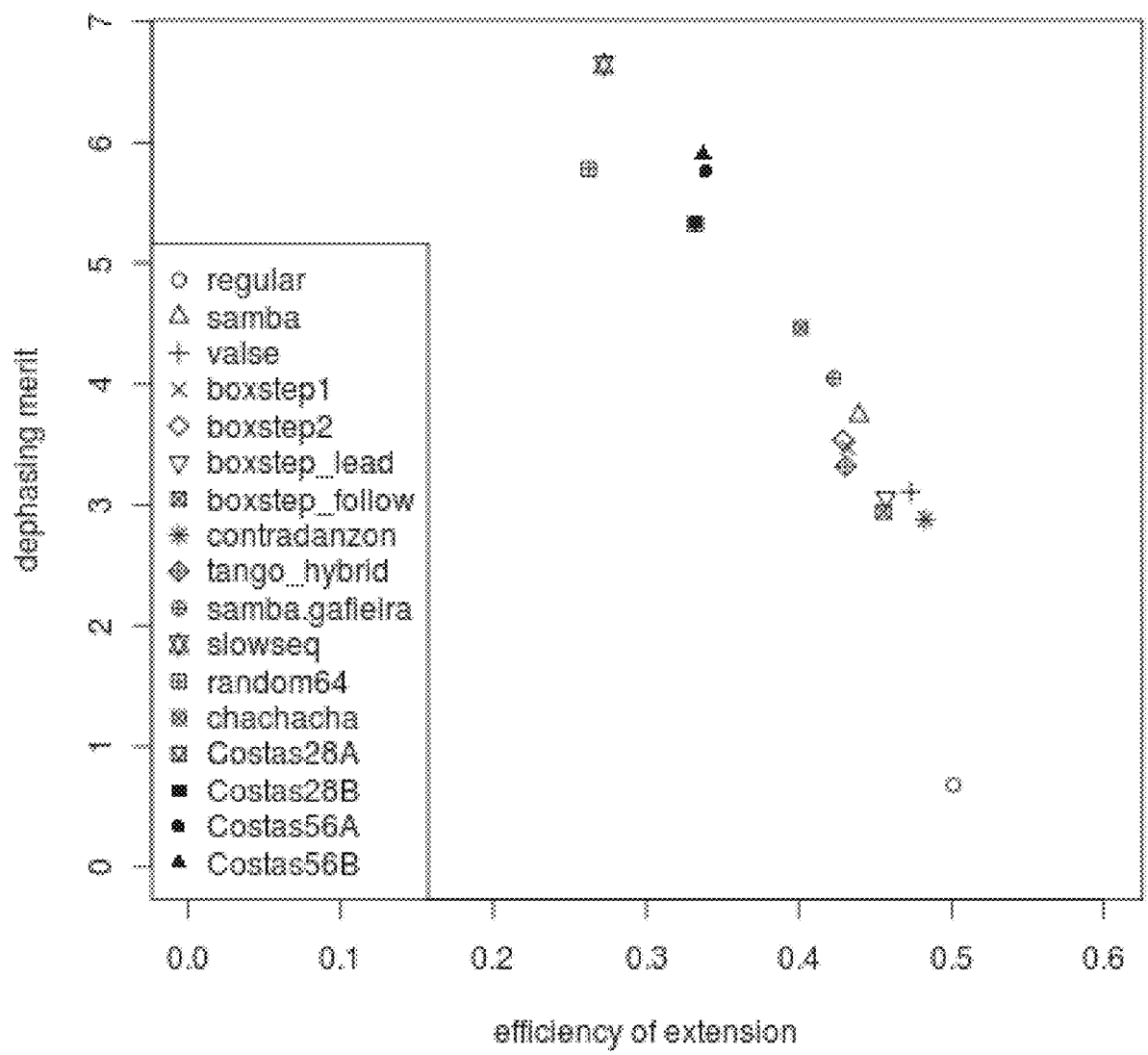
FIG. 7 illustrates a comparison of efficiency of extension and dephasing merit for various flow orderings.

FIG. 7 illustrates a comparison of efficiency of extension and dephasing merit for various flow orderings. It shows simulated performance for 17 particular flow orderings (referred to as REGULAR, SAMBA, VALSE, BOXSTEP1, BOXSTEP2, BOXSTEP_LEAD, BOXSTEP_FOLLOW, CONTRADANZON, TANGO_HYBRID, SAMBA. GAFIEIRA, SLOWSEQ, RANDOM64, CHACHACHA, COSTAS28A, COSTAS28B, COSTAS56A, AND COSTAS56B) used against random sequences drawn from a uniform distribution of the four bases. The SAMBA flow represents a particularly good compromise between dephasing effectiveness and efficiency of extension, however, that flow may not be optimal for repeat sequencing.

A candidate flow ordering may then further evaluated based on re-sequencing accuracy merit. In some cases, the re-sequencing accuracy merit of a flow ordering may be designed or evaluated based on a flow context within the ordering and flow-space realignment considerations. For example, if in an ordering "T" is always followed by "A" then regardless of how offset a read may be multiple reads always "see" the same sequence context. As a result, one then always learns the same information about the sequence every time, and such an ordering is less likely to be good or optimal for repeat sequencing. If, however, in an ordering "T" is followed evenly by "A," "C," and "G" then offset reads may see different sequence contexts (e.g., "TA" eliminates possible insertions within "TA," "TC" eliminates possible insertions within "TC," and "TG" eliminates possible insertions within "TG"). As a result, the information in each context may provide evidence for or against possible variants, and an ordering is more likely to be good or optimal for repeat sequencing. More generally, if a sequence contains bases "XY" (selected from A, C, G, or T), there is a ⅓ change of having "XY" in an uncorrelated flow ordering, and a 5/9 change of having "XY" in one of two uncorrelated flow orderings. Such knowledge and principles may be helpful to infer likelihoods relevant, for example, in variant calling, and may allow design or evaluation of flow orderings for repeat sequencing. In an embodiment, sequencing twice with flow orderings uncorrelated with the sequence and with each other may yield a chance of about 60% of eliminating insertions at a given position in the sequence.

Figure 8:
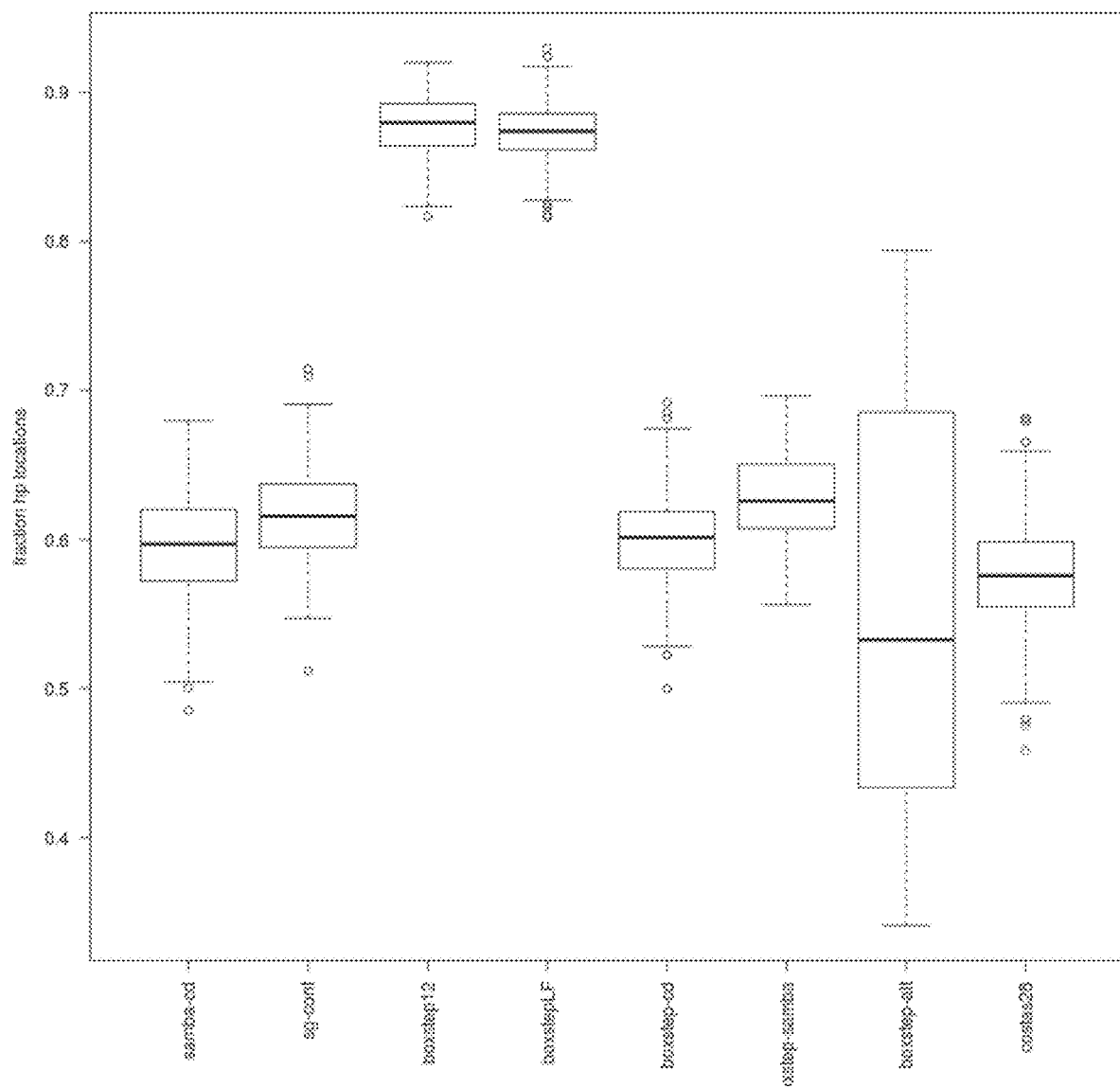
FIG. 8 illustrates a comparison of different flow ordering pairs for re-sequencing.

FIG. 8 illustrates a comparison of different flow ordering pairs for re-sequencing. The pairs are rated by uniquely excluded insertions, as described in the preceding paragraph. That is, at any given sequence location where there is a transition between homopolymers, one may exclude any insertion events not allowed by the flow order. Thus, across all sequence locations, one may sum up the proportion of insertion events excluded as a figure of merit: a location where all insertions are excluded by the flow order counts as 1, a location where 50% of the insertions are excluded counts as 0.5, and a location where no insertions are excluded counts as 0. As shown, the combination of BOXSTEP1 and BOXSTEP2, and the combination of BOXSTEP_LEAD and BOXSTEP_FOLLOW exhibit a high level of uniquely excluded insertions, on average across all sequence locations covered by reads. This indicates that using these two flow orders together provides a benefit over merely uncorrelated flow orders.

FIGS. 9A and 9B illustrate exemplary simulation data corresponding to signal response curves for a cyclical, repeating flow ordering of "TACG TACG . . . ." The cyclical, repeating flow ordering of FIGS. 9A and 9B exhibits significant signal overlap and is in a sense the worst possible flow ordering from a dephasing merit standpoint, which makes it suitable for baseline comparison purposes. FIG. 9A shows signal response curves with signal intensity on the y-axis and the nth flow number (time) on the x-axis and displays three triplet sets of plot lines, each of the triplet sets having a darker solid line in the middle between two lighter dotted lines. The bottom-most triplet set of plot lines show the signal from 0-mer events (non-incorporation); the middle triplet set of plot lines show the signal from 1-mer incorporation events; and the top-most triplet set of plot lines show the signal from 2-mer incorporation events. Within each triplet set, the darker solid line in the middle represents the median signal, the lighter dotted line above represents the 25 percentile signal, and the lighter dotted line below represents the 75 percentile signal. As shown in FIG. 9A, while the signal for the 1-mer and 2-mer incorporation events degrades as the sequencing read progresses, the signal produced by non-incorporation 0-mer events (e.g., the background signal) increases as the sequencing read progresses. Thus, at later portions of the sequencing read, the signal resolution diminishes and it becomes more difficult to distinguish the 0-mer, 1-mer, and 2-mer events from each other. FIG. 9B illustrates exemplary simulation data corresponding to template population evolution as sequencing progresses for the cyclical, repeating flow ordering of FIG. 9A. The y-axis represents the population fraction, with the upper plot line representing the largest population (in-sync) and the lower plot line representing the second largest population (out-of-sync). As shown in FIG. 9B, the relative number of in-sync templates decreases while the relative number of out-of-sync templates increases with progression of the sequencing read due to the loss of phase synchrony.

FIGS. 10A and 10B illustrate exemplary simulation data corresponding to signal response curves of the same format as FIGS. 9A and 9B, but for a BOXSTEP_LEAD flow ordering. Similarly, FIGS. 11A and 11B illustrate exemplary simulation data corresponding to signal response curves of the same format as FIGS. 9A and 9B, but for a BOXSTEP_FOLLOW flow ordering. FIGS. 10A and 11A show that the flow orderings have acceptable signal resolution/separation properties, which are significantly better that those of FIG. 9A. In turn, FIGS. 10B and 11B show that the flow orderings have acceptable rates at which out-of-phase populations accumulate, which are significantly better that those of FIG. 9B. Looking back at FIG. 8, although the BOXSTEP variants are not quite at the efficient frontier and thus not as optimal as SAMBA based solely on dephasing effectiveness and efficiency of extension, they are relatively good at both efficiency of extension and dephasing merit.

Figure 12:
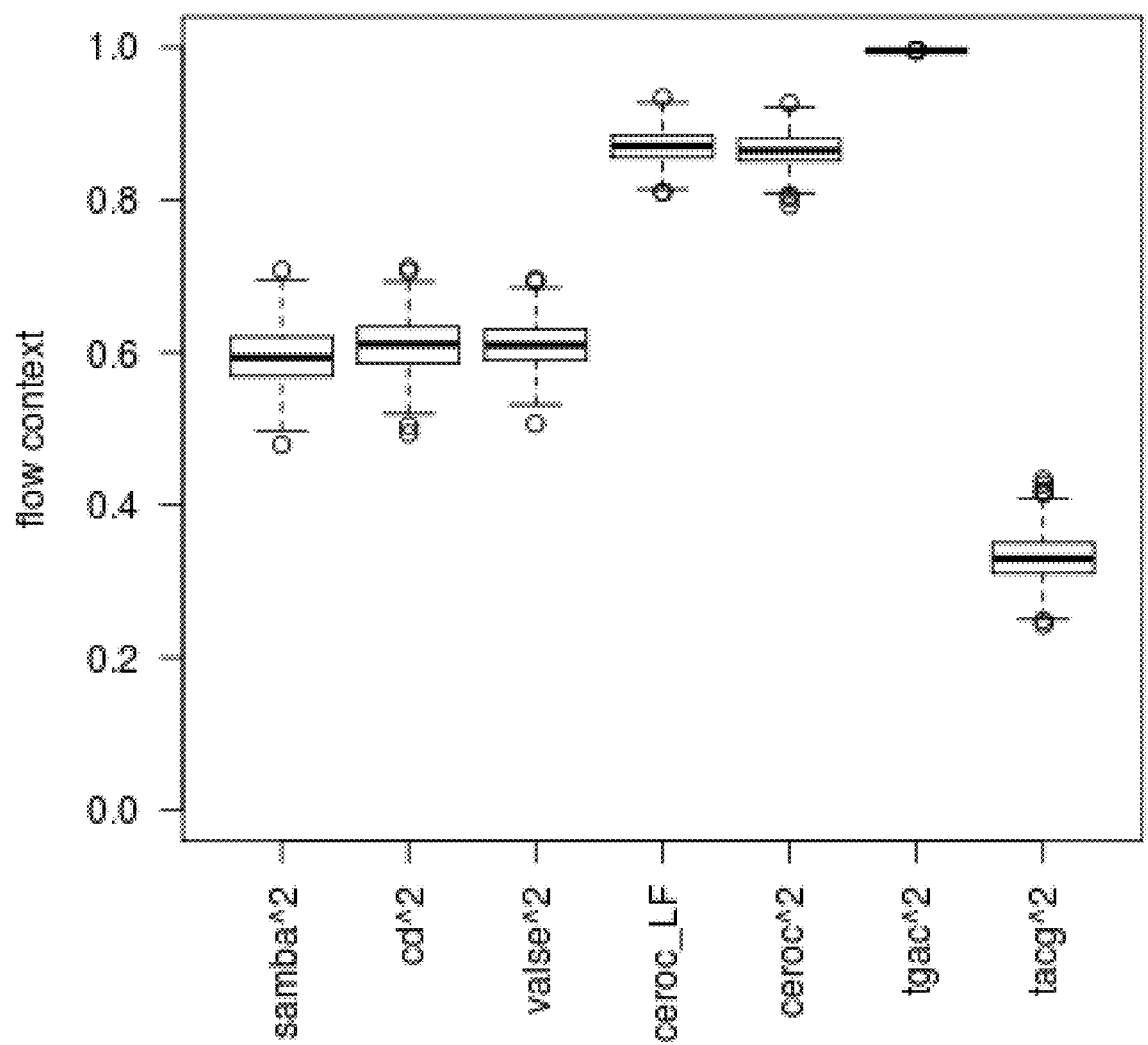
FIG. 12 illustrates a comparison of different flow ordering pairs for bi-directional sequencing.

FIG. 12 illustrates a comparison of different flow ordering pairs for bi-directional sequencing. The pairs are rated by fraction of flow context specific insertions excluded. This is the same metric discussed previously for two flow orders sequencing in the same direction, however with the added complexity that some insertions may be excluded due to the reverse-complementing of the sequencing process, instead of merely comparing in the same direction with the same base being inserted. As previously, 1.0 means no (errorroneous) insertion is possible given the flow order, 0.0 means any (single, distinct) base insertion is possible at such a location. As shown, CEROC flows exhibit a high level of ability exclude insertions across average sequence locations. It should be noted here that the efficiency of extension and phase correction criteria are not connected to this additional pairwise metric. In this regard, the regular flow order TGAC has no phase correcting ability whatsoever, but perfectly excludes all insertions at all locations when used for bi-directional sequencing.

Figure 13A:
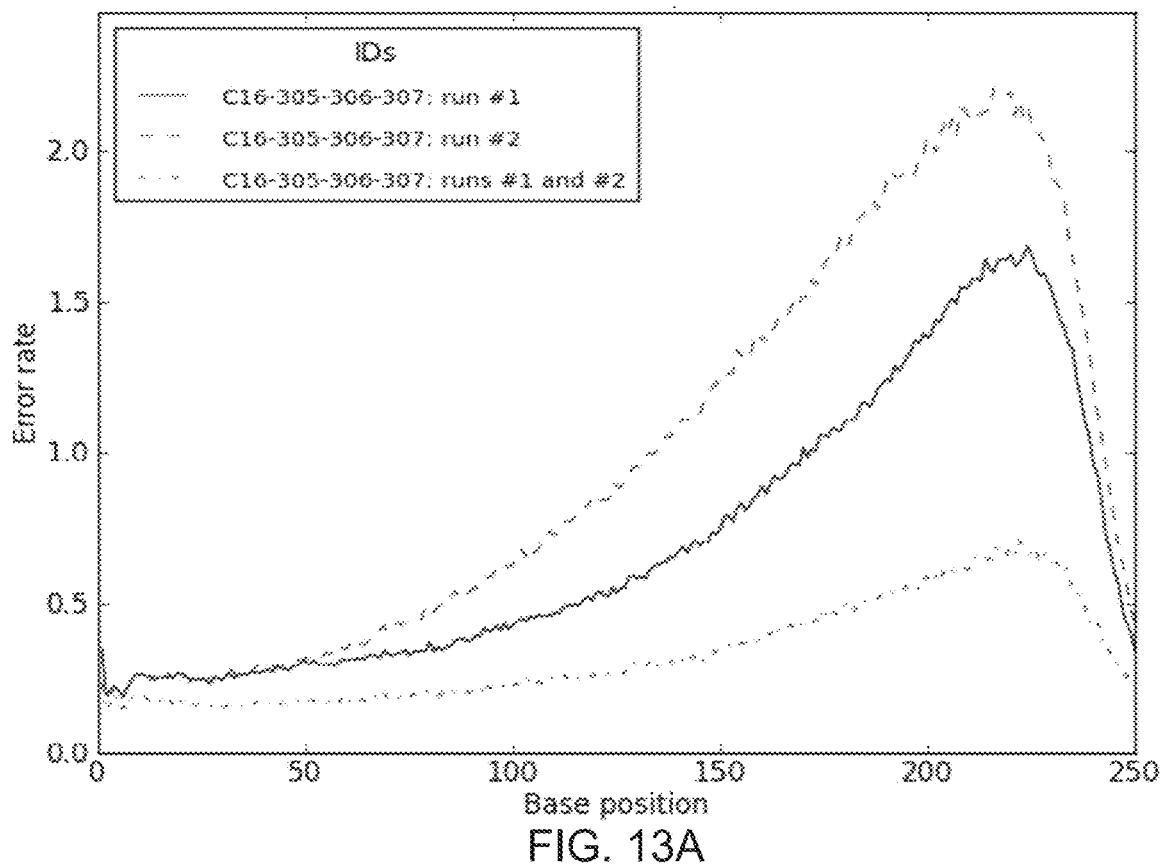
FIGS. 13A-13C illustrate exemplary base error rates for pairs of runs selected from three repeat sequencing runs in a high template load situation.
Figure 13B:
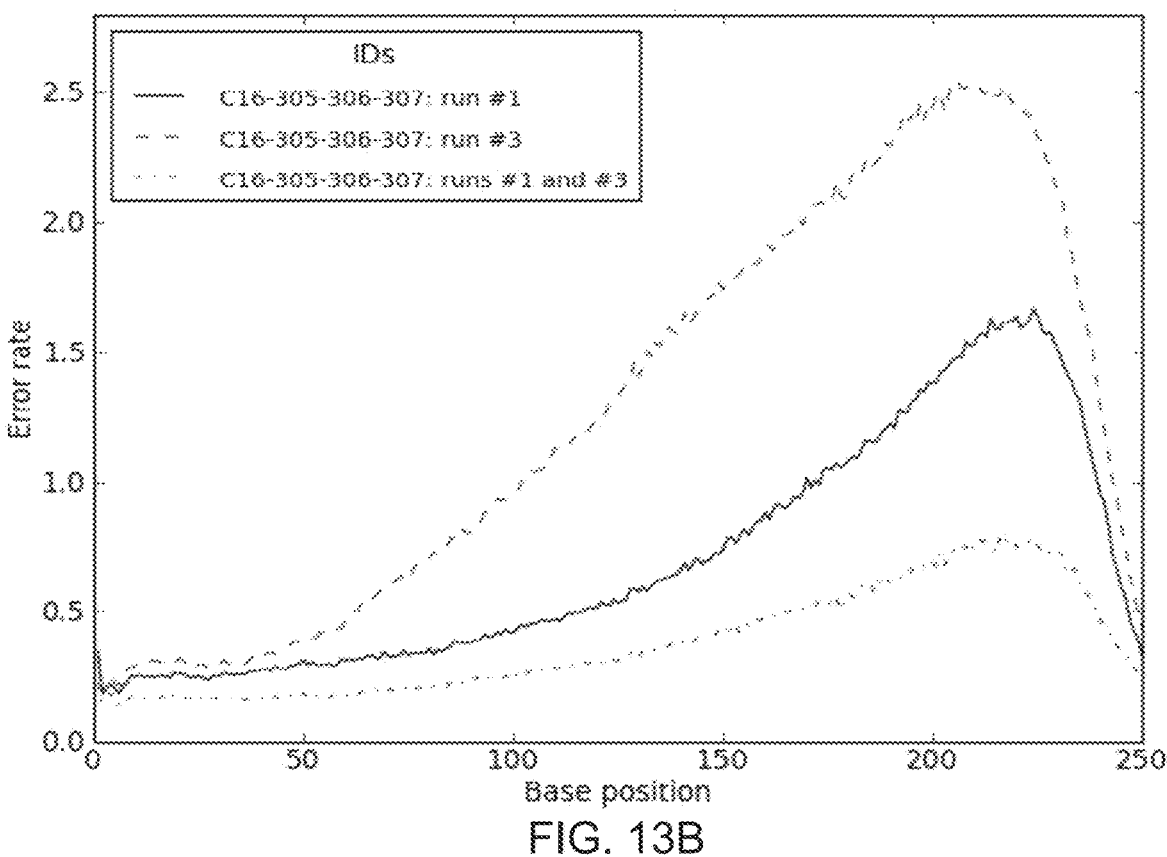
Figure 13C:
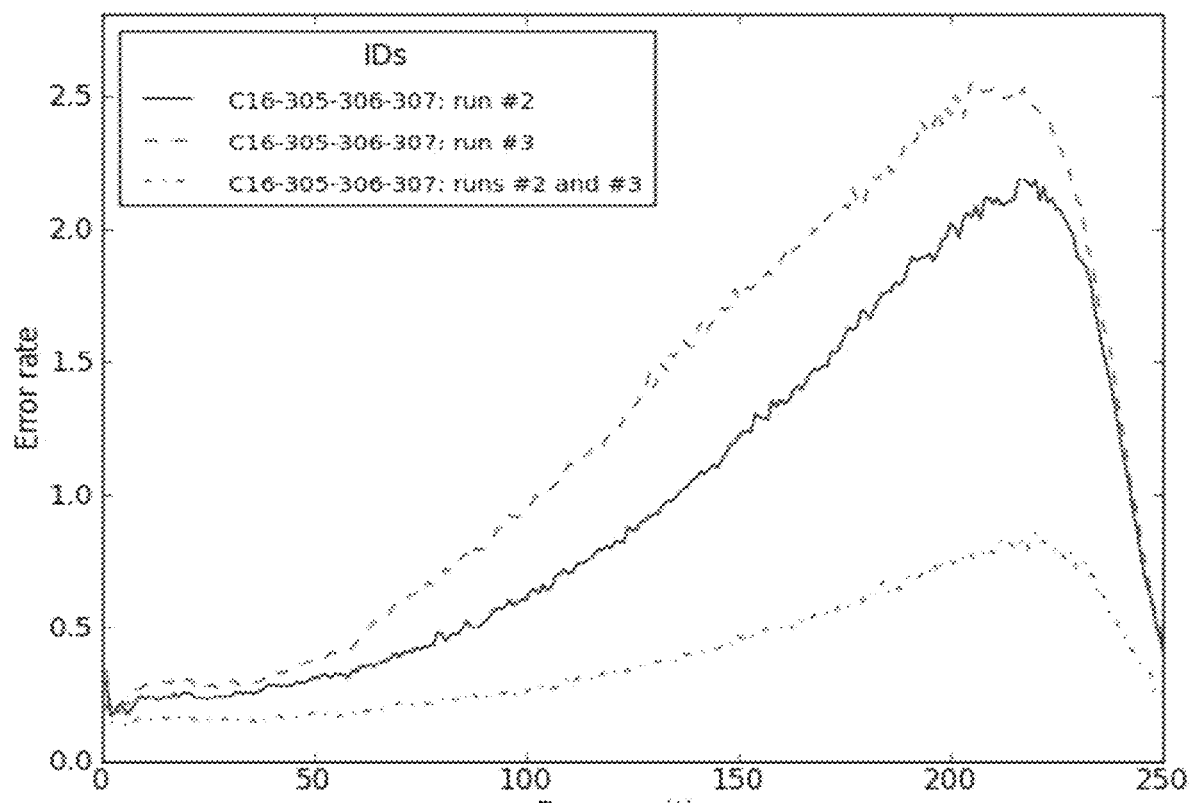
Figure 13D:
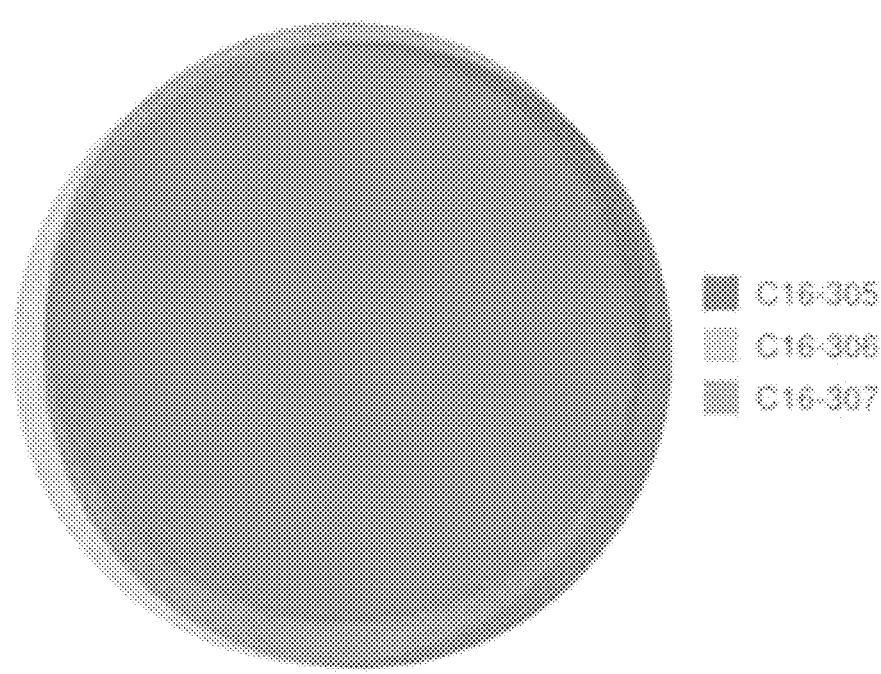
FIG. 13D illustrates a Venn diagram showing a degree of overlap in library reads.

FIGS. 13A-13C illustrate exemplary base error rates for pairs of runs selected from three repeat sequencing runs in a high template load situation. Here, run 1 was obtained using the SAMBA.GAFIEIRA flow ordering, run 2 was obtained using the SAMBA flow ordering, and run 3 was obtained using the CONTRADANZON flow ordering. In each figure, base error rates are shown for one of the runs taken alone, for the other run taken alone, and for the two runs combined. As shown, the base error rates for the combination are significantly reduced relative to that of the individual runs. FIG. 13D illustrates a Venn diagram showing a degree of overlap in library reads in each run. Here, there is a relatively high degree of overlap between reads of separate and combined runs, indicating that in most cases the experiment could benefit from read pairing, as library reads from the same wells were available to be paired. For example, read counts for runs 1, 2, and 3 are 546412, 534276, and 499356, respectively, and overlap counts for pairs 1-2, 1-3, and 2-3 are 503253, 483489, and 474352, respectively.

Figure 14A:
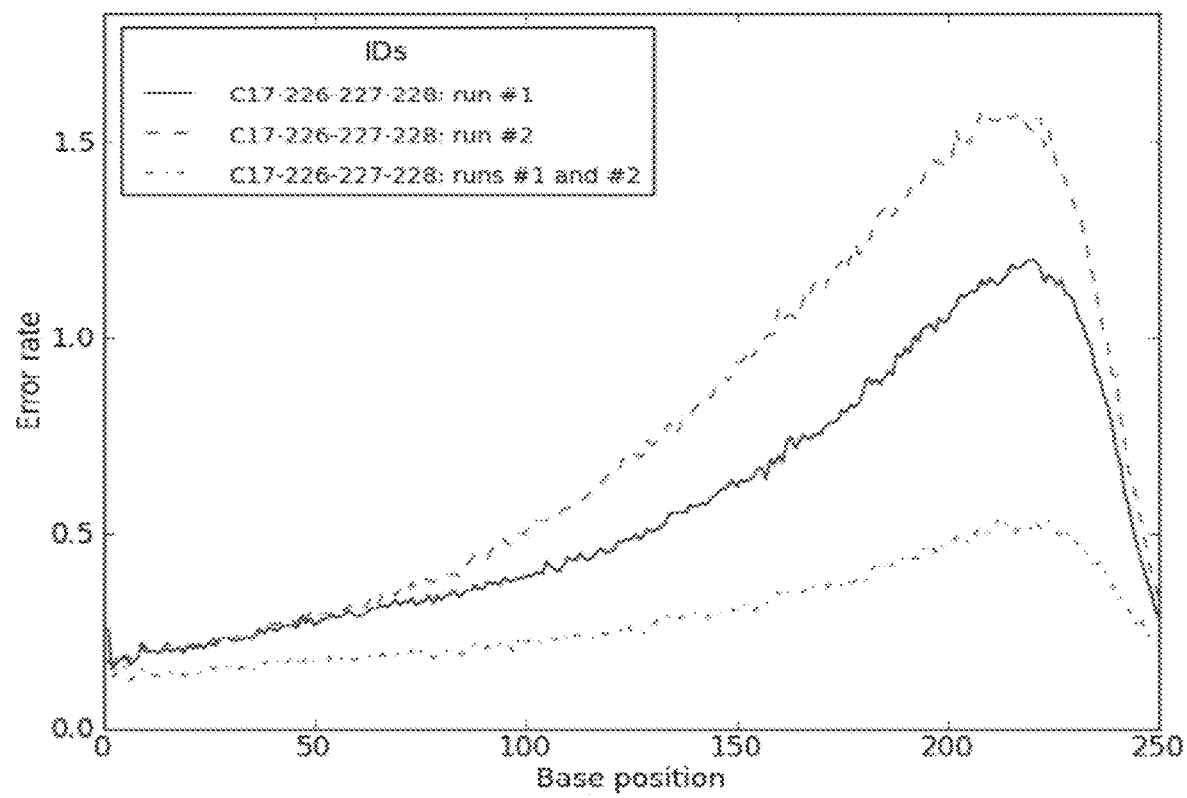
FIGS. 14A-14C illustrate exemplary base error rates for pairs of runs selected from three repeat sequencing runs in a high template load situation.
Figure 14B:
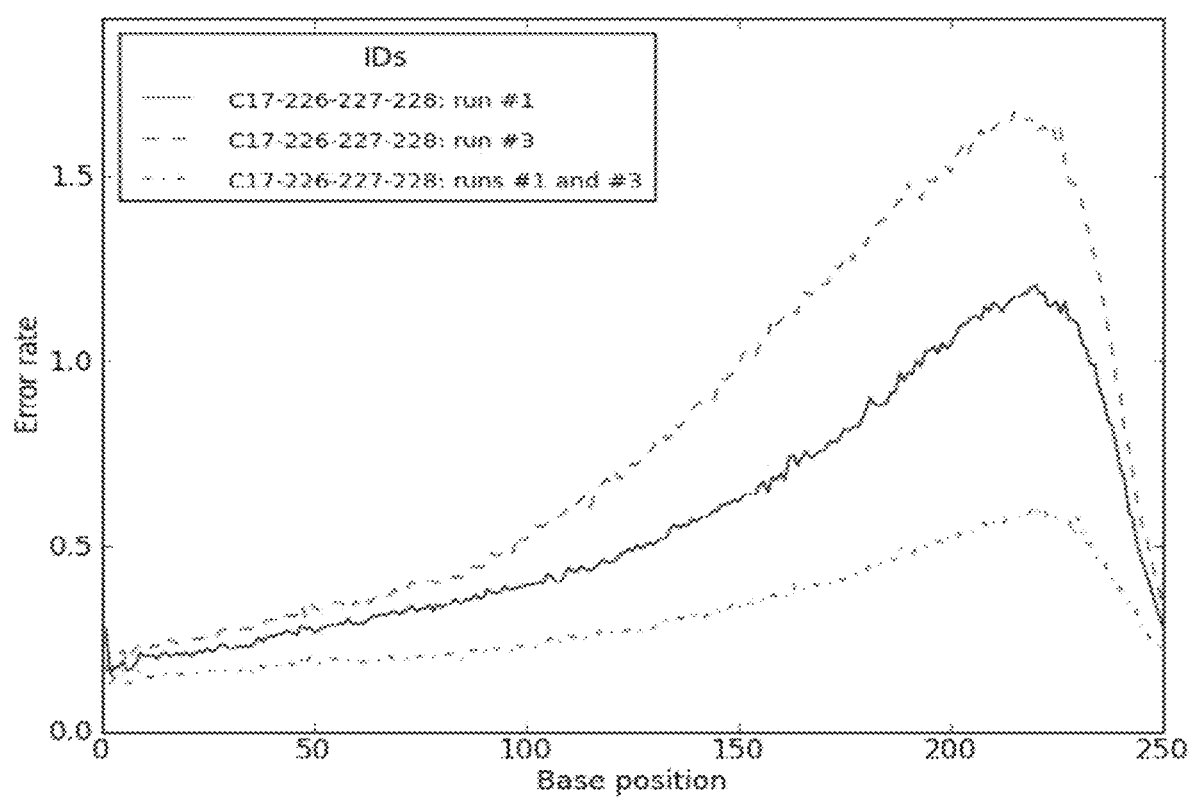
Figure 14C:
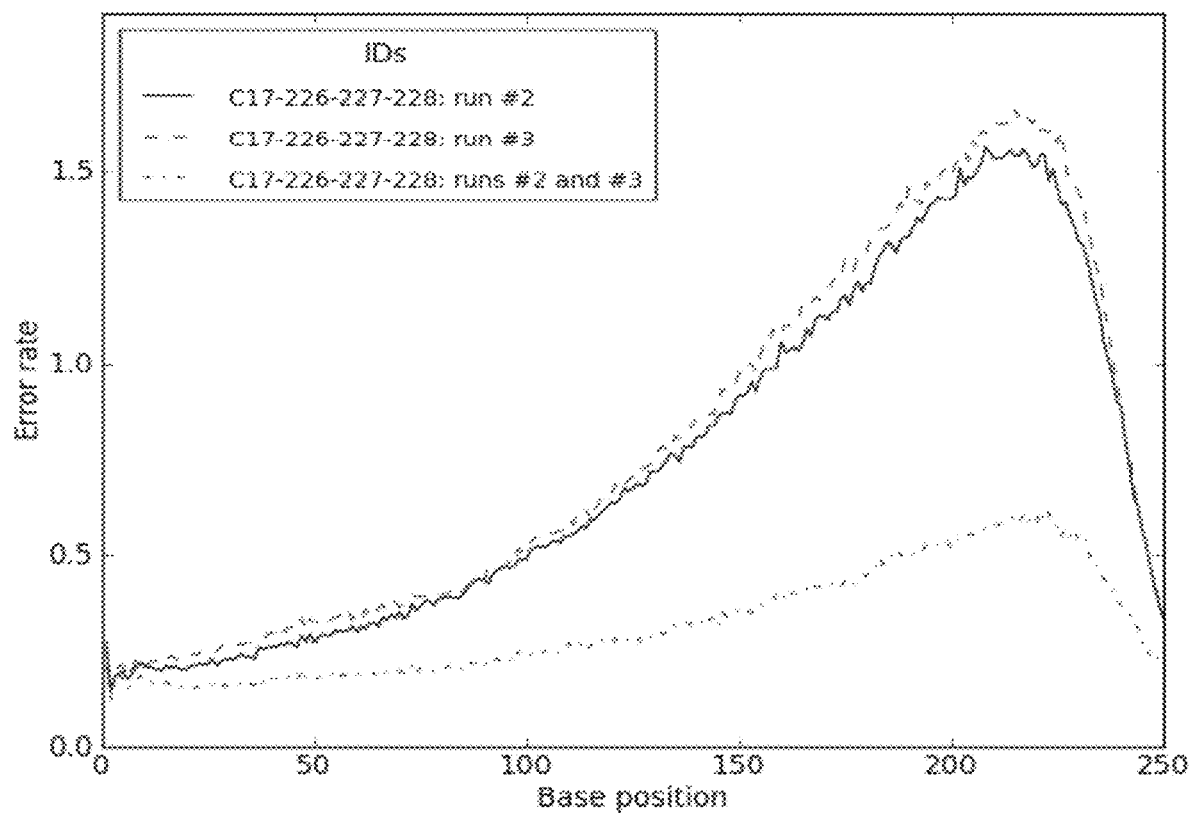
Figure 14D:
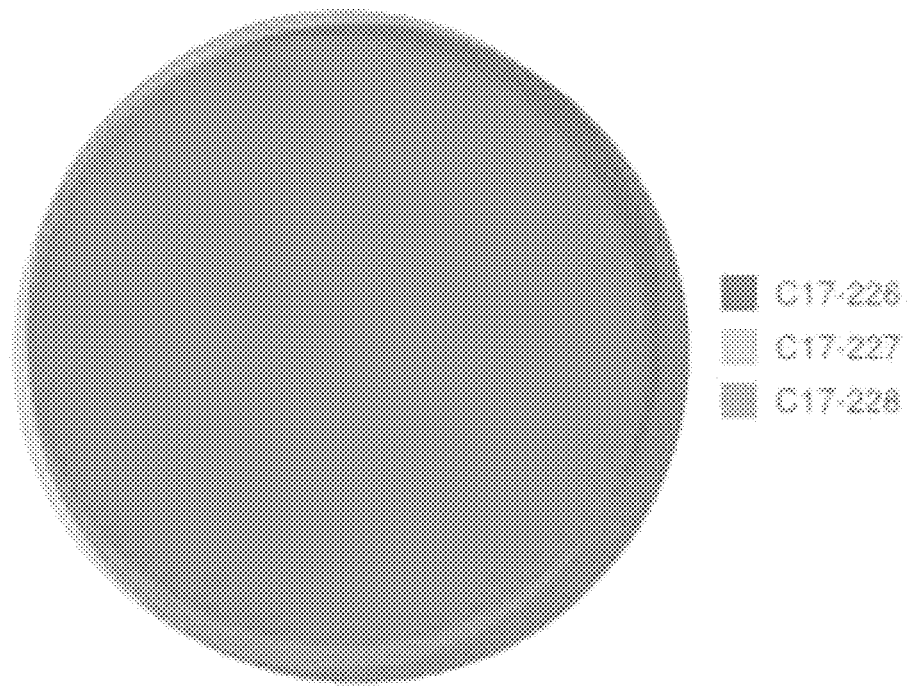
FIG. 14D illustrates a Venn diagram showing a degree of overlap in library reads.

FIGS. 14A-14C illustrate exemplary base error rates for pairs of runs selected from three repeat sequencing runs in a high template load situation. Here, run 1 was obtained using the CONTRADANZON flow ordering, run 2 was obtained using the SAMBA flow ordering, and run 3 was obtained using the SAMBA.GAFIEIRA flow ordering. In each figure, base error rates are shown for one of the runs taken alone, for the other run taken alone, and for the two runs combined. As shown, the base error rates for the combination are significantly reduced relative to that of the individual runs. FIG. 14D illustrates a Venn diagram showing a degree of overlap in library reads in each run. Here, there is again high degree of overlap between reads of separate and combined runs. For example, read counts for runs 1, 2, and 3 are 624663, 578158, and 578074, respectively, and overlap counts for pairs 1-2, 1-3, and 2-3 are 565908, 564131, and 546455, respectively.

Figure 15A:
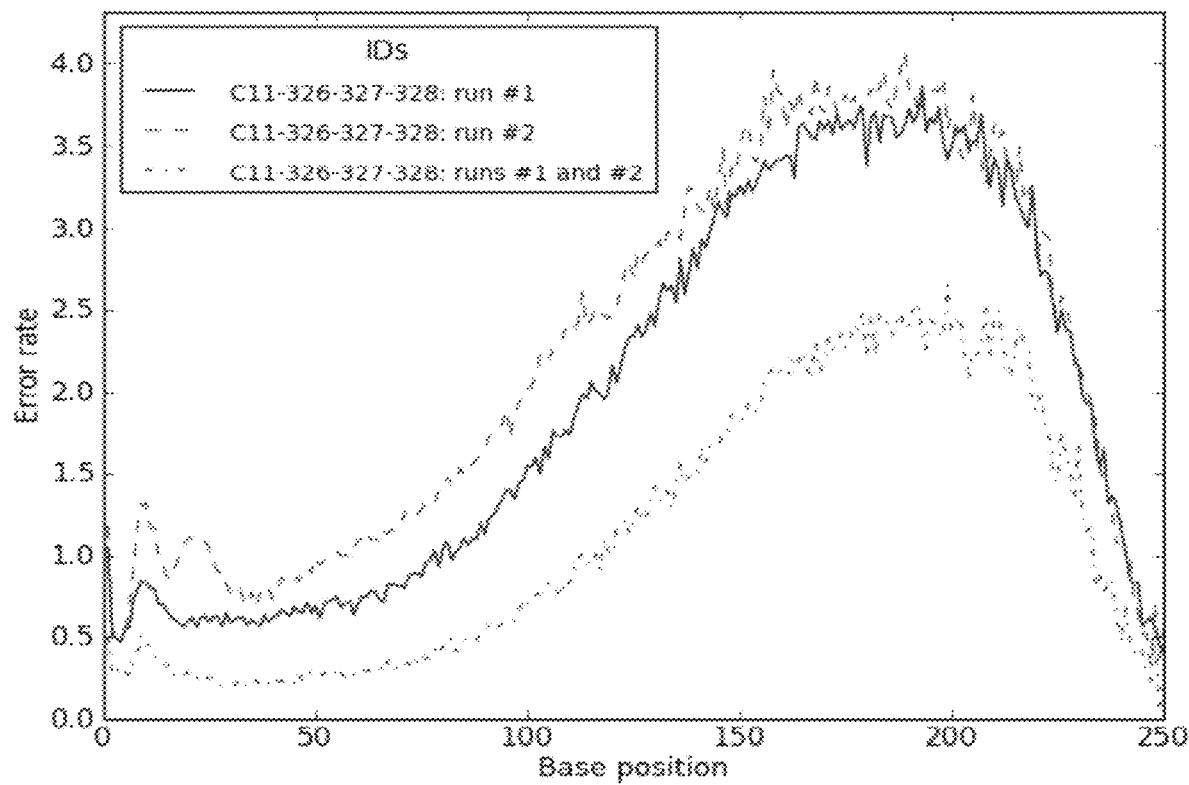
FIGS. 15A-15C illustrate exemplary base error rates for pairs of runs selected from three repeat sequencing runs in a low template load situation.
Figure 15B:
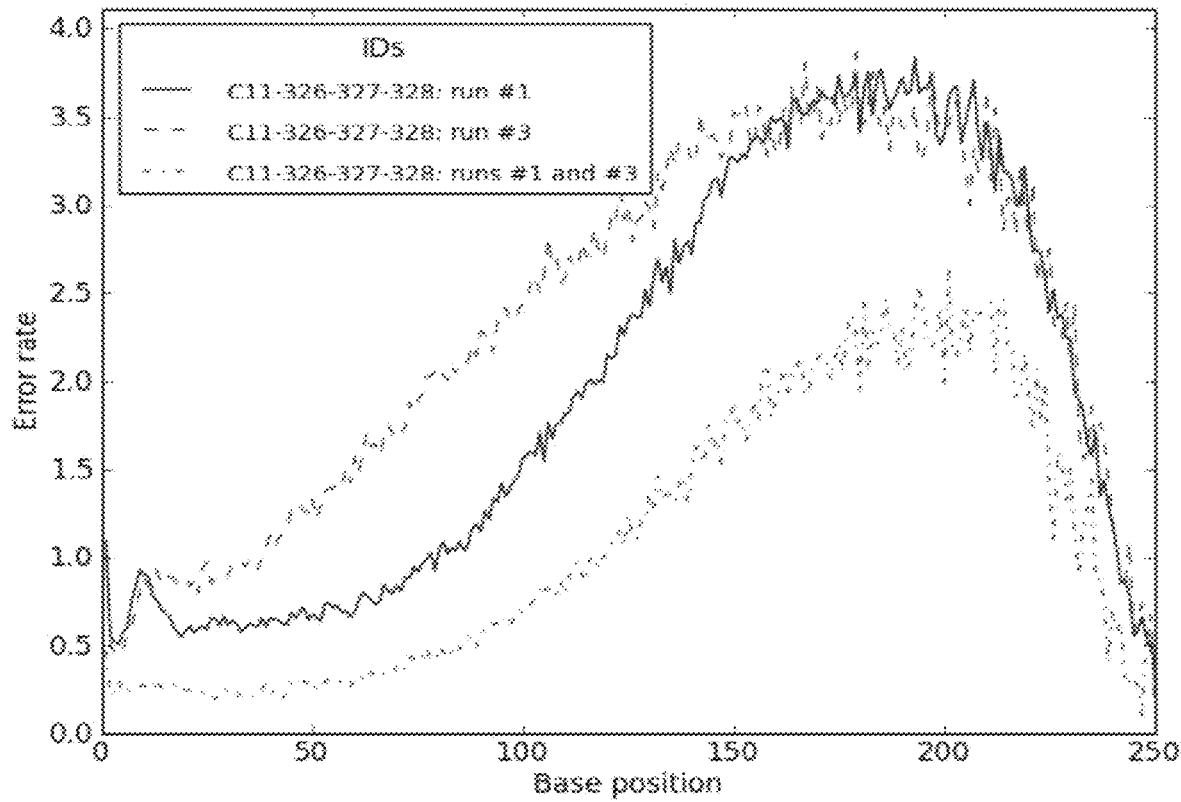
Figure 15C:
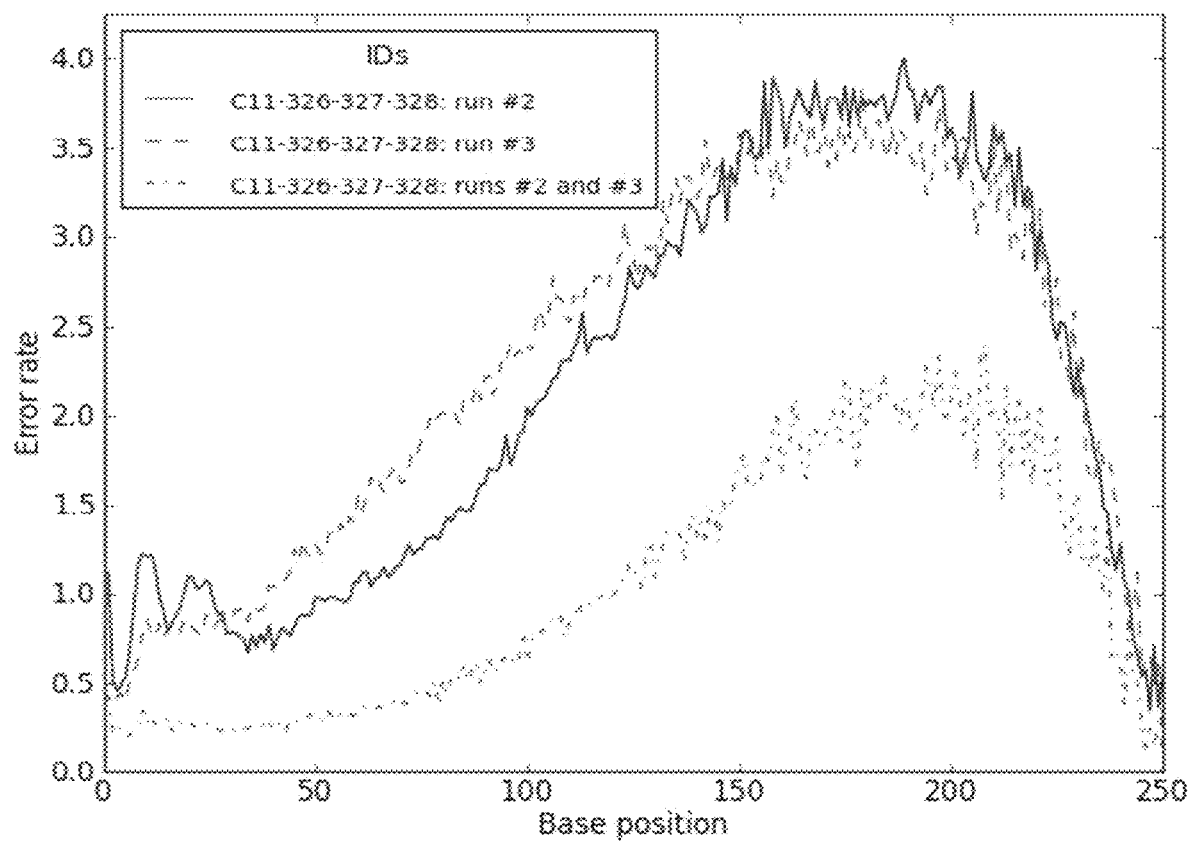
Figure 15D:
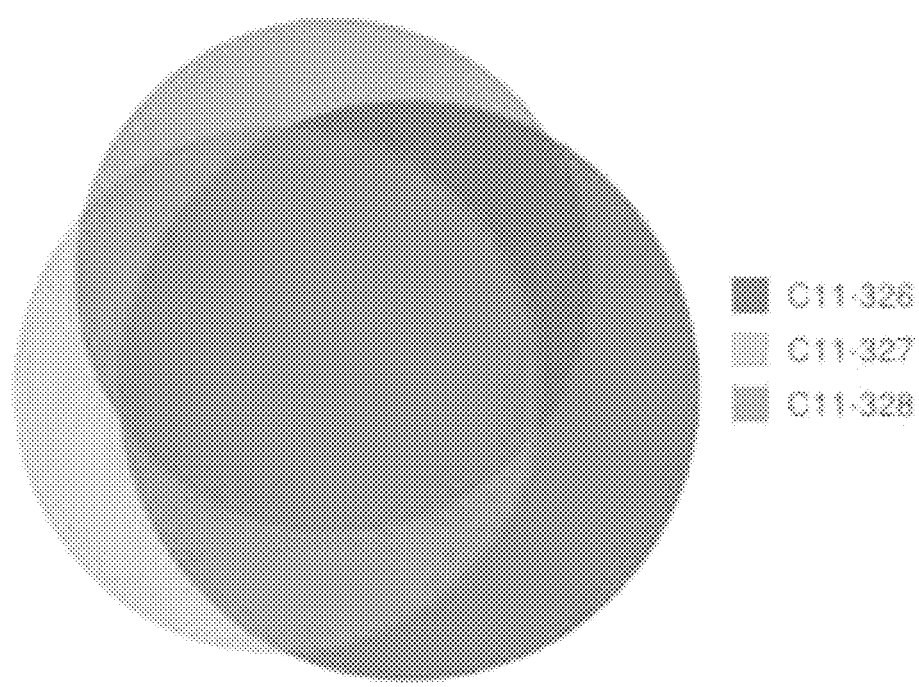
FIG. 15D illustrates a Venn diagram showing a degree of overlap in library reads.

FIGS. 15A-15C illustrate exemplary base error rates for pairs of runs selected from three repeat sequencing runs in a low template load situation. Here, run 1 was obtained using the SAMBA flow ordering, run 2 was obtained using the SAMBA.GAFIEIRA flow ordering, and run 3 was obtained using the CONTRADANZON flow ordering. In each figure, base error rates are shown for one of the runs taken alone, for the other run taken alone, and for the two runs combined. As shown, the base error rates for the combination are reduced relative to that of the individual runs, although not as significantly as in the high template load situation. FIG. 15D illustrates a Venn diagram showing a degree of overlap in library reads in each run. Here, there is some overlap, but not as much as in the high template load situation, indicating that in a significant number of cases the experiment would not benefit from read pairing as much, as library reads from the same wells are not as frequently available to be paired. For example, read counts for runs 1, 2, and 3 are 110343, 90851, and 86261, respectively, and overlap counts for pairs 1-2, 1-3, and 2-3 are 70576, 66734, and 61837, respectively.

Figure 16A:
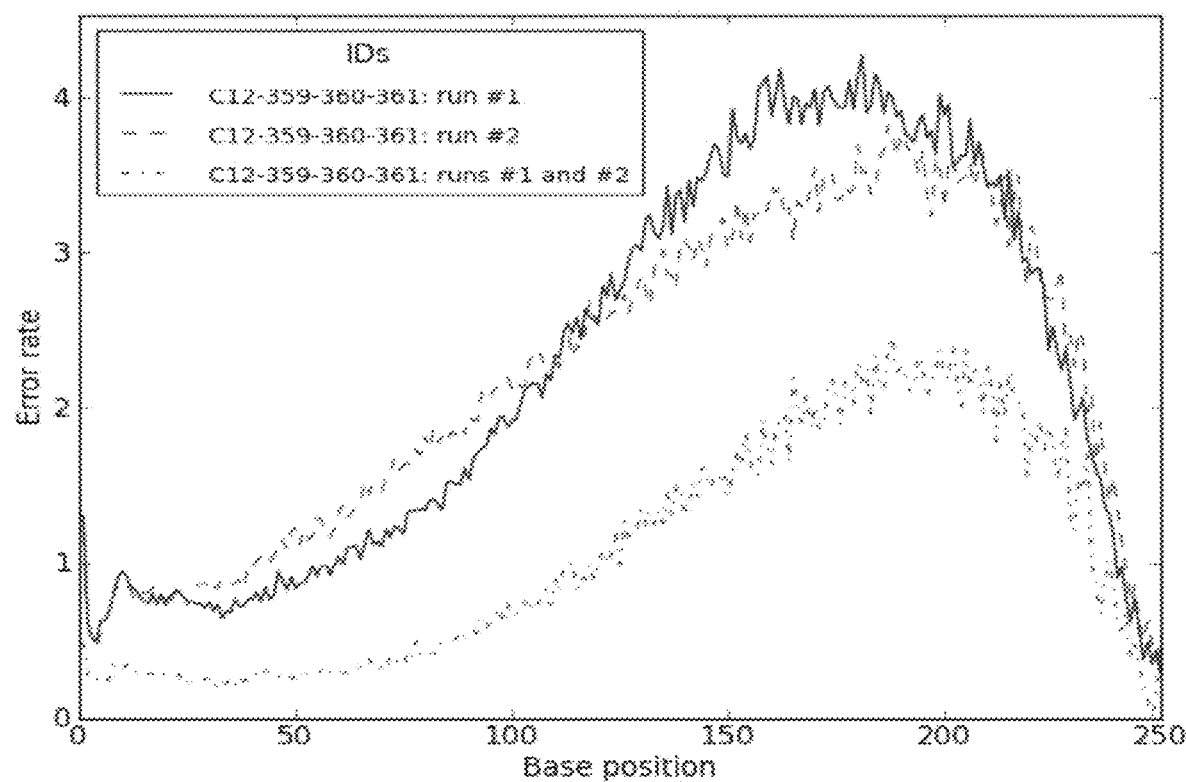
FIGS. 16A-16C illustrate exemplary base error rates for pairs of runs selected from three repeat sequencing runs in a low template load situation.
Figure 16B:
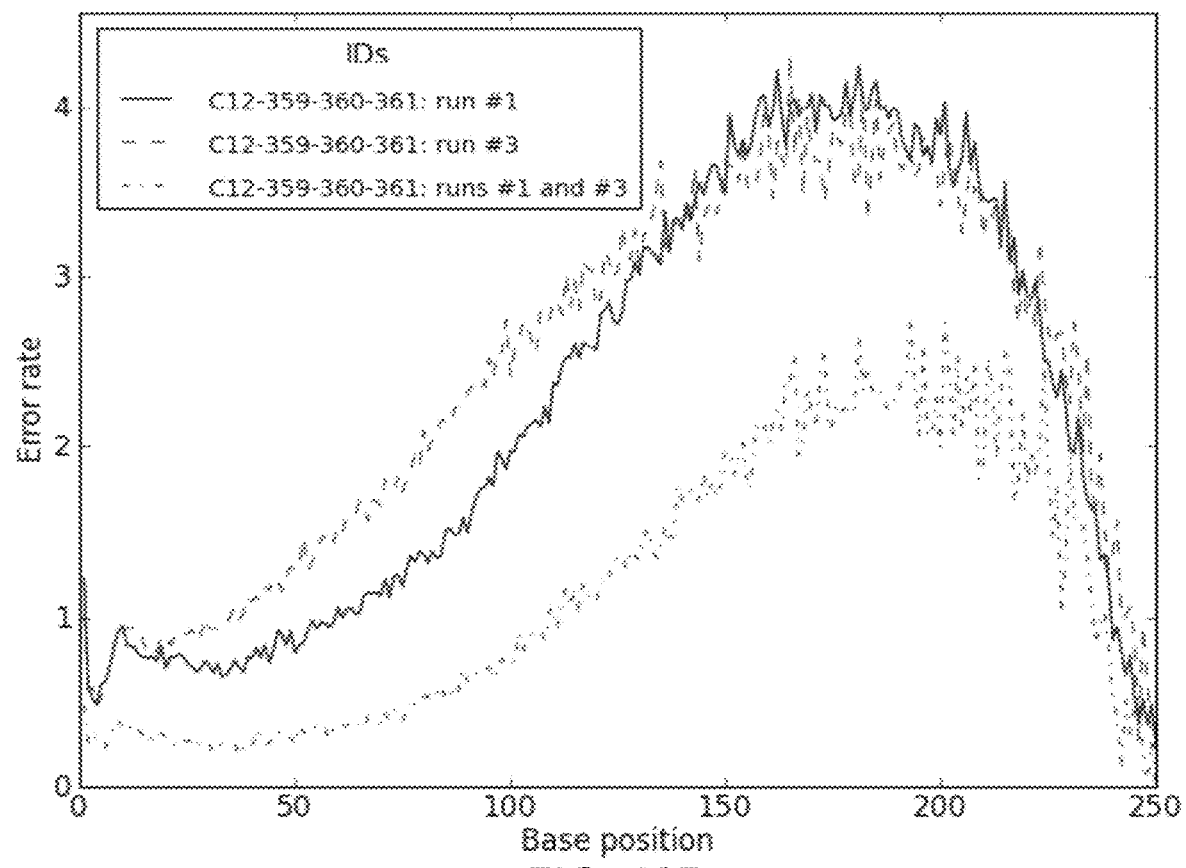
Figure 16C:
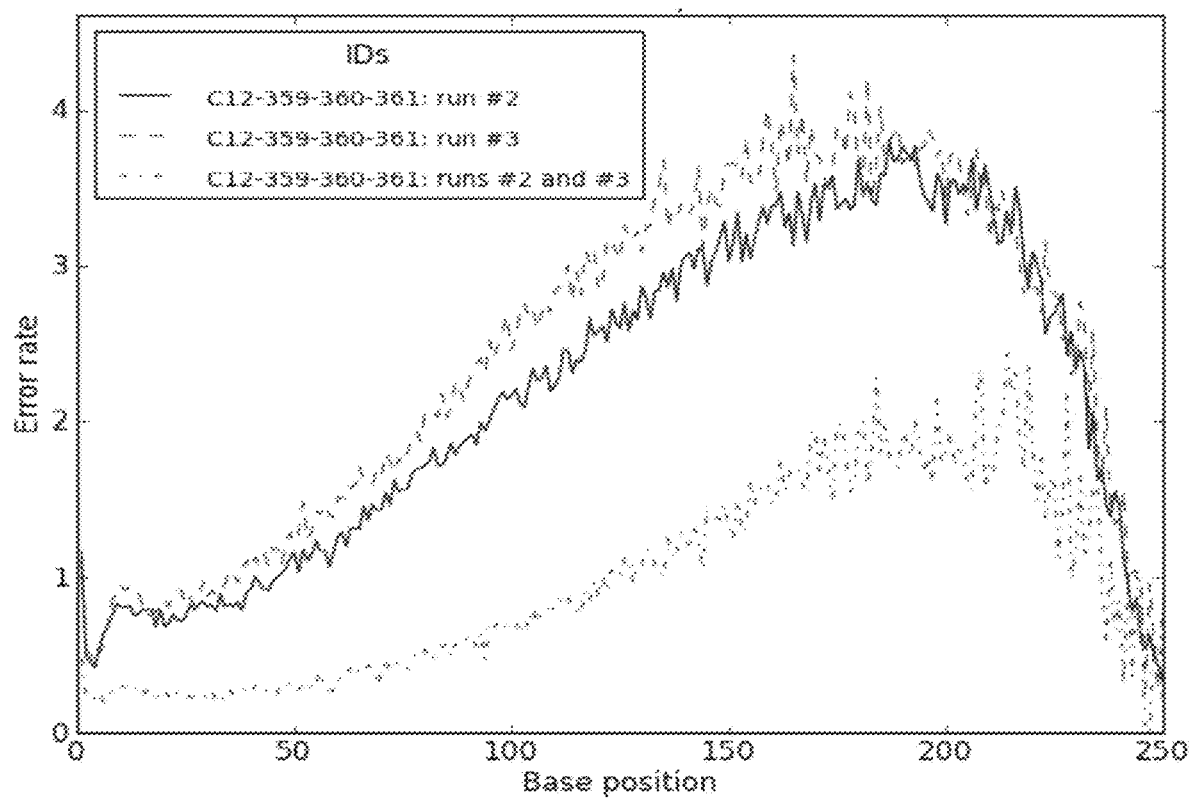
Figure 16D:
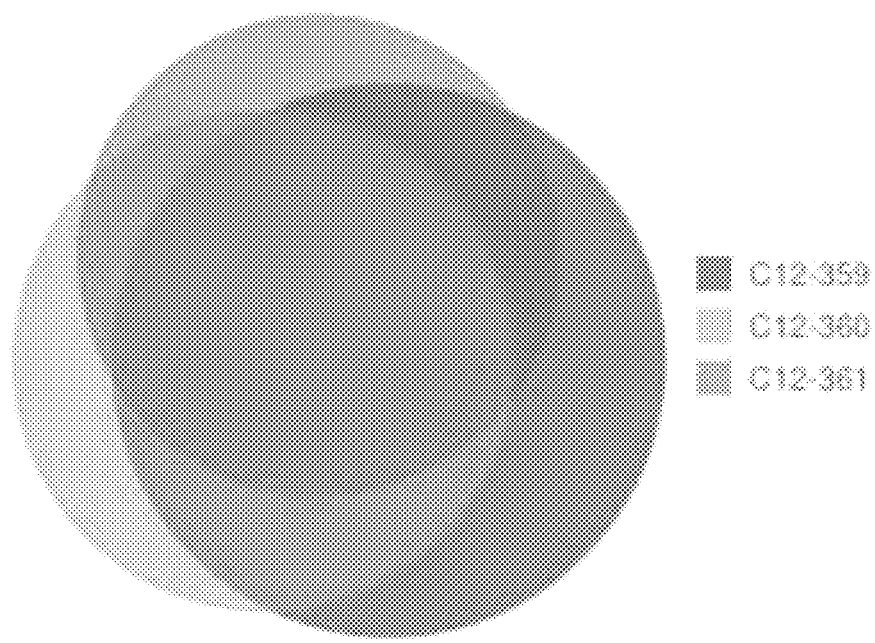
FIG. 16D illustrates a Venn diagram showing a degree of overlap in library reads.

FIGS. 16A-16C illustrate exemplary base error rates for pairs of runs selected from three repeat sequencing runs in a low template load situation. Here, run 1 was obtained using the SAMBA.GAFIEIRA flow ordering, run 2 was obtained using the CONTRADANZON flow ordering, and run 3 was obtained using the SAMBA flow ordering. In each figure, base error rates are shown for one of the runs taken alone, for the other run taken alone, and for the two runs combined. As shown, the base error rates for the combination are reduced relative to that of the individual runs, although not as significantly as in the high template load situation. FIG. 16D illustrates a Venn diagram showing a degree of overlap in library reads in each run. Here, there is again some overlap, but not as much as in the high template load situation. For example, read counts for runs 1, 2, and 3 are 98139, 80909, and 74085, respectively, and overlap counts for pairs 1-2, 1-3, and 2-3 are 63082, 59107, and 54557, respectively.

Figure 17A:
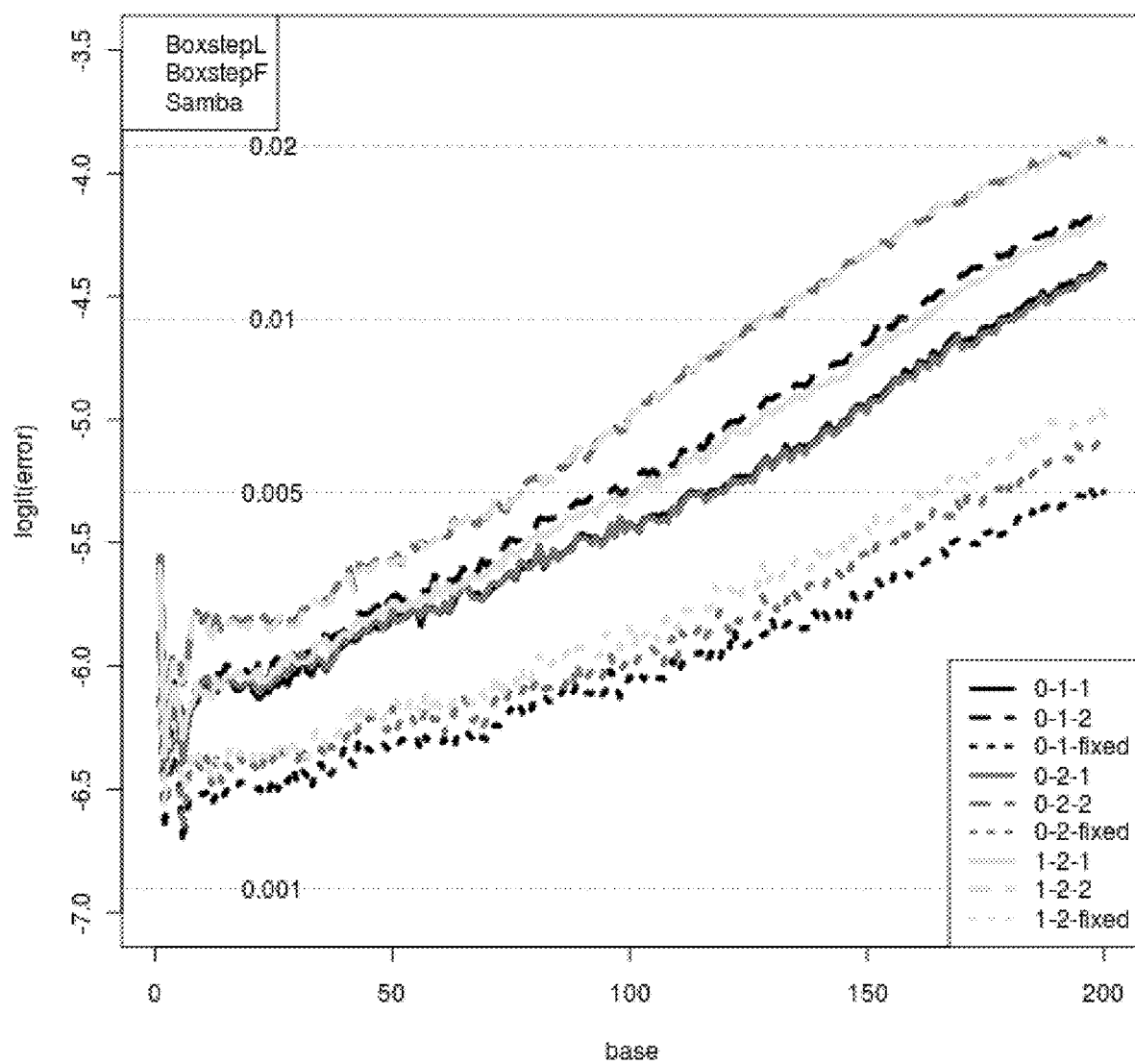
FIGS. 17A-17C illustrate logit-transformed error rates for compared repeat runs obtained using various flow orderings.
Figure 17B:
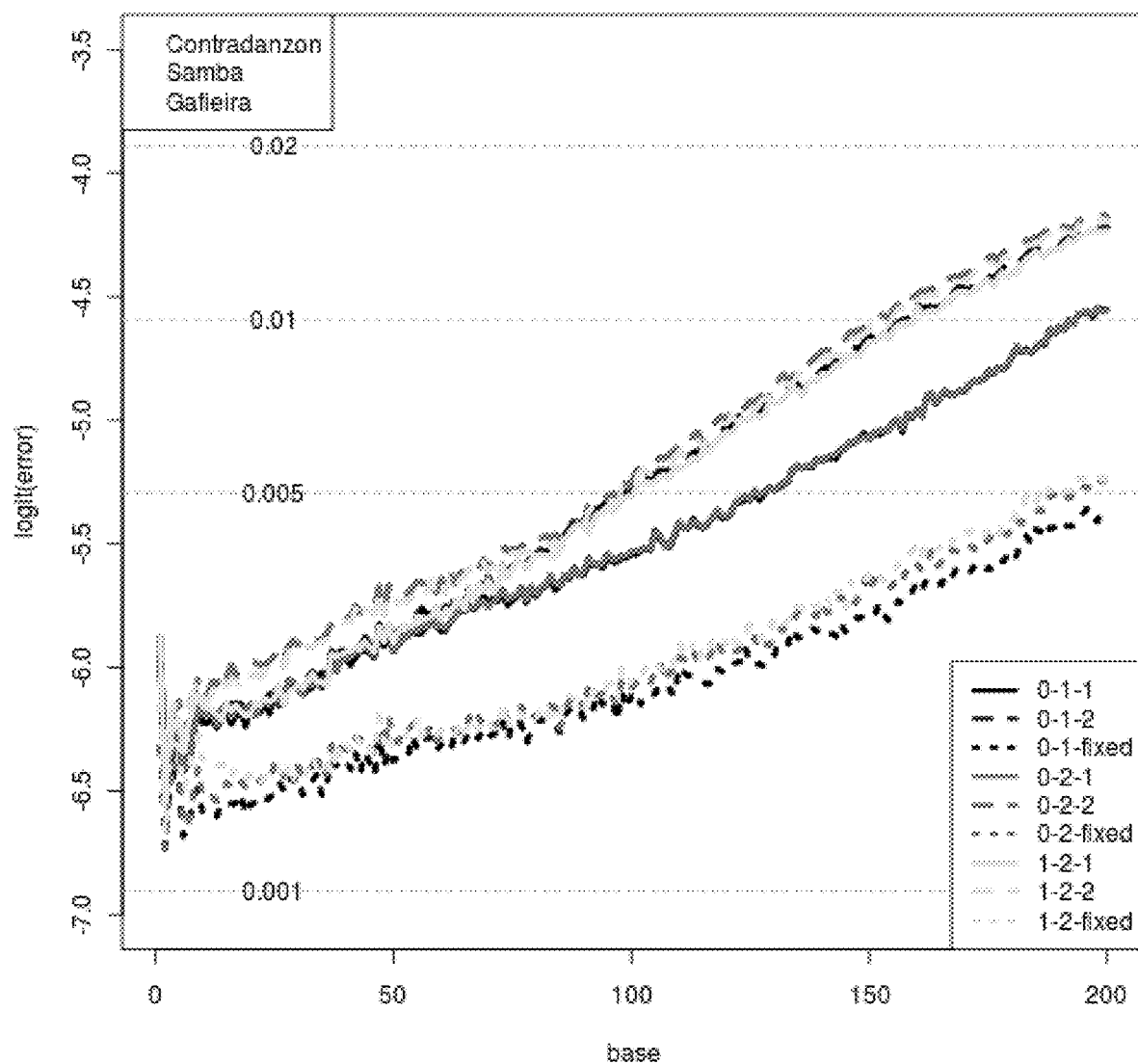
Figure 17C:
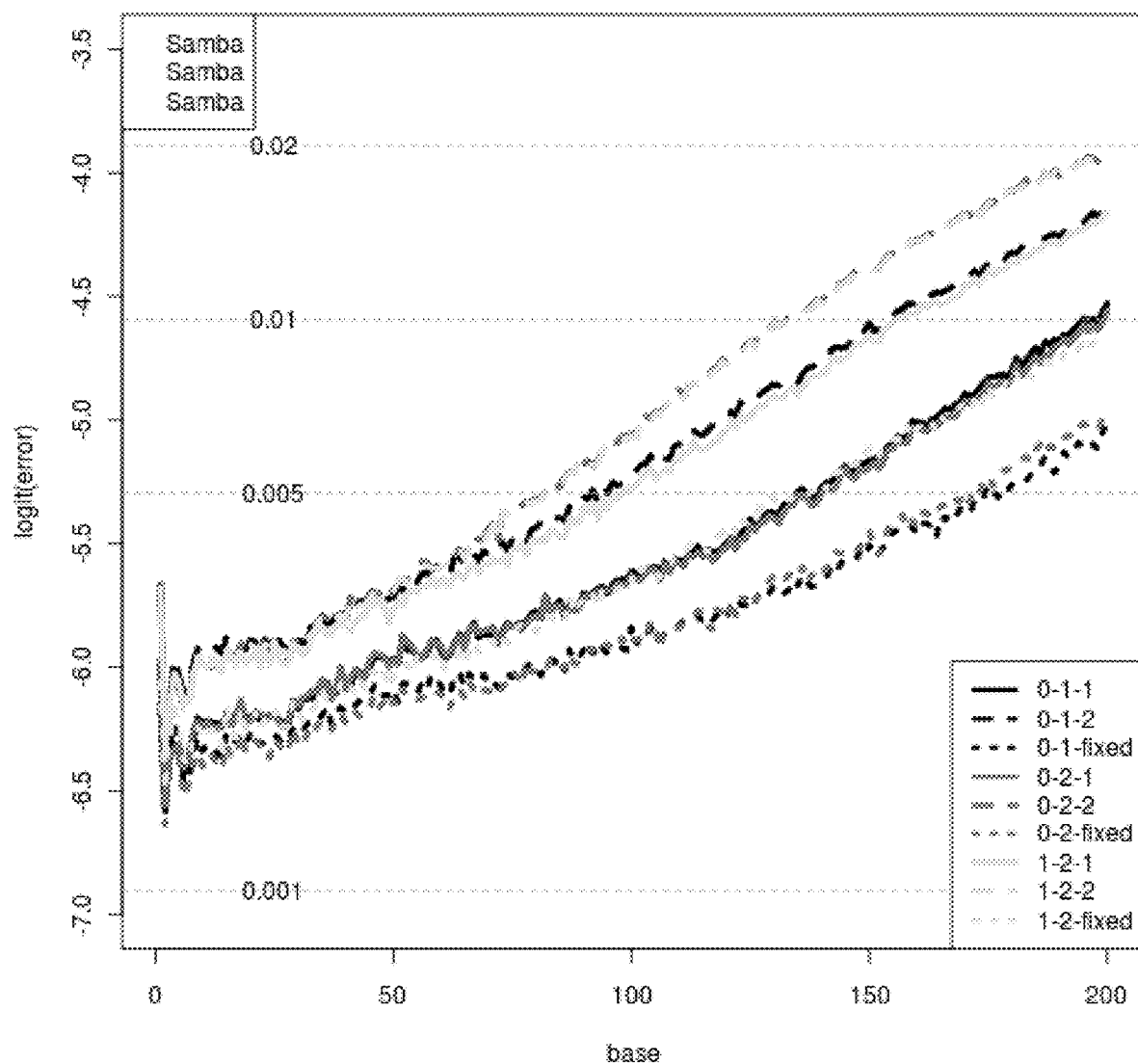

FIGS. 17A-17C illustrate logit-transformed error rates (which should turn into approximately parallel lines) for compared repeat runs obtained using various flow orderings. The dotted horizontal lines represent regular error rates. In the figures, the solid curves represent the first run in the pair, the dashed curve represents the second run in the pair, and the dotted line represents the first and second runs after pairing. The shades of grey represent first-to-second (darker grey, top three items in legend), first-to-third (medium grey, middle three items in legend), and second-to-third (lighter grey, bottom three items in legend) run comparisons. FIG. 17A shows that the use of BOXSTEP_LEAD, BOXSTEP_FOLLOW, and SAMBA in successive runs appears to significantly lower error rates as the dotted curves are below the solid curves, for example. FIG. 17B shows that use of CONTRADANZON, SAMBA, and SAMBA.GAFIEIRA in successive runs appear to significantly lower error rates also. Finally, FIG. 17C shows that SAMBA alone, used in all three runs, appears to lower error rates also, although possibly not quite as significantly. Based on performance of a relatively small number of experiments (10), it appears that first runs are generally better than second runs, and that second runs are generally better than third runs. It also appears that although pairing yields significant improvements, once pairing has occurred the effect of additional pairings may be smaller, so pairing only first and second runs may be both sufficient and efficient. Further, distinguishing among different orderings for ones best for repeat sequencing may be difficult as experiment-to-experiment variations may be larger than the variation due to use of particular flow orderings or combinations thereof.

According to an exemplary embodiment, there is provided a method for sequencing a nucleic acid template, comprising: (1) obtaining, using a sequencing instrument, two or more sets of flow signal intensities corresponding to two or more sequencing runs each generated using a pre-determined reagent flow ordering; (2) aligning the two or more sets of flow signal intensities into an alignment; (3) constructing a partial order graph using the two or more sets of flow signal intensities, the partial order graph representing the alignment; (4) generating a set of hypothetical consensus base sequences using the partial order graph; (5) searching within the set of hypothetical consensus base sequences and fitting against (a) a flow order and (b) flow signal intensities; and (6) selecting a best fitting consensus base sequence. The method may further comprise modifying the flow signal intensities, which may include averaging intensities. Searching may include finding as solution a sequence of bases for which two (or more) predicted set of values calculated under respective phasing models, for example, are jointly most or closely similar to some hypothetical measured set of values, under a least squares framework, for example. The solution may be found by searching or traversing possible sequences in various ways. For example, the search may be structured as a tree, such as discussed in Sikora et al., U.S. Pat. Appl. Publ. No. 2013/0090860, published Apr. 11, 2013, which is incorporated by reference herein in its entirety. The approach discussed in Sikora et al. may be modified to benefit from the diversity of information contained in different flow orders. Each predicated set of values may be generated for each read according to its individual phasing model/parameters. Then, based on the common solution, the reads may be individually normalized using adaptive normalization.

Figure 18:
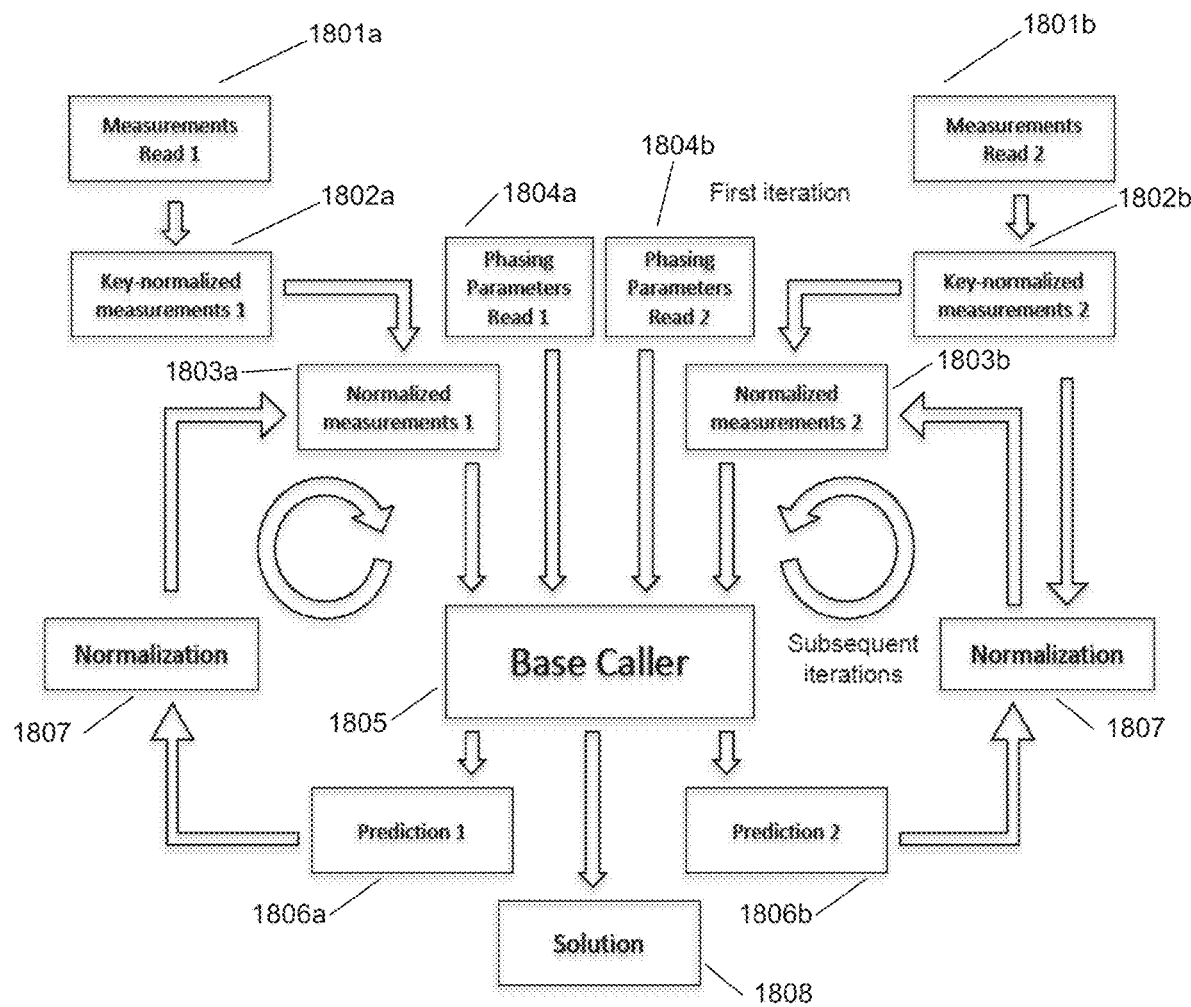
FIG. 18 illustrates a solver for making base calls in repeat sequencing.

FIG. 18 illustrates a workflow for a method for nucleic acid sequencing according to an exemplary embodiment. Sets of first and second measurements 1801a and 1801b, which may include measured data representative of numbers of nucleotide incorporations, for example, may initially be obtained. The first and second measurements 1801a and 1801b may be pre-normalized according to a known sequencing key into first and second key-normalized measurements 1802a and 1802b. For example, the measurements may all be divided by some common reference measurement (which may be an average intensity obtained for a known sequencing key, which may be known to represent 1-mer incorporations for the A, C, G, and T bases, for example). Other suitable pre-normalization methods may also be used. The first and second key-normalized measurements 1802a and 1802b may be used as first and second initial normalized measurements 1803a and 1803b, which may launch a first iteration of an iterative base calling process for each of the first and second initial normalized measurements 1803a and 1803b. In this first iteration and one or more subsequent iterations, a base caller engine or base caller 1805 may receive the first and second initial normalized measurements 1803a and 1803b along with first and second estimates 1804a and 1805b of one or more parameters of one or more predictive models, which may include phasing parameters in one or more predictive phasing models, for example. At each iteration, the base caller engine 1805 may output first and second predictions 1806a and 1806b, which may include predicted measurements that would be expected under the one or more predictive models if the nucleic acid to be sequenced had the sequence that the base caller would deem to be the base sequence solution at that iteration. At every iteration, a normalization engine 1807 may further normalize the first and second key-normalized measurements 1802a and 1802b, which may take into consideration the first and second predictions 1806a and 1806b, into more refined first and second normalized measurements 1803a and 1803b to be inputted again to the base caller engine 1805 in the next iteration. Normalization may be performed using any suitable normalization technique. At the last iteration, the base caller engine 1805 may output a joint solution 1808 for the two sets of measurements, which may be a sequence of bases A, C, G, and T for the measurements.

Any number of reads of the same base sequence can be solved jointly. The same principles and metrics described in Sikora et al., U.S. Pat. Appl. Publ. No. 2013/0090860, published Apr. 11, 2013 (including the path metric, the per-flow metric, the greedy metric, the scaled residual) may be used, except that in some cases the metrics may be replaced with averages (e.g., an averaged total residual, which is the average squared distance of the predictions to the observed ionograms) given the availability of multiple reads. The metrics may be computed from the values of all reads. Some extensions to notation, reflecting the presence of multiple reads, include: $L_i$ (number of flows for read i); $Y_{ij}$ (measured (observed) signal for read i at flow j); $Y_i=(Y_{i1}, Y_{i2}, \ldots, Y_{iL})$ (observed ionogram (signal from all flows) for read i); $X_i=(X_{i1}, X_{i2}, \ldots, X_{iL})$ (predicted ionogram (for the specific path, or partial sequence) for read i); $(a_i, b_i)$ (active window for read i); $f_i$ (in-phase flow for read i); and n (number of active reads). An "end of read" hypothesis may be evaluated on each read individually, so the number of active reads n, may change as the path increases in length or it may be different among different paths of the same length.

In an embodiment, a path metric for a path of length s may be expressed as Equation 1.1:

$$PathMetric(s) = PathMetric(s-1) + \sum_{i=1}^{n} \frac{ReadPathMetric_i(s) - ReadPathMetric_i(s-1)}{n}. \qquad \text{Eqn. 1.1}$$

In an embodiment, a read path metric may be a sum of (i) a sum of squared residuals before an active window and (ii) a sum of squared residuals for negative residuals within the active window. For example, such a read path metrics may be expressed as Equation 1.1a.

$$ReadPathMetric_i = \sum_{j=1}^{a_i-1}(Y_{ij}-X_{ij})^2 + \sum_{j=a_i}^{b_i}\begin{cases} 0 & \text{if } (Y_{ij}-X_{ij}) > 0 \\ (Y_{ij}-X_{ij})^2 & \text{if } (Y_{ij}-X_{ij}) < 0 \end{cases}. \qquad \text{Eqn. 1.1a}$$

A read path metric may also be expressed as Equation 1.2a, where δ and ε are real numbers, which may differ from zero.

$$ReadPathMetric = \sum_{j=1}^{a_i-1}(Y_{ij}-X_{ij})^2 + \sum_{j=a_i}^{b_i}\begin{cases} \delta & \text{if } (Y_{ij}-X_{ij}) > \varepsilon \\ (Y_{ij}-X_{ij})^2 & \text{if } (Y_{ij}-X_{ij}) < \varepsilon \end{cases}. \qquad \text{Eqn. 1.2a}$$

In an embodiment, the greedy decision metric may be the average of the greedy decision metrics of the individual active reads, which are given by a sum of (i) a product of an empirical constant and a sum of squared residuals for negative residuals within an active window and (ii) a sum of squared residuals for positive residuals within the active window but only before an in-phase flow. For example, such a greedy metrics may be expressed as Equation 2.1, where α is an empirical constant.

$$GreedyMetric_i = \alpha \sum_{j=a_i}^{b_i}\begin{cases} 0 & \text{if } (Y_{ij}-X_{ij}) > 0 \\ (Y_{ij}-X_{ij})^2 & \text{if } (Y_{ij}-X_{ij}) < 0 \end{cases} + \sum_{j=a_i}^{f_i-1}\begin{cases} (Y_{ij}-X_{ij})^2 & \text{if } (Y_{ij}-X_{ij}) > 0 \\ 0 & \text{if } (Y_{ij}-X_{ij}) < 0 \end{cases}. \qquad \text{Eqn. 2.1}$$

A greedy decision metric may also be expressed as Equation 2.2, where $\beta$, $\gamma$, $\delta$, and $\varepsilon$ are real numbers, which may differ from zero.

$$GreedyMetric_i = \alpha \sum_{j=a_i}^{b_i} \begin{cases} \beta & \text{if } (Y_{ij} - X_{ij}) > \gamma \\ (Y_{ij} - X_{ij})^2 & \text{if } (Y_{ij} - X_{ij}) < \gamma \end{cases} +$$

$$\sum_{j=a_i}^{f_i-1} \begin{cases} (Y_{ij} - X_{ij})^2 & \text{if } (Y_{ij} - X_{ij}) > \varepsilon \\ \delta & \text{if } (Y_{ij} - X_{ij}) < \varepsilon \end{cases}.$$

Eqn. 2.2

In an embodiment, a per-flow metric may be an average of the per-flow-metric of all reads that have been active on this path, where the per-flow metric for a read is given by a weighted sum of (i) a path metric as described above and (ii) a greedy decision metric as described above. For example, the per-flow metric may be expressed as Equation 3.1, where A may be substantially equal to $1/f_i$ and B may be substantially equal to $0.5/f_i$, where $f_i$ denotes the in-phase flow.

$$PerFlowMetric_i = A(PathMetric_i) + B(GreedyMetric_i).$$  Eqn. 3.1

Table 1 shows examples of the increase in the number of long high quality sequences using repeat sequencing and joint tree-based solving. The input set of wells to the base caller in each case is the set of wells that are classified as library beads in both runs. As shown, using joint tree-based solving based on two repeat sequencing runs can show significant increases in the number of long high quality sequences relative to sequencing using only a single run.

TABLE 1

Number of High Quality Reads for Two Sequencing Runs Taken Alone and Jointly

|  | Run 1 | Run 2 | Runs 1 & 2 Jointly |
|---|---|---|---|
| 100Q17 | 521412 | 510074 | 532583 |
| 200Q20 | 421576 | 322719 | 470711 |
| 200Q47 | 245928 | 158645 | 306463 |
| 250Q47 | 39735 | 21786 | 65142 |

Figure 19:
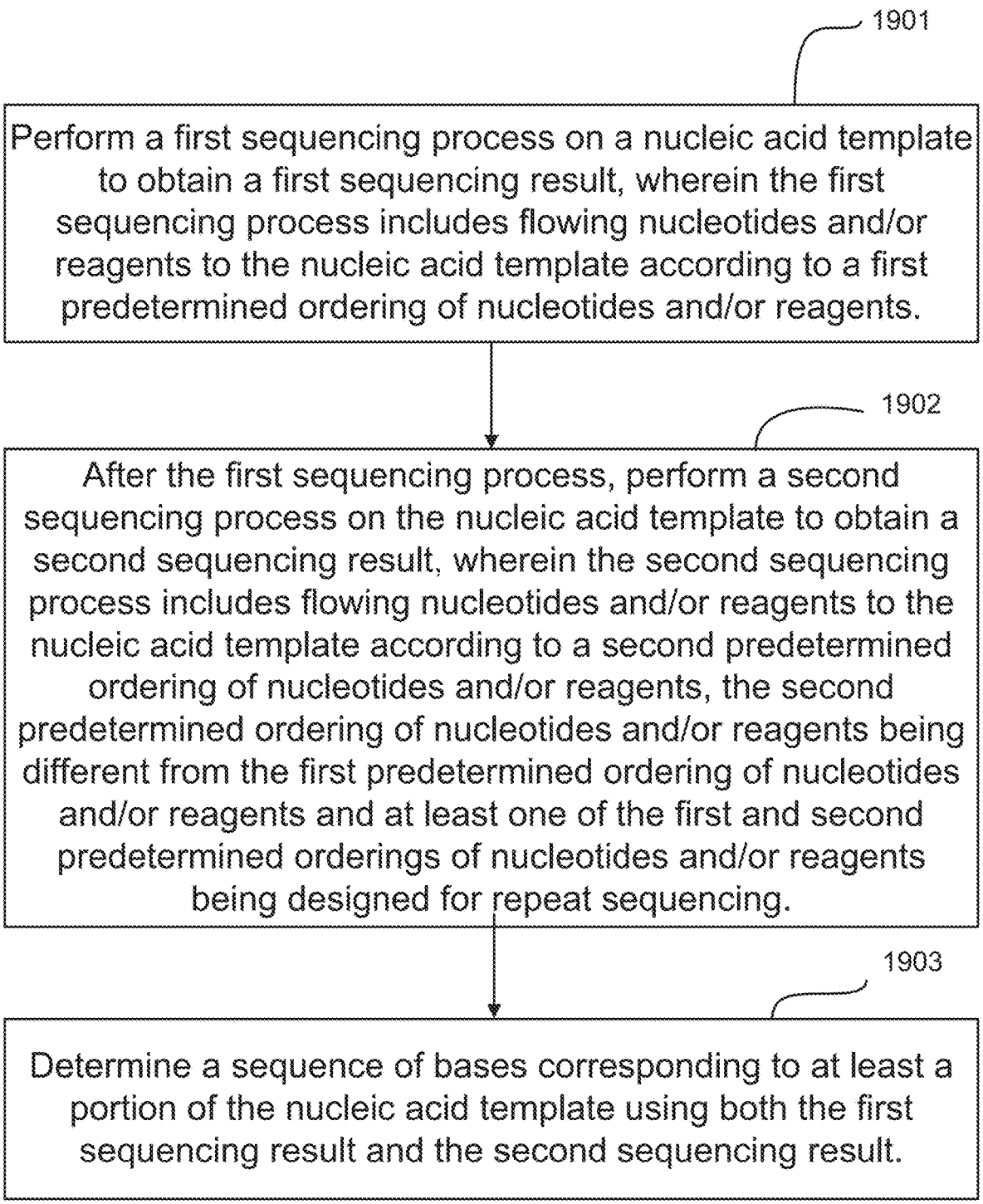
FIG. 19 illustrates an exemplary method for repeat sequencing.

FIG. 19 illustrates an exemplary method for sequencing a nucleic acid. In step 1901, a first sequencing process is performed on a nucleic acid template to obtain a first sequencing result, wherein the first sequencing process includes flowing nucleotides and/or reagents to the nucleic acid template according to a first predetermined ordering of nucleotides and/or reagents. In step 1902, after the first sequencing process, a second sequencing process is performed on the nucleic acid template to obtain a second sequencing result, wherein the second sequencing process includes flowing nucleotides and/or reagents to the nucleic acid template according to a second predetermined ordering of nucleotides and/or reagents, the second predetermined ordering of nucleotides and/or reagents being different from the first predetermined ordering of nucleotides and/or reagents and at least one of the first and second predetermined orderings of nucleotides and/or reagents being designed for repeat sequencing. In step 1903, a sequence of bases corresponding to at least a portion of the nucleic acid template is determined using both the first sequencing result and the second sequencing result.

Figure 20:
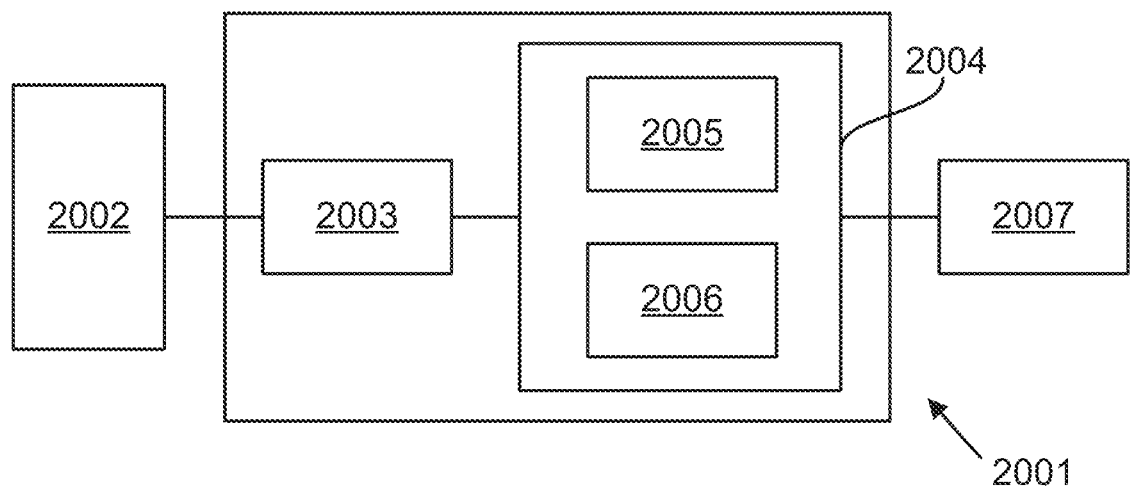
FIG. 20 illustrates an exemplary system for repeat sequencing.

FIG. 20 illustrates a system 2001 for nucleic acid sequencing according to an exemplary embodiment. The system includes a reactor array 2002; a reader board 2003; a computer and/or server 2004, which includes a CPU 2005 and a memory 2006; and a display 2007, which may be internal and/or external. One or more of these components may be used to perform or implement one or more aspects of the exemplary embodiments described herein.

According to an exemplary embodiment, there is provided a method for sequencing a nucleic acid template, including: performing a first sequencing process on the nucleic acid template to obtain a first sequencing result, wherein the first sequencing process includes flowing nucleotides and/or reagents to the nucleic acid template according to a first predetermined ordering of nucleotides and/or reagents; after the first sequencing process, performing a second sequencing process on the nucleic acid template to obtain a second sequencing result, wherein the second sequencing process includes flowing nucleotides and/or reagents to the nucleic acid template according to a second predetermined ordering of nucleotides and/or reagents, wherein the second predetermined ordering of nucleotides and/or reagents is different from the first predetermined ordering of nucleotides and/or reagents and wherein at least one of the first and second predetermined orderings of nucleotides and/or reagents is designed for repeat sequencing; and determining a sequence of bases corresponding to at least a portion of the nucleic acid template using both the first sequencing result and the second sequencing result.

In such a method, at least one of the first and second predetermined orderings of nucleotides and/or reagents may include a combination of Kautz sequences generated using all possible dimers of A, C, G, and T. At least one of the first and second predetermined orderings of nucleotides and/or reagents may include a combination of loops through a Kautz graph of possible dimers of A, C, G, and T. At least one of the first and second predetermined orderings of nucleotides and/or reagents may include a series of a predetermined number of predetermined permutations of a combination of at least three loops through a Kautz graph of possible dimers of A, C, G, and T. The series of a predetermined number of predetermined permutations of a combination of at least three loops may include a first loop, followed by a second loop, followed by a third loop, followed by the first loop, followed by the third loop, followed by the second loop.

In such a method, at least one of the first and second predetermined orderings of nucleotides and/or reagents may include a first 4-flow block of flows comprising a first 4-flow permutation of flows A, C, G, and T, followed by a predetermined number of repeats of a first 3- flow permutation of a first set of three flows selected from A, C, G, and T, followed by an isolated flow of the nucleotide not in the first set. The isolated flow of the nucleotide not in the first set may be followed by a second 4-flow permutation of flows A, C, G, and T different than the first 4-flow permutation, followed by a predetermined number of repeats of a second 3-flow permutation of a second set of three flows selected from A, C, G, and T different than the first set, followed by an isolated flow of the nucleotide not in the second set. The isolated flow of the nucleotide not in the second set may be followed by a third 4-flow permutation of flows A, C, G, and T different than the first and second 4-flow permutations, followed by a predetermined number of repeats of a third 3-flow permutation of a third set of three flows selected from A, C, G, and T different than the first and second sets, followed by an isolated flow of the nucleotide not in the third set. The isolated flow of the nucleotide not in the third set may be followed by a fourth 4-flow permutation of flows A, C, G, and T different than the first, second, and third 4-flow permutations, followed by a predetermined number of repeats of a fourth 3-flow permutation of a fourth set of three flows selected from A, C, G, and T different than the first, second, and third sets, followed by an isolated flow of the nucleotide not in the fourth set. At least one of the first and second predetermined orderings of nucleotides and/or reagents may include a pattern selected to delay and/or rotate flows.

In such a method, at least one of the first and second predetermined orderings of nucleotides and/or reagents may be selected from a combination of building blocks designed for complementary sequencing in both directions. Both the first and second predetermined orderings of nucleotides and/or reagents may include a combination of Kautz sequences generated using all possible dimers of A, C, G, and T. Both the first and second predetermined orderings of nucleotides and/or reagents may include a combination of loops through a Kautz graph of possible dimers of A, C, G, and T. Both the first and second predetermined orderings of nucleotides and/or reagents may include a first 4-flow block of flows comprising a first 4-flow permutation of flows A, C, G, and T, followed by a predetermined number of repeats of a first 3-flow permutation of a first set of three flows selected from A, C, G, and T, followed by an isolated flow of the nucleotide not in the first set.

In such a method, determining the sequence of bases may include: generating sets of candidate sequences of bases for each of first sequencing result and the second sequencing result using one or more metrics adapted to associate a score or penalty to the candidate sequences of bases; and selecting from the generated sequences of bases the candidate sequence leading to a highest score or a lowest penalty as corresponding to the correct sequence for the nucleic acid template. Generating the sets of candidate sequences of bases for each of first sequencing result and the second sequencing result may include generating a tree-based data structure comprising sets of partial paths corresponding to candidate sequences undergoing expansion in a stepwise manner one base at a time. Generating the tree-based data structure may include determining a predicted signal for each partial path and evaluating a distance between the predicted signal and an observed or measured signal. The one or more metrics may include a metric that is a function of the distance between the predicted signal and the observed or measured signal.

According to an exemplary embodiment, there is provided a system for sequencing a nucleic acid template, including: a machine-readable memory; and a processor configured to execute machine-readable instructions, which, when executed by the processor, cause the system to perform a method including: performing a first sequencing process on the nucleic acid template to obtain a first sequencing result, wherein the first sequencing process includes flowing nucleotides and/or reagents to the nucleic acid template according to a first predetermined ordering of nucleotides and/or reagents; after the first sequencing process, performing a second sequencing process on the nucleic acid template to obtain a second sequencing result, wherein the second sequencing process includes flowing nucleotides and/or reagents to the nucleic acid template according to a second predetermined ordering of nucleotides and/or reagents, wherein the second predetermined ordering of nucleotides and/or reagents is different from the first predetermined ordering of nucleotides and/or reagents and wherein at least one of the first and second predetermined orderings of nucleotides and/or reagents is designed for repeat sequencing; and determining a sequence of bases corresponding to at least a portion of the nucleic acid template using both the first sequencing result and the second sequencing result.

According to an exemplary embodiment, there is provided a non-transitory machine-readable storage medium including instructions which, when executed by a processor, cause the processor to perform a method for nucleic acid sequencing including: performing a first sequencing process on the nucleic acid template to obtain a first sequencing result, wherein the first sequencing process includes flowing nucleotides and/or reagents to the nucleic acid template according to a first predetermined ordering of nucleotides and/or reagents; after the first sequencing process, performing a second sequencing process on the nucleic acid template to obtain a second sequencing result, wherein the second sequencing process includes flowing nucleotides and/or reagents to the nucleic acid template according to a second predetermined ordering of nucleotides and/or reagents, wherein the second predetermined ordering of nucleotides and/or reagents is different from the first predetermined ordering of nucleotides and/or reagents and wherein at least one of the first and second predetermined orderings of nucleotides and/or reagents is designed for repeat sequencing; and determining a sequence of bases corresponding to at least a portion of the nucleic acid template using both the first sequencing result and the second sequencing result.

According to various embodiments, one or more features of any one or more of the above-discussed teachings and/or embodiments may be performed or implemented using appropriately configured and/or programmed hardware and/or software elements.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various embodiments, one or more features of any one or more of the above-discussed teachings and/or embodiments may be performed or implemented using appropriately configured and/or programmed non-transitory machine-readable medium or article that may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or rewriteable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and nonvolatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various embodiments, one or more features of any one or more of the above-discussed teachings and/or embodiments may be performed or implemented at least partly using a distributed, clustered, remote, or cloud computing resource.

According to various embodiments, one or more features of any one or more of the above-discussed teachings and/or embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, Pascal, Basic, Fortran, Cobol, Perl, Java, and Ada.

Although the present description described in detail certain embodiments, other embodiments are also possible and within the scope of the present invention. For example, those skilled in the art may appreciate from the present description that the present teachings may be implemented in a variety of forms, and that the various embodiments may be implemented alone or in combination. Variations and modifications will be apparent to those skilled in the art from consideration of the specification and figures and practice of the teachings described in the specification and figures, and the claims.

The invention claimed is:

1. A method for sequencing a nucleic acid template, comprising:
   (a) performing a first sequencing process on the nucleic acid template to obtain a first sequencing result, wherein the first sequencing process includes flowing nucleotides and/or reagents to the nucleic acid template according to a first predetermined ordering of nucleotides and/or reagents;
   (b) after the first sequencing process, performing a second sequencing process on the nucleic acid template to obtain a second sequencing result, wherein the second sequencing process includes flowing nucleotides and/or reagents to the nucleic acid template according to a second predetermined ordering of nucleotides and/or reagents, wherein the second predetermined ordering of nucleotides and/or reagents is different from the first predetermined ordering of nucleotides and/or reagents and wherein at least one of the first and second predetermined orderings of nucleotides and/or reagents is designed for repeat sequencing; and
   (c) determining a sequence of bases corresponding to at least a portion of the nucleic acid template using both the first sequencing result and the second sequencing result, wherein determining the sequence of bases comprises:
   generating sets of candidate sequences of bases for each of first sequencing result and the second sequencing result using one or more metrics adapted to associate a score or penalty to the candidate sequences of bases; and
   selecting from the generated sequences of bases the candidate sequence leading to a highest score or a lowest penalty as corresponding to a correct sequence for the nucleic acid template.

2. The method of claim 1, wherein at least one of the first and second predetermined orderings of nucleotides and/or reagents comprises a combination of Kautz sequences generated using all possible dimers of A, C, G, and T.

3. The method of claim 1, wherein at least one of the first and second predetermined orderings of nucleotides and/or reagents comprises a combination of loops through a Kautz graph of possible dimers of A, C, G, and T.

4. The method of claim 1, wherein at least one of the first and second predetermined orderings of nucleotides and/or reagents comprises a series of a predetermined number of predetermined permutations of a combination of at least three loops through a Kautz graph of possible dimers of A, C, G, and T.

5. The method of claim 4, wherein the series of a predetermined number of predetermined permutations of a combination of at least three loops comprises a first loop, followed by a second loop, followed by a third loop, followed by the first loop, followed by the third loop, followed by the second loop.

6. The method of claim 1, wherein at least one of the first and second predetermined orderings of nucleotides and/or reagents comprises a first 4-flow block of flows comprising a first 4-flow permutation of flows A, C, G, and T, followed by a predetermined number of repeats of a first 3-flow permutation of a first set of three flows selected from A, C, G, and T, followed by an isolated flow of the nucleotide not in the first set.

7. The method of claim 6, wherein the isolated flow of the nucleotide not in the first set is followed by a second 4-flow permutation of flows A, C, G, and T different than the first 4-flow permutation, followed by a predetermined number of repeats of a second 3-flow permutation of a second set of three flows selected from A, C, G, and T different than the first set, followed by an isolated flow of the nucleotide not in the second set.

8. The method of claim 7, wherein the isolated flow of the nucleotide not in the second set is followed by a third 4-flow permutation of flows A, C, G, and T different than the first and second 4-flow permutations, followed by a predetermined number of repeats of a third 3-flow permutation of a third set of three flows selected from A, C, G, and T different than the first and second sets, followed by an isolated flow of the nucleotide not in the third set.

9. The method of claim 8, wherein the isolated flow of the nucleotide not in the third set is followed by a fourth 4-flow permutation of flows A, C, G, and T different than the first, second, and third 4-flow permutations, followed by a predetermined number of repeats of a fourth 3-flow permutation of a fourth set of three flows selected from A, C, G, and T different than the first, second, and third sets, followed by an isolated flow of the nucleotide not in the fourth set.

10. The method of claim 1, wherein at least one of the first and second predetermined orderings of nucleotides and/or reagents comprises a pattern selected to delay and/or rotate flows.

11. The method of claim 1, wherein at least one of the first and second predetermined orderings of nucleotides and/or reagents is selected from a combination of building blocks designed for complementary sequencing in both directions.

12. The method of claim 1, wherein both the first and second predetermined orderings of nucleotides and/or reagents comprise a combination of Kautz sequences generated using all possible dimers of A, C, G, and T.

13. The method of claim 1, wherein both the first and second predetermined orderings of nucleotides and/or reagents comprise a combination of loops through a Kautz graph of possible dimers of A, C, G, and T.

14. The method of claim 1, wherein both the first and second predetermined orderings of nucleotides and/or reagents comprise a first 4-flow block of flows comprising a first 4-flow permutation of flows A, C, G, and T, followed by a predetermined number of repeats of a first 3-flow permutation of a first set of three flows selected from A, C, G, and T, followed by an isolated flow of the nucleotide not in the first set.

15. The method of claim 1, wherein generating the sets of candidate sequences of bases for each of first sequencing result and the second sequencing result comprises generating a tree-based data structure comprising sets of partial paths corresponding to candidate sequences undergoing expansion in a stepwise manner one base at a time.

16. The method of claim 15, wherein generating the tree-based data structure comprises determining a predicted signal for each partial path and evaluating a distance between the predicted signal and an observed or measured signal.

17. The method of claim 16, wherein the one or more metrics comprise a metric that is a function of the distance between the predicted signal and the observed or measured signal.

18. A system for sequencing a nucleic acid template, comprising:
 a machine-readable memory; and
 a processor configured to execute machine-readable instructions, which, when executed by the processor, cause the system to perform a method comprising:
  (a) performing a first sequencing process on the nucleic acid template to obtain a first sequencing result, wherein the first sequencing process includes flowing nucleotides and/or reagents to the nucleic acid template according to a first predetermined ordering of nucleotides and/or reagents;
  (b) after the first sequencing process, performing a second sequencing process on the nucleic acid template to obtain a second sequencing result, wherein the second sequencing process includes flowing nucleotides and/or reagents to the nucleic acid template according to a second predetermined ordering of nucleotides and/or reagents, wherein the second predetermined ordering of nucleotides and/or reagents is different from the first predetermined ordering of nucleotides and/or reagents and wherein at least one of the first and second predetermined orderings of nucleotides and/or reagents is designed for repeat sequencing; and
  (c) determining a sequence of bases corresponding to at least a portion of the nucleic acid template using both the first sequencing result and the second sequencing result, wherein determining the sequence of bases comprises:
 generating sets of candidate sequences of bases for each of first sequencing result and the second sequencing result using one or more metrics adapted to associate a score or penalty to the candidate sequences of bases; and
 selecting from the generated sequences of bases the candidate sequence leading to a highest score or a lowest penalty as corresponding to a correct sequence for the nucleic acid template.

19. A non-transitory machine-readable storage medium comprising instructions which, when executed by a processor, cause the processor to perform a method for nucleic acid sequencing comprising:
 (a) performing a first sequencing process on a nucleic acid template to obtain a first sequencing result, wherein the first sequencing process includes flowing nucleotides and/or reagents to the nucleic acid template according to a first predetermined ordering of nucleotides and/or reagents;

(b) after the first sequencing process, performing a second sequencing process on the nucleic acid template to obtain a second sequencing result, wherein the second sequencing process includes flowing nucleotides and/or reagents to the nucleic acid template according to a second predetermined ordering of nucleotides and/or reagents, wherein the second predetermined ordering of nucleotides and/or reagents is different from the first predetermined ordering of nucleotides and/or reagents and wherein at least one of the first and second predetermined orderings of nucleotides and/or reagents is designed for repeat sequencing; and (c) determining a sequence of bases corresponding to at least a portion of the nucleic acid template using both the first sequencing result and the second sequencing result, wherein determining the sequence of bases comprises:

generating sets of candidate sequences of bases for each of first sequencing result and the second sequencing result using one or more metrics adapted to associate a score or penalty to the candidate sequences of bases; and selecting from the generated sequences of bases the candidate sequence leading to a highest score or a lowest penalty as corresponding to a correct sequence for the nucleic acid template.

* * * * *